US009255058B2

(12) United States Patent
Kawata et al.

(10) Patent No.: US 9,255,058 B2
(45) Date of Patent: Feb. 9, 2016

(54) COMPLEX ALCOHOL ESTER COMPOSITION, METHOD FOR PRODUCTION SAME, AND USE OF SAME

(75) Inventors: Ken Kawata, Kanagawa (JP); Akio Tamura, Kanagawa (JP); Saisuke Watanabe, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 320 days.

(21) Appl. No.: 13/498,437

(22) PCT Filed: Sep. 27, 2010

(86) PCT No.: PCT/JP2010/066646
§ 371 (c)(1),
(2), (4) Date: Mar. 27, 2012

(87) PCT Pub. No.: WO2011/037217
PCT Pub. Date: Mar. 31, 2011

(65) Prior Publication Data
US 2012/0184474 A1 Jul. 19, 2012

(30) Foreign Application Priority Data

Sep. 28, 2009 (JP) .................. 2009-222014
Jul. 30, 2010 (JP) .................. 2010-171904

(51) Int. Cl.
*C10M 107/34* (2006.01)
*C07C 69/66* (2006.01)
(Continued)

(52) U.S. Cl.
CPC .............. *C07C 67/08* (2013.01); *C07C 69/40* (2013.01); *C07C 69/44* (2013.01); *C07C 69/50* (2013.01);
(Continued)

(58) Field of Classification Search
CPC ............... C10M 2207/282; C10M 2207/34; C07C 69/34; C07C 69/704
USPC .......................................... 508/497; 560/182
See application file for complete search history.

(56) References Cited

U.S. PATENT DOCUMENTS 3,202,701 A * 8/1965 Pare et al. ............. 560/199
3,914,182 A * 10/1975 Ker et al. ................ 252/75
(Continued)

FOREIGN PATENT DOCUMENTS

EP 0909755 A1 4/1999
GB 808265 B 1/1959
(Continued)

OTHER PUBLICATIONS

Notification of Transmittal of the International Preliminary Report on Patentability (Forms PCT/IB/326 and PCT/IB/373) and the Written Opinion of the International Searching Authority (Form PCT/ISA/237) issued on Oct. 5, 2010, by the International Bureau of WIPO in International Application No. PCT/JP/2010/060639.
(Continued)

*Primary Examiner* — Vishal Vasisth
(74) *Attorney, Agent, or Firm* — Buchanan, Ingersoll & Rooney PC

(57) ABSTRACT

Disclosed is a complex alcohol ester composition comprising a polyester in which at least two molecules of a polyol represented by a formula I: $R(OH)_n$ (wherein R represents an n-valent aliphatic, alicyclic or aromatic group, one or more carbon atoms not adjacent to each other in R may be individually substituted with an oxygen atom, and n indicates an integer of 2 or more) are linked through at least two ester bonds via at least one molecule of a polybasic acid, and at least a part of the non-linked side chain ends of the polyol have a group represented by a formula II: $(AO)_k R^2$ (wherein $R^2$ represents a hydrocarbon group, A represents a divalent linking group, and k indicates an integer) via a polybasic acid. The complex alcohol ester composition can be used a lubricant agent.

30 Claims, 17 Drawing Sheets

GPC Chart of Product in Example 1

(51) Int. Cl.

| | | |
|---|---|---|
| *C07C 67/08* | (2006.01) | |
| *C07C 69/40* | (2006.01) | |
| *C07C 69/44* | (2006.01) | |
| *C07C 69/50* | (2006.01) | |
| *C10M 105/36* | (2006.01) | |
| *C10M 105/38* | (2006.01) | |
| *C10M 105/42* | (2006.01) | |

(52) U.S. Cl.
CPC ........... *C10M 105/36* (2013.01); *C10M 105/38* (2013.01); *C10M 105/42* (2013.01); *C10M 2203/1006* (2013.01); *C10M 2205/0285* (2013.01); *C10M 2207/021* (2013.01); *C10M 2207/026* (2013.01); *C10M 2207/1265* (2013.01); *C10M 2207/1285* (2013.01); *C10M 2207/2825* (2013.01); *C10M 2207/2835* (2013.01); *C10M 2207/2845* (2013.01); *C10M 2207/301* (2013.01); *C10M 2207/3045* (2013.01); *C10M 2209/104* (2013.01); *C10M 2213/0606* (2013.01); *C10M 2215/1026* (2013.01); *C10M 2217/0456* (2013.01); *C10M 2219/068* (2013.01); *C10M 2229/025* (2013.01); *C10N 2230/02* (2013.01); *C10N 2230/06* (2013.01); *C10N 2230/54* (2013.01); *C10N 2240/02* (2013.01); *C10N 2240/04* (2013.01); *C10N 2240/042* (2013.01); *C10N 2240/08* (2013.01); *C10N 2240/10* (2013.01); *C10N 2240/121* (2013.01); *C10N 2240/14* (2013.01); *C10N 2240/204* (2013.01); *C10N 2240/30* (2013.01); *C10N 2240/40* (2013.01); *C10N 2240/401* (2013.01); *C10N 2240/58* (2013.01); *C10N 2250/10* (2013.01)

(56) References Cited

U.S. PATENT DOCUMENTS

| | | | |
|---|---|---|---|
| 5,364,956 A | 11/1994 | Matsumoto | |
| 5,898,023 A | 4/1999 | Francisco et al. | |
| 5,922,658 A | 7/1999 | Duncan et al. | |
| 5,942,475 A | 8/1999 | Schlosberg et al. | |
| 5,994,278 A | 11/1999 | Duncan et al. | |
| 7,119,056 B2 | 10/2006 | Koch et al. | |
| 2003/0166474 A1 | 9/2003 | Winemiller et al. | |
| 2005/0101667 A1 | 5/2005 | Koch et al. | |
| 2005/0176986 A1 | 8/2005 | Matsumoto | |
| 2006/0148897 A1 | 7/2006 | Vernon et al. | |
| 2006/0281874 A1 | 12/2006 | Fitz et al. | |
| 2007/0054814 A1 | 3/2007 | Negoro et al. | |
| 2007/0276121 A1 | 11/2007 | Westergom et al. | |
| 2008/0026967 A1* | 1/2008 | Suda et al. | 508/459 |
| 2012/0201962 A1 | 8/2012 | Kawata et al. | |

FOREIGN PATENT DOCUMENTS

| | | |
|---|---|---|
| JP | 03-169685 A | 7/1991 |
| JP | 4-356441 A | 12/1992 |
| JP | 5-155809 A | 6/1993 |
| JP | 7-330670 A | 12/1995 |
| JP | 10-289436 A | 10/1998 |
| JP | 11-158482 A | 6/1999 |
| JP | 2001-500549 A | 1/2001 |
| JP | 2001-501989 A | 2/2001 |
| JP | 2001-507334 A | 6/2001 |
| JP | 2001-348424 A | 12/2001 |
| JP | 2002-509563 A | 3/2002 |
| JP | 2002-97482 A | 4/2002 |
| JP | 2004-507597 A | 3/2004 |
| JP | 2004-244593 A | 9/2004 |
| JP | 2004-315584 A | 11/2004 |
| JP | 2005-036223 A | 2/2005 |
| JP | 2005-154726 A | 6/2005 |
| JP | 2005-213377 A | 8/2005 |
| JP | 2005-232424 | 9/2005 |
| JP | 2005-232470 A | 9/2005 |
| JP | 2006-257383 A | 9/2006 |
| JP | 2006-328127 A | 12/2006 |
| JP | 2007-092055 A | 4/2007 |
| WO | WO 98/10039 A1 | 3/1998 |
| WO | WO 98/10040 A1 | 3/1998 |
| WO | WO 98/10041 A1 | 3/1998 |
| WO | WO 98/10043 A1 | 3/1998 |
| WO | WO 99/49004 A | 9/1999 |
| WO | WO 00/29521 A1 | 5/2000 |
| WO | WO 03/064573 A1 | 8/2003 |
| WO | WO 2004/024237 | 3/2004 |
| WO | WO 2004/024237 A2 | 3/2004 |
| WO | WO 2009/119831 A1 | 10/2009 |
| WO | WO 2009/119835 A1 | 10/2009 |

OTHER PUBLICATIONS

Vernon et al., "Water-borne, in situ crosslinked biomaterials from phase-segregated precursors", Journal of Biomedical Materials Research Part A, 2003, pp. 447-456.
Barus, American Journal of Science, Feb. 1983, pp. 87-97, vol. 45, No. 266.
Doolittle, "Studies in Newtonian Flow. II. The Dependence of the Viscosity of Liquids on Free-Space", Journal of Applied Physics, Dec. 1951, pp. 1471-1475, vol. 22, No. 12.
Ohno et al., "Some Observations on the Relationship between Rheological Properties of Lubricants at High Pressure and Regimes of Traction (Part 1)", The Rheological Properties of Lubricants at High Pressure, 1988, pp. 922-934.
English Translation of the International Preliminary Report on Patentability (PCT/IB/373) issued on Jan. 17, 2012, by Japanese Patent Office as the International Searching Authority for International Application No. PCT/JP2010/060639.
Hamaguchi et al., "Studies of High-Pressure Physical Properties of Discotic Compound According to Free Volume," Preprint on the International Tribology Conference, Nov. 2005, pp. 175 and partial English translation thereof.
International Search Report (PCT/ISA/210) issued on Dec. 21, 2010, by Japanese Patent Office as the International Searching Authority for International Application No. PCT/JP2010/066646.
Ken Kawata et al., "Composition, Compound and Film Forming Method," U.S. Appl. No. 13/380,616, filed on Dec. 23, 2011.
Notification of Transmittal of Translation of the International Preliminary Report on Patentability(Chapter I and II) (Form PCT/IB/373 & Form PCT/IB/338) and the Written Opinion of the International Searching Authority (Form PCT/ISA/237) issued on Apr. 19, 2012, in the corresponding International Application No. PCT/JP2010/066646. (13 pages).
Office Action issued on Jun. 10, 2014, by the Japanese Patent Office in corresponding Japanese Patent Application No. 2010-171904, and an English Translation of the Office Action. (5 pages).
Office Action issued in corresponding Japanese Application No. 2010-171904 on Aug. 19, 2014 (5 pages).

* cited by examiner

GPC Chart of Product in Example 1

$^1$H-NMR Chart of Compound of Formula 1 in Example 1

GPC Chart of Product in Example 2

GPC Chart of Product in Example 3

¹H-NMR Chart of Product in Example 3

¹³C-NMR Chart of Product in Example 3

Fig. 7
GPC Chart of Product in Example 4
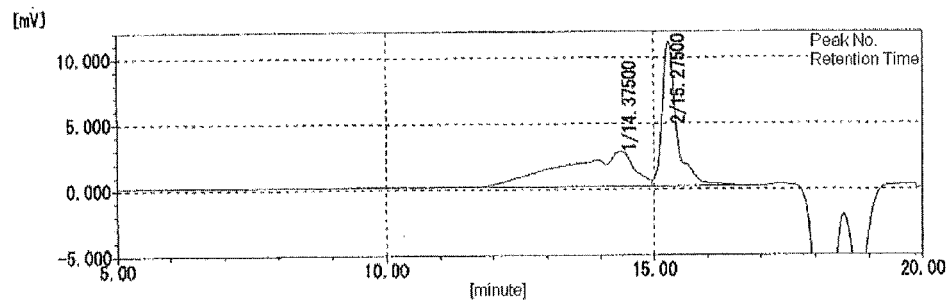
Fig. 8
GPC Chart of Product in Example 5
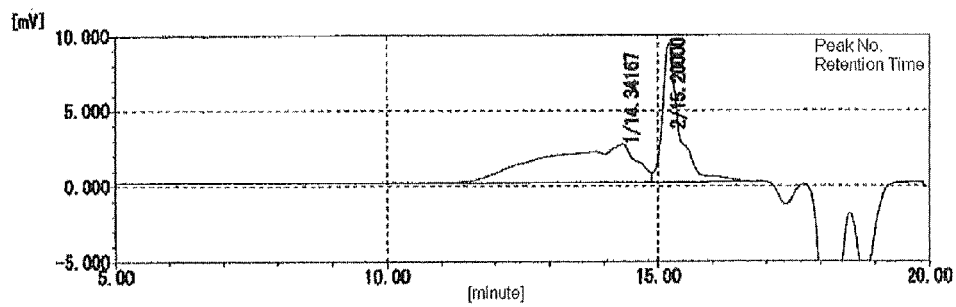
[Fig. 9]
GPC Chart of Product in Example 6
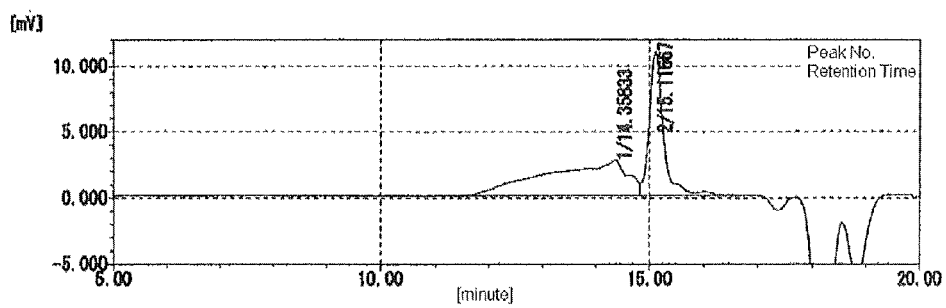

GPC Chart of Product in Example 7

GPC Chart of Product in Example 8

GPC Chart of Product in Example 9

GPC Chart of Product in Example 10

GPC Chart of Product in Example 11

GPC Chart of Product in Example 12

GPC Chart of Product in Example 13

1H-NMR Chart of Light Component Obtained in Example 14

GPC Chart of High-Viscosity Oil Obtained in Example 14

GPC Chart of Product in Example 15

GPC Chart of Product in Example 16

$^{13}$C-NMR Chart of Product in Example 17

GPC Chart of Product in Comparative Example 1

GPC Chart of Product in Comparative Example 2

GPC Chart of Product in Comparative Example 3

GPC Chart of Product in Comparative Example 4

GPC Chart of Product in Comparative Example 5

GPC Chart of Product in Example 18

GPC Chart of Polyester Partitioned from Product in Example 18

$^1$H-NMR Chart of Polyester Partitioned from Product in Example 18

GPC Chart of Product in Example 19

GPC Chart of Product in Example 39

GPC Chart of Product in Example 40

GPC Chart of Product in Example 41

COMPLEX ALCOHOL ESTER COMPOSITION, METHOD FOR PRODUCTION SAME, AND USE OF SAME

This application is a 371 of PCT/JP2010/066646, filed Sep. 27, 2010.

TECHNICAL FIELD

The present invention relates to a complex alcohol ester composition and its production method, and to its use.

BACKGROUND ART

Lubricant generally contains base oil and various additives. As the base oil, there are mentioned mineral oils to be obtained from crude oil, as well as ester-base oils, fluoro-base oils, poly-α-olefin oils and the like to be chemically synthesized. Of those, ester-base oils are favorably used for engine oils for jet planes and automobiles, and for greases, etc., as having a low pour point, a high viscosity index, a high ignition point, good lubrication performance and biodegradability, etc.

As ester-base oils, there are disclosed various types of esters, such as monoesters to be obtained through reaction of an aliphatic monocarboxylic acid and a monoalcohol; diesters to be obtained through reaction of aliphatic dibasic acid and monoalcohol; esters to be obtained through reaction of polyalcohol and aliphatic carboxylic acid; complex esters to be obtained through reaction of polyol, polybasic acid and aliphatic monocarboxylic acid; etc. (Patent References 1 to 5).

On the other hand, disclosed is a complex alcohol ester obtained from polyol, polybasic acid or its anhydride and polyalcohol, which is said to have excellent lubricity and biodegradability (Patent References 6 to 9). These patent publications have no other substantial description relating to polyalcohol than one relating to alkyl alcohol. In addition, the patent publications say that the product obtained through reaction of the above-mentioned materials contains a polybasic acid ester and a heavy component, but suggest that removing the polybasic acid ester through stripping to give a lubricant oil of high-viscosity heavy component is preferred. The patent publications do not describe detailed analysis of these products.

CITATION LIST

Patent Reference

[Patent Reference 1] JP-A 2002-097482
[Patent Reference 2] JP-A 2005-154726
[Patent Reference 3] JP-A 2005-232434
[Patent Reference 4] JP-A 2005-213377
[Patent Reference 5] JP-A 2005-232470
[Patent Reference 6] JP-T 2001-501989
[Patent Reference 7] JP-T 2001-500549
[Patent Reference 8] JP-T 2001-507334
[Patent Reference 9] JP-T 2002-509563

SUMMARY OF THE INVENTION

Problems that the Invention is to Solve

The lubricity of the above-mentioned complex alcohol ester could not be said to be sufficient, and a complex alcohol ester composition is desired, which has further better lubricity, especially low friction, and which is useful as a base oil or additive in lubricant.

Means for Solving the Problems

The present inventors have variously studied for the purpose of solving the above-mentioned problems and, as a result, have considered that when a predetermined group is introduced into the polyol side chain end of polyester, then flexibility could be given to the molecule and the lubricity performance of the obtained complex alcohol ester could be thereby bettered, and have further made various investigations. As a result, the inventors have found that the friction coefficient of a complex alcohol ester composition containing a polyester that has a predetermined group introduced into the polyol side chain end thereof is dramatically reduced as compared with that of already-existing complex alcohol compositions not having the group. Further, regarding the complex alcohol ester composition, the inventors have found a surprising effect that its friction coefficient is almost constant or is rather reduced at the time of temperature increase; and on the basis of these findings, the inventors have completed the present invention. On the other hand, the inventors have further found that various types of additives may be added to the complex alcohol ester composition of the invention and/or the composition can be mixed with various types of media, thereby using favorably using the composition as a low-friction lubricant oil.

That is, the means for solving the above-described problems are as follows.

[1] A complex alcohol ester composition comprising a polyester in which at least two molecules of a polyol represented by a formula I: $R(OH)_n$ (wherein R represents an n-valent aliphatic, alicyclic or aromatic group, one or more carbon atoms not adjacent to each other in R may be individually substituted with an oxygen atom, and n indicates an integer of 2 or more) are linked through at least two ester bonds via at least one molecule of a polybasic acid, and at least a part of the non-linked side chain ends of the polyol have a group represented by a formula II: $(AO)_k R^2$ (wherein $R^2$ represents a hydrocarbon group, A represents a divalent linking group, and k indicates an integer) via a polybasic acid.

[2] The complex alcohol ester composition according to [1], wherein at least one of said polyester has a structure represented by the following formula Y:

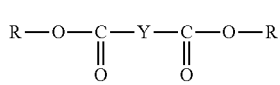

Formula Y wherein R represents a monovalent or more multivalent residue derived from $R(OH)_n$ in [1] by removing at least two OH groups, and Y represents a residue derived from the polybasic acid in [1] by removing two carboxyl groups.

[3] The complex alcohol ester composition according to [1] or [2,] wherein the polyester further comprises a polybasic acid ester-containing light component.

[4] The complex alcohol ester composition according to any one of [1] to [3], which comprises the light component in an amount of at most 90% by mass of the total mass of the composition.

[5] The complex alcohol ester composition according to any one of [1] to [4], wherein n in the formula I is 3 or more.

[6] The complex alcohol ester composition according to any one of [1] to [4], wherein n in the formula I is 3 or 4.
[7] The complex alcohol ester composition according to any one of [1] to [6], wherein R in the formula I contains from 2 to 20 carbon atoms.
[8] The complex alcohol ester composition according to any one of [1] to [7], wherein the polyol is pentaerythritol, trimethylolpropane, glycerin or dipentaerythritol.
[9] The complex alcohol ester composition according to any one of [1] to [8], wherein the polybasic acid is a dibasic acid.
[10] The complex alcohol ester composition according to any one of [1] to [9], wherein the dibasic acid is succinic acid, adipic acid, sebacic acid, or an anhydride thereof.
[11] The complex alcohol ester composition according to any one of [1] to [9], wherein the dibasic acid is a dimer acid or a hydrogenate thereof.
[12] The complex alcohol ester composition according to any one of [3] to [11], wherein the polybasic acid ester that the light component contains is a compound represented by formula VIa:

Formula VIa:

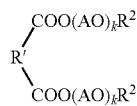

wherein R' represents a linear or cyclic, divalent saturated or unsaturated hydrocarbon group; and $R^2$, A and k have the same meanings as those in the formula II.

The complex alcohol ester composition according to any one of [3] to [11], wherein the polybasic acid ester that the light component contains is a compound represented by the formula VIb:

Formula VIb:

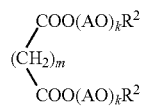

wherein m indicates an integer of from 1 to 10; and $R^2$, A and k have the same meanings as those in the formula II.
[14] The complex alcohol ester composition according to any one of [1] to [13], wherein $R^2$ in the formula II has from 1 to 30 carbon atoms.
[15] The complex alcohol ester composition according to any one of [1] to [14], wherein k in the formula II is from 1 to 30.
[16] The complex alcohol ester composition according to any one of [1] to [15], wherein A in the formula II is an alkylene group having from 1 to 6 carbon atoms, $R^2$ is an alkyl group having from 1 to 6 carbon atoms, and k is an integer of from 1 to 3.
[17] The complex alcohol ester composition according to any one of [1] to [15], wherein A in the formula II is an alkylene group having from 1 to 6 carbon atoms, $R^2$ is an alkyl group having from 16 to 22 carbon atoms, and k is an integer of from 10 to 20.
[18] The complex alcohol ester composition according to any one of [1] to [17], wherein the polyester has a group represented by the formula II and has $OCOR^1$ (wherein $R^1$ represents an alkyl group having from 1 to 10 carbon atoms, or an aryl group) in at least a part of the polyol side chain ends.
[19] The complex alcohol ester composition according to [18], wherein $R^1$ is an alkyl group having from 1 to 4 carbon atoms.
[20] The complex alcohol ester composition according to any one of [1] to [19], of which the viscosity at 40 degrees Celsius is from 50 to 700 mPas.
[21] A composition comprising a complex alcohol ester composition of any one of [1] to [20], and one or more additives selected from a friction inhibitor, a viscosity index improver, an antioxidant, a cleaning agent, a dispersant, a flowing agent, a curing agent, a corrosion inhibitor, a sealability enhancer, a defoaming agent, a rust protector, a friction controlling agent, and a thickener.
[22] A composition comprising a complex alcohol ester composition of any one of [1] to [20], or a composition of [19], and one or more media selected from a mineral oil, an oil and fat compound, a polyolefin oil, a silicone oil, a perfluoropolyether oil, an aromatic ester oil and a polyol ester lubricant oil.
[23] A lubricant comprising a complex alcohol ester composition of any one of [1] to [20], or a composition of [21] or [22].
[24] The lubricant according to [23], which is used as a lubricant oil for grease, a mold release agent, an oil for internal-combustion engines, oil for metal working (cutting), oil for bearings, a fuel for combustion engines, an engine oil for vehicles, a gear oil, an operating oil for automobiles, a lubricant oil for ships and aircraft, a machine oil, a turbine oil, an oil for bearings, a hydraulic operating oil, a compressor/vacuum pump oil, an oil for refrigerators, a metal working lubricant oil, a lubricant oil for magnetic recording media, a lubricant oil for micromachines, a lubricant oil for artificial bones, or a rolling oil.
[25] A method for producing a complex alcohol ester, which comprises:
  mixing
    a polyol represented by a formula I: $R(OH)_n$ (wherein R represents an n-valent aliphatic, alicyclic or aromatic group, one or more carbon atoms not adjacent to each other in R may be individually substituted with an oxygen atom, and n indicates an integer of 2 or more),
    a polybasic acid or a polybasic acid anhydride, and
    a monoalcohol represented by a formula III: $HO(AO)_kR^2$ (wherein $R^2$ represents a hydrocarbon group, A represents a divalent linking group, and k indicates an integer of from 1 to 30),
  and dehydrating and condensing the mixture.
[26] The method according to [25], wherein the equivalent ratio in mixing the polyol, the polybasic acid or polybasic acid anhydride and the monoalcohol is from 1/(1.5 to 2.5)/(1.0 to 3.0).
[27] The method according to [25] or [26], wherein a hydrocarbon solvent having a boiling point of from 110 to 160 degrees Celsius is added to the mixture in an amount of from 1 to 25% by mass of the mixture, and the condensation is carried out under azeotropic dehydration.
[28] The method according to any one of [25] to [27], which comprises a step of adding an acid anhydride after the dehydrating condensation to thereby acylate the remaining OH.

Advantage of the Invention

The complex alcohol ester composition or the lubricant containing it of the invention has a low friction coefficient, and at the time of temperature increase, the friction coefficient thereof is almost constant or is rather reduced. This property is favorable as lubricant. When the lubricant is used in heatgenerating power-system machines, then the energy consumption can be reduced and the fuel cost can be thereby cut.

BRIEF DESCRIPTION OF THE DRAWINGS

FIG. 7 This is a GPC chart of the product in Example 4.
FIG. 8 This is a GPC chart of the product in Example 5.
FIG. 9 This is a GPC chart of the product in Example 6.

MODE FOR CARRYING OUT THE INVENTION

Figure 1:
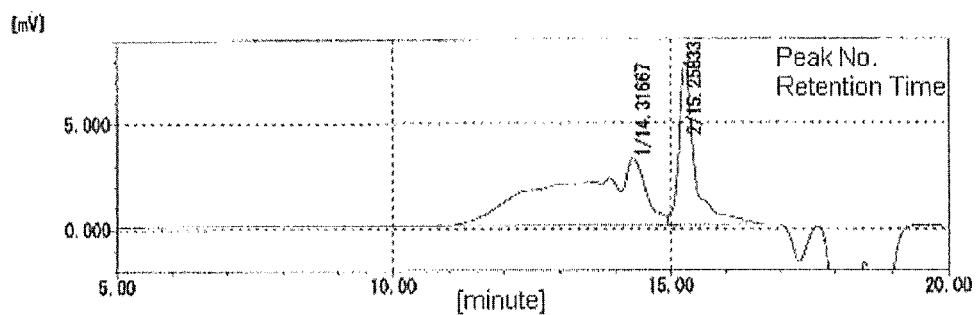
FIG. 1 This is a GPC chart of the product in Example 1.

The invention is described in detail hereinunder. In this description, the numerical range expressed by the wording "a number to another number" means the range that falls between the former number indicating the lowermost limit of the range and the latter number indicating the uppermost limit thereof.

1. Complex Alcohol Ester Composition:

The invention relates to a complex alcohol ester composition containing a predetermined polyester. The composition contains a predetermined polyester as the indispensable ingredient thereof, and preferably contains a light component containing a polybasic acid ester along with the indispensable ingredient. The predetermined polyester is a factor of determining the lubricity of the composition thereof, but it is a solid or a high-viscosity liquid, and therefore, adding a low-viscosity liquid thereto betters the usability of the composition as a base oil of a lubricant oil. Preferably, the low-viscosity liquid is a polybasic acid ester that is produced along with the polyester in the production method of the invention from the viewpoint of the production thereof, to which, however, the invention is not limited.

In the complex alcohol ester composition of the invention, the compositional ratio of the high-polymer polyester and the polybasic acid ester-containing light component could be determined through gel permeation chromatography (GPC). The polybasic acid ester gives a sharp peak in the GPC pattern thereof and its intensity is high, and therefore the ester can be readily detected.

In the invention, the "light component" means a low-molecular-weight component, including the polybasic acid ester formed through reaction of all the carboxyl groups of a polybasic acid or a polybasic acid anhydride with a monoalcohol and any others than those having a smaller molecular weight than that of the polybasic acid ester.

In the complex alcohol ester composition of the invention, the ratio of the polyester to the light component is not specifically defined. Mixing the polyester and the light component betters the lubricity of the composition, which is therefore useful as a lubricant. In an embodiment for use as a lubricant, the ratio of the light component is preferably equal to or less than 90% by mass, more preferably equal to or less than 60% by mass, even more preferably from 30 to 55% by mass. The lower limit of the ratio is not specifically defined, but may be at least 5% by mass for expressing the effect of the mixing.

The ratio could be controlled by controlling the blending ratio of the three starting material in the production method to be mentioned below. By separating the light component through distillation or the like followed by mixing it with the remaining polyester in any desired ratio, the ratio of the components could be controlled to fall within a preferred range.

Preferably, the complex alcohol ester composition of the invention is produced by blending the three starting material as mentioned below followed by dehydrating and condensing them; however, two starting materials (polyol and polybasic acid or polybasic acid anhydride, or polybasic acid or polybasic acid anhydride and monoalcohol) may be first reacted and thereafter with the remaining starting material.

The polybasic acid ester contained in the light component and the high-molecular-weight polyester are similar to each other in point of the structure thereof, and therefore the two well mix with each other. The light component has a low viscosity (10 mPa·s or so at 40 degrees Celsius) and the polyester has a high viscosity (at least 1000 mPa·s or so at 40 degrees Celsius), and the complex alcohol ester of a mixture of the two could have a viscosity falling within a suitable range for lubricant. The suitable viscosity range is equal to or less than 1000 mPa·s at 40 degrees Celsius, preferably from 10 to 1000 mPa·s, more preferably from 30 to 1000 mPa·s, even more preferably from 50 to 700 mPa·s.

In the complex alcohol ester in the invention, in case where the carbon number of $R^2$ in the side chain $(AO)_kR^2$ is large (concretely, in case where the carbon number thereof is from 14 to 30 or so), one or both of the polyester and the polybasic acid may be solid, and the complex alcohol ester may be solid at room temperature. In such a case, any other liquid compound, especially an oily medium to be mentioned below may be added thereto to give a liquid composition. These are favorably used as lubricant. The polybasic acid ester of the complex alcohol ester in the invention may be isolated by separately producing it through reaction of a polybasic acid and a monoalcohol, or by separating it through distillation, and therefore mixing the thus-isolated liquid polybasic acid ester and the solid complex alcohol ester may give a liquid complex alcohol ester composition. These are favorably used as lubricant.

Polyester:

In the polyester that the complex alcohol ester of the invention contains, at least two molecules of a polyol represented by a formula I: $R(OH)_n$ (wherein R represents an n-valent aliphatic, alicyclic or aromatic group, one or more carbon atoms not adjacent to each other in R may be individually substituted with an oxygen atom, and n indicates an integer of 2 or more) are linked through at least two ester bonds via at least one molecule of a polybasic acid, and at least a part of the non-linked side chain ends of the polyol have a group represented by a formula II: $(AO)_k R^2$ (wherein $R^2$ represents a hydrocarbon group, A represents a divalent linking group, and k indicates an integer) via a polybasic acid.

In case where two molecules of a polyol represented by the formula I: $R(OH)_n$ are linked through two ester bonds via one molecule of a polybasic acid, the compound has a structure of the following formula Y. R represents a monovalent or more multivalent residue derived from the formula $R(OH)_n$ by removing at least two OH groups. In R, one or more of n's OHs may remain unreacted. However, at least one chemical bond of at least one of the two R's bonds to the group represented by the formula II: $(AO)_k R^2$ via one or more molecules of the polybasic acid (in case where they bond via two or more molecules of the polybasic acid, R may further exist between them). Y represents a residue derived from the polybasic acid to be mentioned below by removing two carboxyl groups. For example, in case where the polybasic acid is succinic acid, Y may be —$CH_2 CH_2$—, and in case where the acid is citric acid, Y may be —$CH_2 C(OH)(COOH)CH_2$— or —$CH_2 C(OH)(CH_2 COOH)$—. In this, two R's in the following formula Y may bond to each other via further one or more OCOYCOO bonds.

Formula Y:

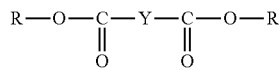

The polyester has a group represented by the formula II: $(AO)_k R^2$ (wherein $R^2$ represents a hydrocarbon group, A represents a divalent linking group, and k indicates an integer), at least in a part of the non-linked side chain ends of the polyol, via a polybasic acid. One example is a partial structure represented by the following formula Z. In the formula, R and Y have the same meanings as those in the above-mentioned formula Y.

Formula Z:

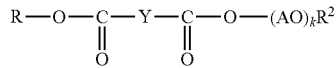

Preferably, at least one type of the polyester that the complex alcohol ester composition of the invention contains is a polyester having a partial structure of the above-mentioned formula Y. More preferably, the complex alcohol ester composition of the invention contains at least one type of a polyester in which at least three polyols bond to the structure according to the same bonding mode as above.

In general, it is known that dehydrating condensation of a polyol and a dibasic acid gives a hyperbranched polyester where the polyol is crosslinked with the dibasic acid and the side chain of the polyester (where the end group is not covalent-bonded) is left unreacted OH or forms COOH through reaction with the dibasic acid (Non-Patent Reference: Journal of Polymer Science: Part A: Polymer Chemistry 2007, p. 2673, and Macromolecular Rapid Communications 2004, Vol. 25, p. 921, etc.). The main chain of the polyester in the invention is the hyperbranched polyester of the type, and is characterized in that at least a part of the non-linked side chain ends of the polyol has the group represented by the formula II: $(AO)_k R^2$. It is considered that introducing the group of the formula II into a part of the side chain ends of the polyol in the polyester could better the lubricity of the polyester.

Polyol:

The polyol moiety of the polyester is represented by the formula I: $R(OH)_n$. In the formula, R represents an n-valent aliphatic, alicyclic or aromatic group, one or more carbon atoms not adjacent to each other in R may be individually substituted with an oxygen atom, and n indicates an integer of 2 or more.

In the formula, n is preferably 3 or 4, or that is, preferred is a triol or a tetraol.

In the formula, R is preferably an n-valent aliphatic group having from 2 to 20 carbon atoms (more preferably from 2 to 15, even more preferably from 2 to 10, still more preferably from 2 to 7, especially preferably from 3 to 5 carbon atoms.) However, the invention is not limited to the range; and depending on the use of the composition, preferably, the carbon number may be rather larger.

In the aliphatic group. one or more carbon atoms not adjacent to each other may be individually substituted with an oxygen atom. Preferred examples of R are groups represented by $C_x H_{2X+2-n}$ (where x indicates a number of from 2 to 20) or $C_x H_{2X+2-n} O_m$ (where x indicates a number of from 2 to 20; and m indicates a number satisfying m<x, and is preferably from 1 to 3).

Examples of the polyol represented by the formula I include the following compounds, to which, however, the invention is not limited. There are mentioned diols such as ethylene glycol, propylene glycol, 1,4-butanediol, 1,3-butanediol, 1,6-hexanediol, 1,4-dimethylolcyclohexane, neopentyl glycol; triols such as trimethylolmethane, trimethylolethane, trimethylolpropane, trimethylolbutane, glycerin; tetraols such as pentaerythritol; maltiols such as dipentaerythritol, tripentaerythritol; sugar alcohols such as xylitol, sorbitol, mannitol, erythritol, maltitol, isomaltose, arbinitol, ribitol, iditol, volemitol, periseitol; sugars such as glucose, etc. Of those, preferred are neopentyl glycol, trimethylolethane, trimethylolpropane, trimethylolbutane, glycerin, pentaerythritol, dipentaerythritol, and xylitol; more preferred are trimethylolpropane, trimethylolbutane, glycerin, pentaerythritol, and dipentaerythritol, etc.; even more preferred are trimethylolpropane, glycerin, pentaerythritol, dipentaerythritol, etc.; and especially preferred are pentaerythritol and trimethylolpropane. These may be not necessarily high-purity products, but so-called industrial-use brands may be preferably used here. An industrial-use brand of pentaerythritol is said to comprise about 88% of mono-, 10% of di- and from 1 to 2% of tri-pentaerythritols; and the industrial-use brand of the pentaerythritol or the like can be used as polyol in the invention.

Polybasic Acid or Polybasic Acid Anhydride:

As the polybasic acid ingredient of the polyester, preferred is a compound having multiple COOHs in one molecule. Above all, preferred is a dibasic acid; more preferred is a dibasic acid where two COOHs are linked via a linear or cyclic, divalent saturated or unsaturated hydrocarbon group therebetween; and even more preferred is a dibasic acid where two COOHs are linked via an alkylene group. Preferred examples of the dibasic acid include a dibasic acid where two COOHs are linked via an alkylene group having from 1 to 8 carbon atoms (more preferably from 1 to 6 carbon atoms) therebetween (or that is, a compound represented by $C_yH_{2y}(COOH)_2$, in which y indicates a number of from 1 to 8 (more preferably from 1 to 6)).

Examples of the polybasic acid include the following compounds, to which, however, the invention is not limited. The compounds include terephthalic acid, phthalic acid, malonic acid, succinic acid, glutaric acid, adipic acid, suberic acid, azelaic acid, sebasic acid, dodecanedioic acid, trimellitic acid, dimer acid, dimer acid hydrogenate, etc. Of those, preferred are succinic acid, adipic acid, sebasic acid, dimer acid, and dimer acid hydrogenate; and more preferred are succinic acid, adipic acid, and dimer acid.

The polybasic acid anhydride is, for example, a product produced through intramolecular or intermolecular dehydrating condensation of two COOHs in the above-mentioned polybasic acid. This is usable here in place of the polybasic acid. Preferred embodiments of the anhydride are the same as mentioned above. Examples of the anhydride include succinic anhydride, glutaric anhydride, adipic anhydride, maleic anhydride, phthalic anhydride, najic anhydride, methylnajic anhydride, hexahydrophthalic anhydride, and mixed polybasic acid anhydrides. Of those, preferred are succinic anhydride, adipic anhydride, maleic anhydride, phthalic anhydride, etc.; more preferred are succinic anhydride and adipic anhydride; and even more preferred is succinic anhydride.

Side Chain of Polyester:

As descried above, the polyester is characterized by having the group represented by the formula II: $(AO)_kR^2$ in at least a part of the side chain ends of the polyol.

In the formula II, $R^2$ represents a hydrocarbon group, A represents a divalent linking group, and k indicates an integer of from 1 to 30.

In the above formula, $R^2$ is preferably a hydrocarbon group having from 1 to 30 carbon atoms, more preferably an alkyl group having from 1 to 30 carbon atoms, even more preferably from 1 to 25 carbon atoms, still more preferably from 1 to 20 carbon atoms. Of those, when $R^2$ is an alkyl group having from 1 to 6 carbon atoms, especially a methyl group or an ethyl group, the composition is favorably used as a base oil.

In the above formula, A represents a divalent linking group, and is preferably an alkylene group having from 1 to 6 carbon atoms, more preferably an ethylene group ($-CH_2CH_2-$) or a propylene group ($-CH(CH_3)CH_2-$ or $-CH_2CH(CH_3)-$), even more preferably an ethylene group.

In the above formula, k indicates an integer of from 1 to 30, preferably from 1 to 25, more preferably from 1 to 20, even more preferably from 1 to 10.

Preferred examples of the group represented by the above formula II include the following that indicates the formula II wherein A is an alkylene group having from 1 to 6 carbon atoms, $R^2$ is an alkyl group having from 1 to 8 carbon atoms, and k is an integer of from 1 to 3.

$-(C_nH_{2n}O)_kC_mH_{2m+1}$ (wherein n is from 1 to 6, m is from 1 to 8, and k is from 1 to 3).

Specifically, preferred examples of the group represented by the formula II include the following groups. In the following formulae, k has the same meaning as k in the formula II, and the preferred range thereof is also the same as that of the latter. In the following formula, z is a number of from 1 to 30 (preferably from 1 to 25, more preferably from 1 to 20).

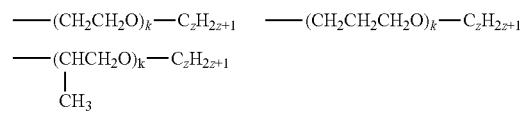

The presence of $(AO)_kR^2$ in the side chain of the polyester in the invention is self-obvious in consideration of the production mechanism of the polyester. However, it is difficult to determine the matter as to whether or not $(AO)_kR^2$ could be derived from the starting alcohol or polybasic acid ester through spectrometry. Consequently, in determining the quality and/or the quantity of $(AO)_kR^2$ as the side chain of the polyester, the complex alcohol ester composition of the invention may be separated into the polyester component and the light component containing the polybasic acid ester through partitioning GPC or the like, and the polyester component may be analyzed. In this, when $(AO)_kR^2$ could be detected through spectrometry, then it demonstrates the presence of the side chains in the polyester.

In the side chains of the polyester in the invention, it is needless to say that the unreacted OH in the polyol may remain, or the OH in the polyol may react with a polybasic acid or polybasic acid anhydride to form COOH existing therein.

However, in case where OH or COOH remains in the polyester in the invention, the hydroxyl value and the acid value of the polyester may increase, which may be often unfavorable in some uses (for example, in use for lubricant). In such a case, the polyester may be separately acylated and/or esterified to thereby remove OH and COOH in the polyester, thereby reducing the hydroxyl value and the acid value.

A polyester having OH remaining in the side chain therein may be once formed and then at least a part of OHs may be acylated to give the polyester for use in the invention. Specifically, preferred examples of the polyester include a polyester having a group represented by the above-mentioned formula II and also $OCOR^1$ in at least a part of the polyol side chain ends thereof. In this, $R^1$ represents an alkyl group having from 1 to 10 carbon atoms, or an aryl group, preferably a methyl group, an ethyl group, a butyl group or a phenyl group, more preferably a methyl group or a phenyl group, even more preferably a methyl group. The acylation is a treatment of adding a monobasic acid ($R^1COOH$) or a monobasic acid anhydride ($(R^1CO)_2O$), preferably a monobasic acid anhydride ($(R^1CO)_2O$ to the polyester where OH remains followed by heating it thereby convert the remaining OH into $OCOR^1$. Reducing the hydroxyl value through the acylation is favorable from the viewpoint that the polyester can be more readily mixed with any other oily medium.

For reducing the acid value of the polyester for use in the invention, a treatment of removing COOH may also be employed. Specifically, examples of the polyester include a polyester in which a part or all of COOHs formed through reaction of the OH in a polyol with a polybasic acid or a polybasic acid anhydride are esterified. For example, the polyester may be one having $COOCH_3$ or the like as esterified through treatment with diazomethane or the like.

The ratio of the unreacted OH in the polyester can be determined through $^{13}C$-NMR. For example, in case where the polyol is pentaerythritol, there may exist 0, 1, 2, 3 or 4 OHs that ester-bonding therein; and the chemical shift of these quaternary carbons separates at around 40 ppm. When the integrated value is determined, then the proportion could be found and the OH remaining ratio could be thereby determined.

For use in lubricant, the OH remaining ratio in the polyester is preferably from 0 to 40%, more preferably from 0 to 35%, even more preferably from 0 to 30%.

In the same use, the acid value of the polyester (the number of mg of KOH necessary for neutralizing one g of sample) is preferably from 0 to 50, more preferably from 0 to 40, even more preferably from 0 to 30. However, the invention is not limited to this range.

Light Component:

The complex alcohol ester composition of the invention may contain a light component. The light component is meant to include a polybasic acid ester formed through reaction of all the carboxyl group of a polybasic acid or a polybasic acid anhydride with a monoalcohol, and any others having a smaller molecular weight than the ester. Concretely, the component means a polybasic acid ester formed through reaction of from 1 to all of the carboxyl groups of a polybasic acid or a polybasic acid anhydride with from 1 to all of the carboxyl groups with a monoalcohol, as well as the starting material and the solvent used in the reaction. The polybasic acid ester formed through esterification of all the carboxyl groups can be separately produced from a polybasic acid or a polybasic acid anhydride and a monoalcohol. Accordingly, the presence of the ester in the complex alcohol ester composition of the invention can be confirmed through GPC and/or NMR. In the invention, in case where a polyol, a polybasic acid or a polybasic acid anhydride, and a predetermined monoalcohol are dehydrated and condensed according to the production method to be mentioned below, there is obtained the above-mentioned polyester formed by the reaction of all these three, and a polybasic acid ester that is a dehydrated condensate of the polybasic acid or the polybasic acid anhydride and the monoalcohol. The polybasic acid ester may be a mixture of esters formed through esterification of from 1 to all the COOHs contained in the polybasic acid.

In the light component, there may remain the polyol, the polybasic acid or the polybasic acid anhydride, and the monoalcohol used for the reaction, but preferably, the monoalcohol is removed through final evaporation. In case where the remaining monoalcohol is contained in light component, the amount thereof is preferably from 0.01 to 50% by mass of the light component, more preferably from 0.1 to 20% by mass, even more preferably from 0.1 to 10% by mass. Preferably, the amount and the reaction condition thereof are so controlled that the polyol and the polybasic acid or the polybasic acid anhydride are fed to the system so that they do not remain in the formed polyester. In case where the acid anhydride is acylated after the dehydrating condensation, an acid may be produced as a side product and may remain in the product, but preferably, the acid is removed.

The polybasic acid ester, when having a small molecular weight, may be removed through evaporation. However, as described above, since the composition of the light component betters the lubricity of the polyester as lubricant, preferably, the ester is left remaining as such in the polyester.

Preferably, the polybasic acid ester in the invention is a dibasic acid ester from the viewpoint of reducing the viscosity of the composition. In particular, it is desirable that the light component contains a dibasic acid ester represented by the following formula VIa. As described above, the ester can be produced separately, and can be confirmed through various spectrometry.

Formula VIa:

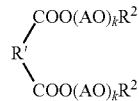

In the above formula, R' represents a linear or cyclic, divalent saturated or unsaturated hydrocarbon group; and $R^2$, A and k have the same meanings as those in the above-mentioned formula II, and the preferred range thereof is also the same as that of the latter.

Examples of the linear saturated divalent hydrocarbon group represented by R' include an alkylene group having from 1 to 10 carbon atoms (preferably from 2 to 10, more preferably from 2 to 8, even more preferably from 2 to 6 carbon atoms). Examples of the linear unsaturated divalent hydrocarbon group represented by R' include an alkenylene group and an alkynylene group having from 2 to 10 carbon atoms (preferably from 2 to 8, more preferably from 2 to 6 carbon atoms). These unsaturated hydrocarbon groups may contain two or more double bonds and triple bonds.

Examples of the cyclic saturated divalent hydrocarbon group represented by R' include a cycloalkylene group having from 3 to 40 carbon atoms. Examples of the cyclic saturated divalent hydrocarbon group represented by R' include a cycloalkenylene group and a cycloalkynylene group having from 3 to 40 carbon atoms. These cyclic hydrocarbon groups may be a single-ring structure or a multi-ring structure.

Preferred examples of the dibasic acid esters represented by the above-mentioned formula VIa include dibasic acid esters represented by the following formula VIb:

Formula VIb:

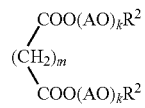

In the above formula, m indicates an integer of from 1 to 10, and is preferably from 2 to 10, more preferably from 2 to 8, even more preferably from 2 to 6. $R^2$, A and k have the same meanings as those in the above-mentioned formula II, and the preferred range thereof is also the same as that of the latter.

Method for Producing Complex Alcohol Ester of the Invention:

One example of the method for producing the complex alcohol ester of the invention is:

a method for producing a complex alcohol ester, including mixing a polyol represented by the formula I: $R(OH)_n$, a polybasic acid or a polybasic acid anhydride, and a monoalcohol represented by a formula III: $HO(AO)_kR^2$, and dehydrating and condensing the mixture.

As described above, it is known that dehydrating condensation of a polyol and a dibasic acid gives a hyperbranched polyester where the polyol is crosslinked with the dibasic acid and the side chain of the polyester (where the end group is not covalent-bonded) is left unreacted OH or forms COOH through reaction with the dibasic acid (Non-Patent Reference: Journal of Polymer Science: Part A: Polymer Chemistry 2007, p. 2673, and Macromolecular Rapid Communications 2004, Vol. 25, p. 921, etc.). According to the method, similarly, the main chain of the polyester is the hyperbranched polyester; but according to the method, the polyester is further reacted with the monoalcohol and therefor the molecular weight thereof is not so large. In addition, according to the method, the crosslinking occurs at random, and therefore the molecular weight distribution of the polyester is large and multimodal. The range of the polystyrene-equivalent molecular weight of the polyester could be from a few hundred to hundreds of thousands. These could be confirmed through gel permeation chromatography (GPC).

In case where the starting monoalcohol is not introduced into the side chain of the polyester, then the molecular weight of the polyester to be produced through dehydrating condensation of the polyol and the polybasic acid or its anhydride according to the above-mentioned method would increase, and if so, the product would be solid, or that is, could not be liquid at room temperature. In other words, the fact that the molecular weight of the product produced according to the above-mentioned method does not increase so much and the product is oily at room temperature could indicate that the starting monoalcohol has been introduced into the side chain of the polyester.

The charging ratio of the three starting materials is defined as the equivalent ratio thereof. Equivalent as referred to herein means the chemical equivalent of COON or OH in reaction. When the OH number in one molecule of polyol is defined as n and the molar number thereof is as M1, then the equivalent of the polyol is defined as n×M1. Similarly, when the COOH number in one molecule of a polybasic acid is defined as m and the molar number thereof is as M2, then the equivalent of the polybasic acid is defined as m×M2. A polybasic acid anhydride is computed as the hydrolyzed polybasic acid thereof. A monoalcohol has one OH in one molecule, and therefore when the molar number thereof is M3, then the equivalent thereof is defined as M3. The above-mentioned ratio is the ratio of these n×M1, m×M2 and M3.

In the above-mentioned method, the charging equivalent ratio of the polyol to the polybasic acid or the polybasic acid anhydride to the monoalcohol is not specifically defined, but may be generally 1/(1.5 to 2.5)/(1.0 to 3.0), preferably 1/(1.8 to 2.3)/(0.7 to 1.5), more preferably 1/(1.8 to 2.2)/(0.8 to 1.5), even more preferably 1/(1.8 to 2.2)/(0.9 to 1.4). In particular, the side chain of the complex alcohol ester is preferably end-capped, and therefore it is desirable that the total equivalent of the polyol and the monoalcohol is the same as or larger than the equivalent of the polybasic acid or the polybasic acid anhydride.

The mixture thus fed in the manner as above is dehydrated and condensed in the presence or absence of a catalyst to give the complex alcohol ester composition of the invention.

In dehydrating condensation, the system may be heated, and preferably, a suitable amount of a solvent capable of azeotroping with water is made to exist in the system. Accordingly, the dehydration could go on smoothly with no discoloration of the product. The solvent is preferably a hydrocarbon solvent having a boiling point of from 100 to 200 degrees Celsius, more preferably a hydrocarbon solvent having a boiling point of from 100 to 170 degrees Celsius, most preferably a hydrocarbon solvent having a boiling point of from 110 to 160 degrees Celsius. As the solvent, for example, there are mentioned toluene, xylene, mesitylene, etc. Regarding the amount thereof to be added, when the solvent is added too much, then the liquid temperature may be near to the temperature of the solvent and the dehydrating condensation could hardly go on. On the other hand, when too small, the azeotropic reaction could not go on smoothly. Accordingly, the amount to be added is preferably from 1 to 25% by mass of the entire amount of the polyol, the polybasic acid or the polybasic acid hydride and the monoalcohol, more preferably from 2 to 20% by mass, even more preferably from 3 to 15% by mass, most preferably from 5 to 12% by mass.

Using a catalyst may accelerate the reaction, but the post-treatment of catalyst removal is troublesome and the catalyst, if used, may cause discoloration of the product; and consequently, it is desirable not to use a catalyst. However, when used, the catalyst may be an ordinary catalyst and ordinary condition and operation may be applied to the reaction. Regarding this, the references in JP-T 2001-501989, 2001-500549, 2001-507334 and 2002-509563 may be referred to here.

After the charging, the materials are reacted at a liquid temperature of from 120 to 250 degrees Celsius, preferably from 130 to 230 degrees Celsius, more preferably from 130 to 200 degrees Celsius, even more preferably from 140 to 200 degrees Celsius. Accordingly, the solvent containing water can be azeotroped and cooled in a cooling zone such as a Dean Stark apparatus to be liquid, whereby the solvent and water are separated from each other. This water may be removed.

Regarding the reaction time, the theoretical amount of water to be generated can be computed from the charging molar number, and therefore it is desirable that the reaction is continued until the water amount could be obtained, however, it is difficult to completely finish the reaction. At the time when the theoretical amount of water to be generated has reached from 60 to 90%, the reaction could be finished to give a complex alcohol ester composition having good lubricity. The reaction time may be from 1 to 24 hours, preferably from 3 to 18 hours, more preferably from 5 to 18 hours, most preferably from 6 to 15 hours.

After the dehydrating condensation and the volatile removal, further remaining OH may be acylated. For the acylation, a suitable amount of a monobasic acid ($R^1COOH$) or a monobasic acid anhydride (($R_1CO)_2O$), preferably a monobasic acid anhydride (($R_1CO)_2O$) is added to the system and heated preferably at 100 degrees Celsius or higher, more preferably at 120 degrees Celsius or higher, even more preferably at 150 degrees Celsius or higher, whereby at least a part, preferably almost all of the remaining OH can be converted into $OCOR^1$. The volatile generated as a side product is preferably removed through distillation to be mentioned below.

$R^1$ is an alkyl group having from 1 to 10 carbon atoms or an aryl group, preferably an alkyl group having from 1 to 6 carbon atoms or an aryl group, more preferably a methyl group, an ethyl group, a butyl group or a phenyl group, even more preferably a methyl group or a phenyl group, especially preferably a methyl group.

After the dehydrating condensation and the volatile removal, the product may be further esterified in order to remove COOH that is formed through reaction of OH in the polyol with the polybasic acid or the polybasic acid anhydride. The esterification may be attained by addition of diazomethane whereby at least a part, preferably almost all of the formed COOH can be converted into a methyl ester.

According to the reaction, there is obtained the complex alcohol ester composition of the invention that comprises the predetermined polyester and a soft component containing at least the polybasic acid ester. After the dehydrating condensation reaction, if desired, further after the optional acylation and/or esterification treatment, the obtained complex alcohol ester composition can be used directly as it is in various applications, for example, as lubricant. Depending on the use thereof, the composition may be further processed variously. For example, in order to make the composition have evaporative characteristics suitable as lubricant, it is desirable to remove the volatile component, especially the azeotropic solvent and the monoalcohol from the composition. In case where the molecular weight of the monoalcohol used as the reaction starting material is small, the polybasic acid ester may be evaporated away, and therefore the distillation condition such as the degree of pressure reduction and the temperature must be controlled.

After the reaction and the post-treatment, preferably, the product is filtered to remove impurities, etc. In case where the complex alcohol ester is solid, it may be taken out after melted, or may be taken out as a powder formed through reprecipitation.

The polyol represented by the formula I and the polybasic acid or the polybasic acid anhydride to be used as the starting materials for the above-mentioned production method of the invention are the same as the polyol represented by the formula I and the polybasic acid or the polybasic acid anhydride described in detail hereinabove in relation to the above-mentioned polyester, and the preferred range thereof is also the same as that of the latter.

The monoalcohol to be used as the starting material in the production method of the invention is a compound represented by the following formula III. The group represented by the formula II, which at least a part of the side chain of the polyester has, is a residue of the monoalcohol, and therefore the preferred range thereof is the same as mentioned above.

$HO(AO)_k R^2$  Formula III $R^2$ represents a hydrocarbon group, A represents a divalent linking group, and k indicates an integer of from 1 to 30.

The monoalcohol may be in the form of a mixture of different monoalcohols. The monoalcohol may be a mixture of different monoalcohols where A and/or $R^2$ differ, or a mixture thereof where k differs. For example, adding k mols of ethylene oxide or propylene oxide to $HOR^2$ gives $HO(AO)_k R^2$ (where A is an ethylene or propylene group), which may form a mixture of 1 to m mol additives (where m is an integer, and m>k). The mixture of the type can be used here.

Examples of the monoalcohol represented by the above-mentioned formula include the following compounds, to which, however, the invention is not limited. There are mentioned ethylene oxide adducts such as ethylene glycol monomethyl ether, ethylene glycol monoethyl ether, ethylene glycol monobutyl ether, ethylene glycol monophenyl ether, ethylene glycol monobenzyl ether, diethylene glycol monomethyl ether, diethylene glycol monoethyl ether, diethylene glycol monobutyl ether, diethylene glycol monophenyl ether, diethylene glycol monobenzyl ether, triethylene glycol monomethyl ether, triethylene glycol monoethyl ether, triethylene glycol monobutyl ether, triethylene glycol monophenyl ether, triethylene glycol monobenzyl ether, polyethylene glycol monooctyl ether, polyethylene glycol monodecyl ether, polyethylene glycol monododecyl ether, polyethylene glycol monotetradecyl ether, polyethylene glycol monohexadecyl ether, polyethylene glycol monooctadecyl ether, polyethylene glycol monoeicosyl ether, polyethylene glycol monodocosyl ether, polyethylene glycol monotetracosyl ether (in these, poly means from 4 to 50 on average), especially Takemoto Oil & Fat's Pionin series; propylene oxide adducts such as propylene glycol monomethyl ether, propylene glycol monoethyl ether, propylene glycol monobutyl ether, propylene glycol monophenyl ether, propylene glycol monobenzyl ether, dipropylene glycol monomethyl ether, dipropylene glycol monoethyl ether, dipropylene glycol monobutyl ether, dipropylene glycol monophenyl ether, dipropylene glycol monobenzyl ether, tripropylene glycol monomethyl ether, tripropylene glycol monoethyl ether, tripropylene glycol monobutyl ether, tripropylene glycol monophenyl ether, tripropylene glycol monobenzyl ether, etc.

In another aspect thereof, the invention provides:

a complex alcohol ester composition containing a dehydrating condensation reaction product of a mixture that contains:

a polyol represented by a formula I: $R(OH)_n$ (wherein R represents an n-valent aliphatic, alicyclic or aromatic group, and n indicates an integer of 2 or more), a polybasic acid or a polybasic acid anhydride, and a monoalcohol represented by a formula III: $HO(AO)_k R^2$ (wherein $R^2$ represents a hydrocarbon group, A represents a divalent linking group, and k indicates an integer), preferably in an equivalent ratio of 1/(1.5 to 2.5)/(1.0 to 3.0).

Preferred examples of the polyol, the polybasic acid or the polybasic acid anhydride, and the monoalcohol are the same as those mentioned above. The complex alcohol ester composition preferably contains a light component containing a polybasic acid ester (preferably, a dibasic acid ester compound represented by the above-mentioned formula VI), and the preferred range of its proportion is the same as mentioned above.

The present invention relates also to a composition containing the complex alcohol ester composition of the present invention. Various materials which can be used for preparing the composition of the present invention will be described in detail hereinafter.

2. Medium

The composition may contain any medium along with the complex alcohol ester composition. The "medium" as referred to in the invention means all of media generally called "flowability liquid". However, it is not required that the medium is liquid at room temperature or a temperature at which it is used, and in addition to liquids, materials in any form including a solid, a gel, etc. can be used. The medium which is utilized in the invention is not particularly limited and can be selected among various liquids depending upon an application. More specifically, the medium can be selected among various oils, for example, mineral oils to be used as a base oil of lubricating oils or animal or vegetable fat and oil compounds including cooking oils; various chemical synthetic oils such as polyolefin oils, alkylbenzene oils, alkylnaphthalene oils, biphenyl oils, diphenylalkane oils, di(alkylphenyl)alkane oils, ester oils, polyglycol oils, polyphenyl ether oils, fluorocarbon compounds (for example, perfluoro polyethers, fluorinated polyolefins, etc.), silicone oils, ion fluids, etc.; and the like, In an embodiment in which the composition of the invention is used as a substitute of the lubricating oil, mineral oils, polyolefin oils and silicone oils are preferably used from the standpoint of a frictional characteristic. And for the composition to be used for lubrication of any biological body or bones or to be used for flatting or cutting work of any metal or ceramics, water or hydrophilic fluid such as $C_{12}$ or shorter linear or branched alcohol, ethylene glycol and polyethylene glycol is preferably used.

The respective oily media are hereunder described in detail.

As the mineral oil, mineral oils obtained by a method which is usually adopted in a lubricating oil manufacturing process in the petroleum refining industry can be utilized. More specifically, paraffin based, naphthene based or other based mineral oils obtained by refining a lubricating oil fraction obtained by subjecting a crude oil to atmospheric distillation and vacuum distillation by properly combining one or two or more techniques selected among solvent deasphalting, solvent extraction, hydrocracking, solvent dewaxing, catalytic dewaxing, hydrogenation refining, sulfuric acid washing, clay treatment, etc. can be used.

Moreover, as the fat and oil, for example, beef tallow, lard, sunflower oil, soybean oil, rapeseed oil, rice-bran oil, coconut oil, palm oil, palm kernel oil and hydrogenated products thereof, etc. can be used.

As the biodegradable oil, for example, various biodegradable vegetable oils extracted from fruits, seeds or the like of plants, such as rapeseed oil, sunflower oil, soybean oil, etc. or synthetic oils can be utilized. Moreover, polyol ester oils disclosed in JP-A-6-1989 are suitably used. Even among synthetic oils, those exhibiting biodegradability such that a biodegradation rate after a lapse of 21 days is in general 67% or more (preferably 80% or more) in conformity with a method stipulated in the CEC (Coordinating European Council) Standards, L-33-T82 as an evaluation method of biodegradability, can be utilized as the biodegradable oil.

Moreover, it is preferable that the polyolefin oil is selected among those obtained by polymerizing one or two or more olefins having 2 to 12 carbon atoms. Moreover, those obtained by polymerizing one or two or more members of ethylene, propylene, 1-butene, 2-butene, isobutene and a linear terminal olefin (hereinafter referred to as "α-olefin") having from 5 to 12 carbon atoms are more preferable.

Of these, a copolymer of ethylene and propylene; a copolymer of ethylene and an α-olefin having from 5 to 12 carbon atoms; and polybutene, polyisobutene or a polymer of an α-olefin having from 5 to 12 carbon atoms are preferable; and a copolymer of ethylene and an α-olefin having from 5 to 12 carbon atoms and a polymer of an α-olefin having from 5 to 12 carbon atoms are more preferable. In this specification, the "copolymer of ethylene and an α-olefin having from 5 to 12 carbon atoms" refers to a copolymer obtained by polymerizing ethylene and one or two or more α-olefins having from 5 to 12 carbon atoms; and the "polymer of an α-olefin having from 5 to 12 carbon atoms" refers to a homopolymer obtained by polymerizing one α-olefin having from 5 to 12 carbon atoms or a copolymer obtained by polymerizing two or more α-olefins having from 5 to 12 carbon atoms.

An average molecular weight of each of the foregoing copolymer of ethylene and an α-olefin having from 5 to 12 carbon atoms and polymer of an α-olefin having from 5 to 12 carbon atoms is preferably from 500 to 4,000.

Moreover, the silicone oil can be selected among various organic polysiloxanes. Examples of the organic polysiloxane which can be used as the silicone oil include a polymer having a repeating unit represented by the following general formula:

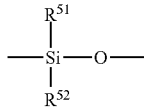

(in the formula, each of $R^{51}$ and $R^{52}$ represents an alkyl group, an aryl group or an aralkyl group, and $R^1$ and $R^2$ may be the same as or different from each other). The organic polysiloxane may be a so-called homopolymer type organic polysiloxane composed of only the subject repeating unit or may be a random type, block type or graft type organic polysiloxane composed of a combination of two or more of these repeating units. The silicone oil is preferably selected among linear polysiloxanes which are liquid or pasty at ordinary temperature, for example, methyl polysiloxane, methyl phenyl polysiloxane, ethyl polysiloxane, ethyl methyl polysiloxane, ethyl phenyl polysiloxane, hydroxymethyl polysiloxane and alkyl polydimethylsiloxanes; cyclic polysiloxanes, for example, octamethyl cyclopentasiloxane and decamethyl cyclopentasiloxane; and mixtures of these compounds.

The perfluoro polyether oil can be selected among compounds obtained by substituting a hydrogen atom of an aliphatic hydrocarbon polyether with a fluorine atom. Examples of such a perfluoro polyether oil include side chain-containing perfluoro polyethers represented by any of following formulae (Z) and (XI); and linear perfluoro polyethers represented by any of following formulae (XII) to (XIV). These compounds can be used singly or in admixture of two or more kinds thereof. In following formulae, each of m and n represents an integer.

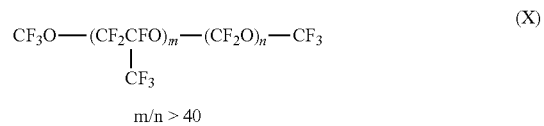

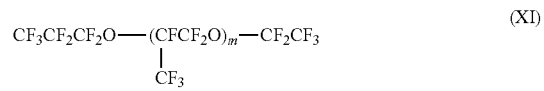

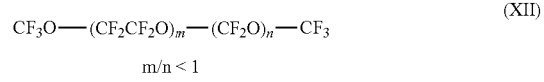

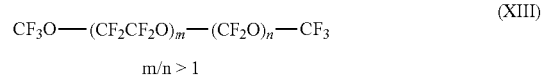

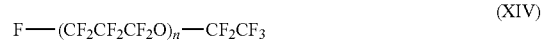

Examples of commercially available products of the foregoing formula (Z) include FOMBLIN Y (a trade name of Montedison); examples of commercially available products of (XI) include KRYTOX (a trade name of Du Pont) and BARRIERTA J OIL (a trade name of Kluber Inc.); examples of commercially available products of (XII) include FOMBLIN Z (a trade name of Montedison); examples of commercially available products of (XIII) include FOMBLIN M (a trade name of Montedison); and examples of commercially available products of (XIV) include DEMNUM (a trade name of Daikin Industries, Ltd,), etc.

The aromatic ester oil is preferably selected among trimellitic acid ester oils represented by the following general formula (XV).

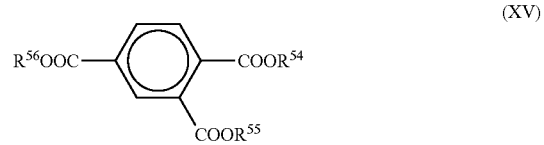

In the formula, each of $R^{54}$, $R^{55}$ and $R^{56}$ represents a hydrocarbon group having from 6 to 10 carbon atoms, and $R^{54}$, $R^{55}$ and $R^{56}$ may be the same as or different from each other. In this connection, the "hydrocarbon group" means a saturated or unsaturated, linear or branched alkyl group.

Moreover, the aromatic ester oil is preferably selected among pyromellitic acid ester oils represented by the following general formula (XVI).

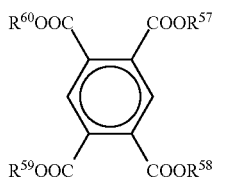

(XVI)

In the formula, each of $R^{57}$, $R^{58}$, $R^{59}$ and $R^{60}$ represents a hydrocarbon group having from 6 to 15 carbon atoms, and $R^{57}$, $R^{58}$, $R^{59}$ and $R^{60}$ may be the same as or different from each other. In this connection, the "hydrocarbon group" means a saturated or unsaturated, linear or branched alkyl group.

As the base oil with excellent heat resistance, though there are known a polyphenyl ether oil, a silicone oil, a fluorocarbon oil and the like, a polyphenyl ether oil, a fluorocarbon oil and a silicone oil are expensive, and a fluorocarbon oil and a silicone oil are generally poor in lubricating properties. On the other hand, the foregoing aromatic ester oil such as a trimellitic acid ester oil and pyromellitic acid ester oil has excellent characteristics in heat resistance, oxidation resistance and wear resistance. In particular, since the aromatic ester oil represented by the foregoing general formula (XV) or (XVI) is low in a pour point and high in a viscosity index, it is suitably used for rolling bearings for automotive electrical equipment auxiliary device, requiring a use environment of from a very low temperature to a high temperature. The aromatic ester oil is inexpensive and easily available.

As such a trimellitic acid ester, "TRIMEX T-08" and "TRIMEX N-08", all of which are manufactured by Kao Corporation; "ADEKA PROVER T-45", "ADEKA PROVER T-90" and "ADEKA PROVER PT-50", all of which are manufactured by Denka Corporation; "UNIQEMA EMKARATE 8130", "UNIQEMA EMKARATE 9130" and "UNIQEMA EMKARATE 1320"; and the like are available from the market. Moreover, as the pyromellitic acid ester, "ADEKA PROVER T-45", "ADEKA PROVER LX-1891" and "ADEKA PROVER LX-1892", all of which are manufactured by Denka Corporation; "BISOLUBETOPM", manufactured by Cognis; and the like are available from the market. These are low in a pour point and can be suitably used in the invention.

Diphenyl ether oils represented by following formulae are also preferable. By using such a diphenyl ether oil, it is possible to prepare a lubricant composition having excellent heat resistance and durability (for example, excellent lubricating properties can be kept over a long period of time even at a high temperature exceeding 160° C.). In particular, it can be suitably used in a site to be used at a high temperature and a high speed, such as components of automotive electrical equipment, automotive engine auxiliary devices, etc.

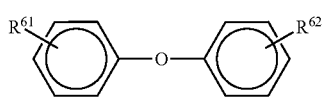

(XVII)

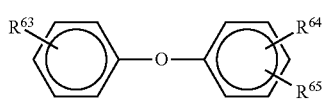

(XVIII)

In the foregoing formulae, $R^{61}$ and $R^{62}$ may be the same as or different from each other and each represents a linear or branched perfluoroalkyl group or a partial substitute thereof. The partial substitute of a perfluoroalkyl group as referred to herein means those in which a part of fluorine atoms or hydrogen atoms is substituted with a substituent such as a halogen atom such as a chlorine atom, a bromine atom, an iodine atom, etc., a hydroxyl group, a thiol group, an alkoxy group, an ether group, an amino group, a nitrile group, a nitro group, a sulfonyl group, a sulfinyl group, or a carbonyl-containing group such as an ester group, an amino group, an acyl group, an amide group, a carboxyl group, etc.; or the like, or having an ether structure in a part of the principal chain thereof.

Moreover, the carbon atom number in each of $R^{61}$ and $R^{62}$ is from 1 to 25, preferably from 1 to 10, and more preferably from 1 to 3. When the carbon atom number is more than 25, availability or synthesis of the raw material becomes difficult.

In addition, a (fluorine atom number)/(carbon atom number) ratio in each of $R^{61}$ and $R^{62}$ is from 0.6 to 3, preferably 1 to 3, and more preferably from 1.5 to 3.

In the foregoing formulae, one of $R^{63}$, $R^{64}$ and $R^{65}$ represents a hydrogen atom, and the remaining two represent the same or different branched alkyl group. Moreover, the carbon atom number is from 10 to 26, and preferably from 12 to 24. When the carbon atom number is less than 10, the amount of evaporation becomes large, whereas when it is more than 26, the fluidity at a low temperature is poor, resulting in a problem in the use. Specific examples thereof include a decyl group, an undecyl group, a dodecyl group, a tridecyl group, a tetradecyl group, a pentadecyl group, a hexadecyl group, a heptadecyl group, an octadecyl group, a nanodecyl group, an eicosyl group, etc. These may be branched.

The diphenyl ether oil represented by any of the foregoing formulae may be utilized in an amount of from 50 to 100% by mass and may be utilized in an amount of from 60 to 80% by mass in the oily medium. Within the foregoing range, the heat resistance is more improved. As an oil which is used jointly with the diphenyl ether oil, an ester based synthetic oil and a poly-α-olefin oil are preferable.

A material which is utilized as a base oil for traction oil can be utilized as the oily medium. The base oil for traction oil is usually selected among hydrocarbons. Hydrocarbons having a cyclic structure such as a cyclohexane ring, a decalin ring, a bicyclohepane ring, a bicyclooctane ring, etc. in a molecule thereof are preferable (see JP-A-2000-109871).

For example, examples of a saturated hydrocarbon compound having a cyclohexane ring include compounds disclosed in JP-B-3-80191, JP-B-2-52958, JP-B-6-39419, JP-B-6-92323, etc.; examples of a saturated hydrocarbon compound having a decalin ring include compounds disclosed in JP-B-60-43392 and JP-B-6-51874; and examples of a saturated hydrocarbon compound having a bicycloheptane ring include compounds disclosed in JP-B-5-31914, JP-B-7-103387, etc. More specifically, there are included 1-(1-decalyl)-2-cyclohexylpropane, 1-cyclohexyl-1-decalylethane, 1,3-dicyclohexyl-3-methylbutane, 2,4-dicyclohexylpentane; 1,2-bis(methylcyclohexyl)-2-methylpropane, 1,1-bis(methylcyclohexyl)-2-methylpropane and 2,4-dicyclohexyl-2-methylpentane. Moreover, examples of a saturated hydrocarbon compound having a bicyclooctane ring include compounds disclosed in JP-A-5-9134, etc.

An ionic liquid (ion liquid) has properties such as flame retardancy, nonvolatility, high polarity, high ion conductivity, high heat resistance, etc. In view of such properties, the ionic liquid is expected to be applied as a reaction solvent for green chemistry which is environmentally friendly or a next-generation electrolyte which is safe and high in performances. In the invention, the subject ionic liquid can be utilized as the oily medium. The ionic liquid (ion liquid) includes various kinds, and examples thereof include quaternary salts of a nitrogen-containing heterocyclic compound such as ammonium salts, choline salts, phosphoric acid salts, pyrazoline salts, pyrrolidine salts, imidazolium salts, pyridine salts, etc., sulfonium salts and the like.

As the oily medium which is used in the invention, petroleum hydrocarbons which are in general useful for the use as a fuel, for example, gasoline in the case of an internal combustion engine, etc. can be used. Such a fuel is typically a mixture of various kinds of hydrocarbons, and examples of components thereof include linear or branched paraffins and olefins, aromatic or naphthene based hydrocarbons and other liquid hydrocarbon based materials which are suitable for the use in a spark ignition gasoline engine.

Such a composition is supplied as every grade, for example, unleaded gasoline, leaded gasoline, etc., and typically, it is derived from a petroleum crude oil utilizing usual refining method and blending method, for example, straight fractional distillation, thermal cracking, hydrocracking, catalytic cracking and various modification methods. Gasoline will be defined as a liquid hydrocarbon or a mixture of hydrocarbon/oxygenate having an initial boiling point in the range of from about 20 to 60° C. and a final boiling point in the range of from about 150 to 230° C. when measured by the distillation method of ASTM D86. Examples of this oxygenate include alcohols such as methanol, ethanol, isopropanol, t-butanol, a $C_1$ to $C_5$ mixed alcohol, etc.; ethers such as methyl t-butyl ether, t-amyl ethyl ether, ethyl t-butyl ether, a mixed ether, etc.; and ketones such as acetone, etc.

In the invention, the above-exemplified oils may be used singly or in admixture of two or more different kinds thereof as the oily medium.

Moreover, there may be the case where the mineral oil is insufficient in wettability against a resin-made member, and from the viewpoint of lubricating properties or low friction properties against a resin-made member, or the like, it is preferable to use other oils than the mineral oil as the oily medium. Specifically, a polyolefin oil, a silicone oil, an ester oil, a polyglycol oil and a polyphenyl ether oil are preferable.

Moreover, there may be the case where the ester oil adversely influences a resin-made member or a rubber-made member, and from the viewpoint of preventing adverse influences against a resin-made member or a rubber-made member, it is preferable to use other oil than the ester oil. Specifically, a mineral oil, a polyolefin oil, a silicone oil, a polyglycol oil and a polyphenyl ether oil are preferable.

From the both viewpoints, polyolefins are preferable. Of these, a copolymer of ethylene and propylene; a copolymer of ethylene and an α-olefin having from 5 to 12 carbon atoms; and polybutene, polyisobutene or a polymer of an α-olefin having from 5 to 12 carbon atoms are more preferable, with a copolymer of ethylene and an α-olefin having from 5 to 12 carbon atoms and a polymer of an α-olefin having from 5 to 12 carbon atoms being further preferable.

3. Method for Preparing the Composition of the Invention:

The composition of the invention may be prepared by adding the complex alcohol ester composition to an oily medium or an aqueous medium and dissolved and/or dispersed therein. The dissolving and/or dispersing may be attained under heat. The amount of the complex alcohol ester composition to be added is preferably at least 10% by mass relative to the mass of the oily medium. However, the invention is not limited to the range, and so far as the above-mentioned compound is in an amount enough to exhibit the friction-reducing effect thereof, needless to say, the amount may be outside the above-mentioned range.

One embodiment of the composition of the invention is a composition that contains the compound represented by the formula (Z) of at least one oily medium selected from a mineral oil, a poly-α-olefin, a synthetic oil, a diphenyl ether oil, a fluorooil and a silicone oil, in an amount of at least 10% by mass.

The composition of the invention may contain, along with the complex alcohol ester composition and the oily medium or the aqueous medium therein, at least one additive within a range not detracting from the effect of the invention. Examples of the additive include a dispersant, a cleaning agent, an antioxidant, a carrier fluid, a metal inactivator, a dye, a marker, a corrosion inhibitor, a biocide, an antistatic additive, a drag reducer, an anti-emulsifying agent, an emulsifying agent, an antifoggant, an anti-freezing additive, an antiknock additive, an anti-valve seat recession additive, a lubricant additive, a surfactant, and a combustion enhancer. Various additives for use in lubricant, for example, in bearing oil, gear oil, power transmission oil or the like, or that is, an abrasion inhibitor, a viscosity index improver, a cleaning dispersant, a metal inactivator, a corrosion inhibitor, a defoaming agent and the like may be suitably added to the composition within a range not detracting from the object of the invention. These may be at least one selected from organic zinc compounds, molybdenum compounds, organic phosphorus compounds and organic sulfur compounds; and adding the compound of the type is favorable from the viewpoint of supplementing the antioxidative function of the organic zinc compound and of inhibiting abrasion under true boundary lubrication condition by the latter three.

Regarding some of the additives, specific examples will be described in details below.

Antiwear Agents:

Internal combustion engine lubricating oils require the presence of antiwear and/or extreme pressure (EP) additives in order to provide adequate antiwear protection for the engine. Increasingly demanding specifications for engine oil performance have required increasing antiwear properties of the oil. Antiwear and EP additives perform this role by reducing friction and wear of metal parts. While there are many different types of antiwear additives, for several decades the principal antiwear additive for internal combustion engine crankcase oils has been a metal alkylthiophosphate and more particularly a metal dialkyldithiophosphate in which the primary metal constituent is zinc, or zinc dialkyldithiophosphate (ZDDP). Typical examples of ZDDP compound include the compounds represented by the formula of $Zn[SP(S)(OR^{71})(OR^{72})]_2$ ($R^{71}$ and $R^{72}$ are $C_1$-$C_{18}$ alkyl groups, preferably $C_2$-$C_{12}$ alkyl groups). These alkyl groups may be straight chain or branched, and derived from primary and/or secondary alcohols and/or alkaryl groups such as alkyl phenol. The ZDDP generally is used in amounts of from about 0.4 to 1.4% by mass of the total composition, although the amount is not limited to the range.

However, it has been found that the phosphorus from these additives has a harmful effect on the catalyst in catalytic converters and also on oxygen sensors in automobiles. One example of the way for minimizing this effect is to replace some or all of the ZDDP with phosphorus-free antiwear additives. Accordingly, various non-phosphorous additives can be also used as antiwear agent. Sulfurized olefins are useful as antiwear or EP additives. Sulfur-containing olefins can be prepared by sulfurization of various organic materials such as aliphatic, arylaliphatic and alicyclic olefin hydrocarbons containing from about 3 to 30 carbon atoms, preferably from about 3 20 carbon atoms. The olefinic compounds contain at least one non-aromatic double bond. Such compounds are represented by the formula:

In the formula, $R^{73}$-$R^{76}$ each independently represent a hydrogen or a hydrocarbon group. Preferred hydrocarbon group is n alkyl or alkenyl group. Any two of $R^{73}$-$R^{76}$ may be connected so as to form a cyclic ring. Additional information concerning sulfurized olefins and their preparation can be found in U.S. Pat. No. 4,941,984, which can be referred.

The use of polysulfides of thiophosphorous acids and thiophosphorous acid esters as lubricant additives is disclosed in U.S. Pat. Nos. 2,443,264; 2,471,115; 2,526,497; and 2,591,577. Addition of phosphorothionyl disulfides as an antiwear, antioxidant, and EP additive is disclosed in U.S. Pat. No. 3,770,854. Use of alkylthiocarbamoyl compounds (bis(dibutyl)thiocarbamoyl, for example) in combination with a molybdenum compound (oxymolybdenum diisopropylphosphorodithioate sulfide, for example) and a phosphorous ester (dibutyl hydrogen phosphite, for example) as antiwear additives in lubricants is disclosed in U.S. Pat. No. 4,501,678. U.S. Pat. No. 4,758,362 discloses use of a carbamate additive to provide improved antiwear and extreme pressure properties. The use of thiocarbamate as an antiwear additive is disclosed in U.S. Pat. No. 5,693,598. Thiocarbamate/molybdenum complexes such as moly-sulfur alkyl dithiocarbamate trimer complex (R=$C_8$-$C_{12}$ alkyl) are also useful antiwear agents.

Glycerol esters may be used as antiwear agents. For example, mono-, di, and tri-oleates, mono-palmitates and mono-myristates may be used.

ZDDP may be combined with other antiwear agent(s). U.S. Pat. No. 5,034,141 discloses that a combination of a thiodixanthogen compound (such as octylthiodixanthogen) and a metal thiophosphate (such as ZDDP) can improve antiwear properties. U.S. Pat. No. 5,034,142 discloses that use of a metal alkyoxyalkylxanthate (such as nickel ethoxyethylxanthate) and a dixanthogen (such as diethoxyethyl dixanthogen) in combination with ZDDP improves antiwear properties.

Preferred antiwear additives include phosphorus and sulfur compounds such as zinc and sulfur compounds such as zinc dithiophosphates and/or sulfur, nitrogen, boron, molybdenum phosphorodithioates, molybdenum dithiocarbamates and various organo-molybdenum derivatives including heterocyclics (for example, dimercaptothiadiazoles, mercaptobenzothiadiazoles, triazines, and the like), alicyclics, amines, alcohols, esters, diols, triols, fatty amides and the like can also be used. Such additive may be used in amounts ranging from about 0.01 to 6% by mass, preferably about 0.01 to 4% by mass.

Viscosity Index Improver:

Viscosity index improvers (also known as VI improvers, viscosity modifiers, and viscosity improvers) provide lubricants with high and low-temperature operability. These additives impart favorable viscosity index number enhancement and shear stability at elevated temperatures and acceptable viscosity at low temperatures. Appropriate examples of the viscosity index improver include high-molecular weight hydrocarbons, polyesters, and viscosity index improvers capable of functioning not only as a viscosity index improver but also as a dispersant. The molecular weight of such a polymer is typically from about 10,000 to about 1,000,000, more typically from about 20,000 to about 500,000, and even more typically from about 50,000 to about 200,000.

Appropriate examples of the viscosity index improver include polymers and copolymers of methacrylate, butadiene, olefin or alkylated styrene. Polyisobutylenes are the typical viscosity index improvers. Other typical examples are polymethacrylates (for example, copolymers of any length alkyl methacrylate); and some of them function as a pour point depressant. Other typical examples are copolymers of ethylene and propylene, hydrogenated block-copolymers of styrene and isoprene, and polyacrylates (for example, copolymers of any length alkyl acrylate). Specific examples of them include styrene-butadiene polymers and styrene-isoprene polymers having a molecular-weight of from about 50,000 to about 200,000.

The viscosity index improver may be used in amounts ranging from about 0.01 to 8% by mass, preferably about 0.01 to 4% by mass.

Antioxidants:

Antioxidants have a function of retarding the oxidative degradation of oil(s) used in along with them. Such degradation may result in deposits on metal surfaces, the presence of sludge, or a viscosity increase in the lubricant. Various antioxidants which are useful in lubricant oil compositions are described, for example, "Klamann in Lubricants and Related Products" (Verlag Chemie (Deerfield Beach, Fla.), ISBN0-89573-177-0), and U.S. Pat. Nos. 4,798,684 and 5,084,197, which can be referred.

Useful antioxidants include hindered phenols. These phenolic antioxidants may be ashless (metal-free) phenolic compounds or neutral or basic metal salts of certain phenolic compounds. Typical phenolic antioxidants are hindered phenolics that contain a sterically hindered hydroxyl group, and these include those derivatives of dihydroxy aryl compounds in which the hydroxyl groups are in the o- or p-position to each other. Examples of the typical phenolic antioxidant include hindered phenols substituted with about $C_6$+alkyl groups and alkylene coupled derivatives of such hindered phenols. Examples of phenolic materials of this type include 2-t-butyl-4-heptyl phenol; 2-t-butyl-4-octyl phenol; 2-t-butyl-4-dodecyl phenol; 2,6-di-t-butyl-4-heptyl phenol; 2,6-di-t-butyl-4-dodecyl phenol; 2-methyl-6-t-butyl-4-heptyl phenol; and 2-methyl-6-t-butyl-4-dodecyl phenol. Other useful mono-phenolic antioxidants may include, for example, 2,6-di-alkyl-phenolic proprionic ester derivatives. Bis-phenolic antioxidants may also be advantageously used in combination with the invention. Examples of ortho coupled phenols include: 2,2'-bis(6-t-butyl-4-heptyl phenol); 2,2'-bis(6-t-butyl-4-octyl phenol); and 2,2'-bis(6-t-butyl-4-dodecyl phenol). Para coupled bis phenols include, for example, 4,4'-bis(2,6-di-t-butyl phenol) and 4,4'-methylene-bis(2,6-di-t-butyl phenol).

Non-phenolic oxidation inhibitors which may be used include aromatic amine antioxidants and these may be used either as such or in combination with phenolics. Typical examples of non-phenolic antioxidants include alkylated and non-alkylated aromatic amines such as aromatic monoamines represented by formula of $R^{78}R^{79}R^{80}N$ {in the formula, $R^{78}$ represents an aliphatic, aromatic or substituted aromatic group; $R^{79}$ represents an aromatic or a substituted aromatic group; and $R^{80}$ represents H, alkyl, aryl or $R^{81}S(O)_xR^{82}$ ((where $R^{81}$ represents an alkylene, alkenylene, or aralkylene group, $R^{82}$ represents a higher alkyl group, or an alkenyl, aryl, or alkaryl group, and x is 0, 1 or 2)}. The aliphatic group $R^{78}$ may contain from 1 to about 20 carbon atoms, and preferably contains from about 6 to 12 carbon atoms. The aliphatic group means a saturated aliphatic group. Preferably, both $R^{78}$ and $R^{79}$ are aromatic or substituted aromatic groups, and the aromatic group may be a condensed ring aromatic group such as naphthyl. Aromatic groups $R^{78}$ and $R^{79}$ may be joined together with other groups such as S.

Typical aromatic amines antioxidants may have alkyl substituent groups having at least about 6 carbon atoms. Examples of aliphatic groups include hexyl, heptyl, octyl, nonyl, and decyl. Generally, the aliphatic groups will not contain more than about 14 carbon atoms. The general types of amine antioxidants useful in the present compositions include diphenylamines, phenyl naphthyl-amines, phenothiazines, imidodibenzyls and diphenyl phenylene diamines. Mixtures of two or more aromatic amines are also useful. Polymeric amine antioxidants may also be used. Specific examples of aromatic amine antioxidants useful in the present invention include: p,p'-dioctyldiphenylamine; t-octylphenyl-alpha-naphthylamine; phenyl-alphanaphthylamine; and p-octylphenyl-alpha-naphthylamine.

Sulfurized alkyl phenols and alkali or alkaline earth metal salts thereof also are useful antioxidants. Low sulfur peroxide decomposers are useful as antioxidants.

Another class of antioxidant to be used in the composition of the invention is oil-soluble copper compounds. Any oil-soluble suitable copper compound may be blended into the lubricating oil. Examples of suitable copper antioxidants include copper dihydrocarbyl thio or dithio-phosphates and copper salts of carboxylic acid (naturally occurring or synthetic). Other suitable copper salts include copper dithiacarbamates, sulphonates, phenates, and acetylacetonates. Basic, neutral, or acidic copper Cu(I) and/or Cu(II) salts derived from alkenyl succinic acids or anhydrides are know to be particularly useful.

Preferable examples of the antioxidant include hindered phenols, arylamines, low sulfur peroxide decomposers and other related components. These antioxidants may be used individually by type or in combination with one another. Such additives may be used in amounts of from about 0.01 to 5% by mass, preferably from about 0.01 to 2% by mass, even more preferably from about 0.01 to 1% by mass.

Cleaning Agents:

Cleaning agents are commonly used in lubricant oil compositions. A typical cleaning agent is an anionic material containing a long chain lipophilic portion of the molecule and a smaller anionic or lipophobic portion of the molecule. The anionic portion of the cleaning agent is typically derived from an organic acid such as a sulfur acid, carboxylic acid, phosphorous acid, phenol, or mixtures thereof. The counter ion is typically an alkaline earth or alkali metal.

Salts that contain a substantially stoichiometric amount of the metal are described as neutral salts and have a total base number (TBN, as measured by ASTM D2896) of from 0 to 80. Many compositions are overbased, containing large amounts of a metal base that is achieved by reacting an excess of a metal compound (a metal hydroxide or oxide, for example) with an acidic gas (such as carbon dioxide). Useful cleaning agents can be neutral, mildly overbased, or highly overbased.

It is generally desirable for at least some parts of the cleaning agent to be overbased. Overbased cleaning agents help neutralize acidic impurities produced by the combustion process and become entrapped in the oil. Typically, the overbased material has a ratio of metallic ion to anionic portion of the cleaning agent of about 1.05:1 to 50:1 on an equivalent basis. More preferably, the ratio is from about 4:1 to about 25:1. The resulting cleaning agent is an overbased cleaning agent that will typically have a TBN of about 150 or higher, often about 250 to 450 or more. Preferably, the overbasing cation is sodium, calcium, or magnesium. A mixture of cleaning agents of differing TBN can be used in the present invention.

Preferable examples of the cleaning agent include the alkali or alkaline earth metal salts of sulfates, phenates, carboxylates, phosphates, and salicylates.

Sulfonates may be prepared from sulfonic acids that are typically obtained by sulfonation of alkyl substituted aromatic hydrocarbons. Examples of hydrocarbon include those obtained by alkylating benzene, toluene, xylene, naphthalene, biphenyl and their halogenated derivatives (chlorobenzene, chlorotoluene, and chloronaphthalene, for example). The alkylating agents typically have about 3 to 70 carbon atoms. The alkaryl sulfonates typically contain about 9 to about 80 carbon or more carbon atoms, more typically from about 16 to 60 carbon atoms.

Various overbased metal salts of various sulfonic acids which are useful as cleaning agents or dispersants in lubricant oils are disclosed. Various overbased sulfonates which are useful as cleaning agents or detergents are disclosed. They may be used in the invention.

Alkaline earth phenates are another useful class of cleaning agent. These cleaning agents may be prepared by reacting alkaline earth metal hydroxide or oxide (such as CaO, $Ca(OH)_2$, BaO, $Ba(OH)_2$, MgO, and $Mg(OH)_2$) with an alkyl phenol or sulfurized alkylphenol. Useful alkyl groups include straight chain or branched about $C_1$-$C_{30}$ alkyl groups, preferably about $C_4$-$C_{20}$ alkyl groups. Examples of suitable phenols include isobutylphenol, 2-ethylhexylphenol, nonylphenol, 1-ethyldecylphenol, and the like. It should be noted that starting material of alkylphenols may contain more than one alkyl substituent that are each independently straight chain or branched. When a non-sulfurized alkylphenol is used, the sulfurized product may be obtained by methods well known in the art. These methods include heating a mixture of alkylphenol and sulfurizing agent, including elemental sulfur or sulfur halides, such as sulfur dichloride and the like, and then reacting the sulfurized phenol with an alkaline earth metal base.

Metal salts of carboxylic acids are also useful as cleaning agents. These carboxylic acid cleaning agents may be prepared by reacting a basic metal compound with at least one carboxylic acid and removing free water from the reaction product. These compounds may be overbased to produce the desired TBN level. Cleaning agents made from salicylic acid are one preferred class of cleaning agents derived from carboxylic acids. Examples of the useful salicylate include long chain alkyl salicylates. One useful family of compositions is of the following formula.

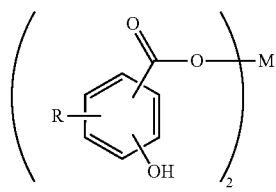

In the formula, R represents a hydrogen atom or an alkyl group having 1 to about 30 carbon atoms, n is an integer from 1 to 4, and M is an alkaline earth metal. Preferably, R is a $C_{11}$ or longer alkyl chain, and more preferably $C_{13}$ or longer alkyl chain. R may be an optionally substituted with substituents that do not interfere with the cleaning-agent's function. M is preferably, calcium, magnesium, or barium, and more preferably, calcium or magnesium. More preferably, M is calcium.

Hydrocarbyl-substituted salicylic acids may be prepared from phenols by the Kolbe reaction. See U.S. Pat. No. 3,595,791, incorporated herein by reference in its entirety, for additional information on synthesis of these compounds. The metal salts of the hydrocarbyl-substituted salicylic acids may be prepared by double decomposition of a metal salt in a polar solvent such as water or alcohol.

Alkaline earth metal phosphates are also used as cleaning agents.

Detergents may be simple cleaning agents or what is known as hybrid or complex cleaning agents. The latter cleaning agents can provide the properties of two cleaning agents without the need to blend separate materials. See, for example, U.S. Pat. No. 6,034,039, which can be referred. Preferable examples of the cleaning agent include calcium phenates, calcium sulfonates, calcium salicylates, magnesium phenates, magnesium sulfonates, magnesium salicylates and other related components (including borated cleaning agents). Typically the total cleaning agent concentration is from about 0.01 to 6% by mass, preferably from about 0.1 to 0.4% by mass.

Dispersants:

During engine operation, oil insoluble oxidation byproducts are produced. Dispersants help keep these byproducts in solution, thus diminishing their deposit on metal surfaces. Dispersants may be ashless or ash-forming in nature. Preferably, the dispersant is ashless. So called ashless dispersants are organic materials that form substantially no ash upon combustion. For example, non-metal-containing or borated metal-free dispersants are considered ashless. In contrast, metal-containing cleaning agents discussed above form ash upon combustion.

Suitable dispersants typically contain a polar group attached to a relatively high molecular weight hydrocarbon chain. The polar group typically contains at least one element of nitrogen, oxygen, or phosphorous. Typical hydrocarbon chains contain about 50 to 400 carbon atoms.

Examples of the dispersant include phenates, sulfonates, sulfurized phenates, salicylates, naphthenates, stearates, carbamates, thiocarbamates, and phosphorus derivatives. A particularly useful examples of the dispersant include alkenyl-succinic derivatives, typically produced by the reaction of a long chain substituted alkenyl succinic compound, usually a substituted succinic anhydride, with a polyhydroxy or polyamino compound. The long chain group constituting the lipophilic portion of the molecule which adds solubility in the oil, is normally a polyisobutylene group. Many examples of this type of dispersant are well known commercially or in various documents. Exemplary U.S. Patents describing such dispersants include U.S. Pat. Nos. 3,172,892; 3,2145,707; 3,219,666; 3,316,177; 3,341,542; 3,444,170; 3,454,607; 3,541,012; 3,630,904; 3,632,511; 3,787,374 and 4,234,435. Other types of dispersants are described in U.S. Pat. Nos. 3,036,003; 3,200,107; 3,254,025; 3,275,554; 3,438,757; 3,454,555; 3,565,804; 3,413,347; 3,697,574; 3,725,277; 3,725,480; 3,726,882; 4,454,059; 3,329,658; 3,449,250; 3,519,565; 3,666,730; 3,687,849; 3,702,300; 4,100,082; 5,705,458. A further description of dispersants is also found in European Patent Application No. 471071.

Hydrocarbyl-substituted succinic acid compounds are well known dispersants. In particular, succinimide, succinate esters, or succinate ester amides prepared by the reaction of hydrocarbon-substituted succinic acid preferably having at least 50 carbon atoms in the hydrocarbon substituent, with at least one equivalent of an alkylene amine, are particularly useful.

Succinimides are formed by the condensation reaction between alkenyl succinic anhydrides and amines. Molar ratios can vary depending on the polyamine. For example, the molar ratio of alkenyl succinic anhydride to TEPA can vary from about 1:1 to about 5:1. Representative examples are shown in U.S. Pat. Nos. 3,087,936; 3,172,892; 3,219,666; 3,272,746; 3,322,670; 3,652,616; 3,948,800; and Canada Pat. No. 1,094,044.

Succinate esters are formed by the condensation reaction between alkenyl succinic anhydrides and alcohols or polyols. Molar ratios can vary depending on the alcohol or polyol used. For example, the condensation product of an alkenyl succinic anhydride and pentaerythritol is a useful dispersant.

Succinate ester amides are formed by condensation reaction between alkenyl succinic anhydrides and alkanol amines. For example, suitable alkanol amines include ethoxylated polyalkylpolyamines, propoxylated polyalkylpoly-amines and polyalkenylpolyamines such as polyethylene polyamines. One example is propoxylated hexamethylenediamine. Representative examples are shown in U.S. Pat. No. 4,426,305.

The molecular weight of the alkenyl succinic anhydrides used in the preceding paragraphs will range between about 800 and 2,500. The above products can be post-reacted with various reagents such as sulfur, oxygen, formaldehyde, carboxylic acids such as oleic acid, and boron compounds such as borate esters or highly borated dispersants. The dispersants can be borated with from about 0.1 to about 5 moles of boron per mole of dispersant reaction product, including those derived from mono-succinimides, bis-succinimides (also known as disuccinimides), and mixtures thereof.

Mannich base dispersants are made from the reaction of alkylphenols, formaldehyde, and amines. See U.S. Pat. No. 4,767,551, incorporated by reference herein in its entirety. Process aids and catalysts, such as oleic acid and sulfonic acids, can also be part of the reaction mixture. Molecular weights of the alkylphenols range from 800 to 2,500. Representative examples are shown in U.S. Pat. Nos. 3,697,574; 3,703,536; 3,704,308; 3,751,365; 3,756,953; 3,798,165; and 3,803,039.

Typical high molecular weight aliphatic acid modified Mannich condensation products useful in this invention can be prepared from high molecular weight alkyl-substituted hydroxyaromatics or $HN(R)_2$ group-containing reactants.

Examples of high molecular weight alkyl-substituted hydroxyaromatic compounds are polypropylphenol, polybutylphenol, and other polyalkylphenols. These polyalkylphenols can be obtained by the alkylation, in the presence of an alkylating catalyst, such as $BF_3$, of phenol with high molecular weight polypropylene, polybutylene, and other polyalkylene compounds to give alkyl substituents on the benzene ring of phenol having an average 600-100,000 molecular weight.

Examples of $HN(R)_2$ group-containing reactants are alkylene polyamines, principally polyethylene polyamines. Other representative organic compounds containing at least one $HN(R)_2$ group suitable for use in the preparation of Mannich condensation products are well known and include mono- and di-amino alkanes and their substituted analogs, e.g., ethylamine and diethanol amine; aromatic diamines, e.g., phenylene diamine, diamino naphthalenes; heterocyclic amines, e.g., morpholine, pyrrole, pyrrolidine, imidazole, imidazolidine, and piperidine; melamine and their substituted analogs.

Examples of alkylene polyamide reactants include ethylenediamine, diethylene triamine, triethylene tetraamine, tetraethylene pentaamine, pentaethylene hexamine, hexaethylene heptaamine, heptaethylene octaamine, octaethylene nonaamine, nonaethylene decamine, decaethylene undecamine, and mixtures of such amines. Some preferred compositions correspond to formula $H_2N-(Z-NH-)_nH$, where Z is a divalent ethylene and n is 1 to 10 of the foregoing formula. Corresponding propylene polyamines such as propylene diamine and di-, tri-, tetra-, pentapropylene tri-, tetra-, penta- and hexaamines are also suitable reactants. Alkylene polyamines usually are obtained by the reaction of ammonia and dihalo alkanes, such as dichloro alkanes. Thus, the alkylene polyamines obtained from the reaction of 2 to 11 moles of ammonia with 1 to 10 moles of dichloro alkanes having 2 to 6 carbon atoms and the chlorines on different carbons are suitable alkylene polyamine reactants.

Aldehyde reactants useful in the preparation of the high molecular products useful in this invention include aliphatic aldehydes such as formaldehyde (such as paraformaldehyde and formalin), acetaldehyde and aldol (b-hydroxybutyraldehyde, for example). Formaldehyde or a formaldehyde-yielding reactant is preferred.

Hydrocarbyl substituted amine ashless dispersant additives are well known to those skilled in the art. See, for example, U.S. Pat. Nos. 3,275,554; 3,438,757; 3,565,804; 3,755,433, 3,822,209, and 5,084,197, which can be referred.

Preferable examples of the dispersant include borated and non-borated succinimides, including those derivatives from mono-succinimides, bis-succinimides, and/or mixtures of mono- and bis-succinimides, wherein the hydrocarbyl succinimide is derived from a hydrocarbylene group such as polyisobutylene having a Mn of from about 500 to about 5000, preferably from about 1000 to about 3000, more preferably from about 1000 to about 2000, even more preferably from about 1000 to about 1600, or a mixture of such hydrocarbylene groups. Other preferable examples of the dispersant include succinic acid-esters and amides, alkylphenol-polyamine coupled Mannich adducts, their capped derivatives, and other related components. Such additives may be used in an amount of about 0.1 to 20% by mass, preferably about 0.1 to 8% by mass.

Pour Point Depressants:

Pour point depressants have a function of lowering the minimum temperature at which the fluid will flow or can be poured. Examples of the suitable pour point depressant include polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. U.S. Pat. Nos. 1,815,022; 2,015,748; 2,191,498; 2,387,501; 2,655, 479; 2,666,746; 2,721,877; 2.721,878; and 3,250,715 describe useful pour point depressants and/or the preparation thereof. Such additives may be used in an amount of about 0.01 to 5% by mass, preferably about 0.01 to 1.5% by mass.

Corrosion Inhibitors:

Corrosion inhibitors are used to reduce the degradation of metallic parts to contact with the lubricating oil composition. Examples of the suitable corrosion inhibitor include thiadiazoles. See, for example, U.S. Pat. Nos. 2,719,125; 2,719,126; and 3,087,932, which can be referred. Such additives may be used in an amount of about 0.01 to 5% by mass, preferably about 0.01 to 1.5% by mass.

Seal Compatibility Additives:

Seal compatibility agents help to swell elastomeric seals by bringing about chemical reactions in fluids or physical changes in elastomers. Examples of the suitable seal compatibility agent include organic phosphates, aromatic esters, aromatic hydrocarbons, esters (such as butylbenzyl phthalate), and polybutenyl succinic anhydride. Such additives may be used in an amount of about 0.01 to 3% by mass, preferably about 0.01 to 2% by mass.

Anti-Foam Agents:

Anti-foam agents retard the formation of stable foams. Silicones and organic polymers are typical anti-foam agents. For example, polysiloxanes, such as silicon oil or polydimethyl siloxane, provide antifoam properties. Anti-foam agents are commercially available and may be used in conventional minor amounts along with other additives such as demulsifiers; usually the amount of these additives combined is less than 1 percent and often less than 0.1%.

Antirust Additives (or Corrosion Inhibitors):

Antirust additives (or corrosion inhibitors) are additives that protect lubricated metal surfaces against chemical attack by water or other contaminants. Various antirust additives are commercially available.

They are referred to also in Klamann in "Lubricants and Related Products" (Verlag Chemie (Deerfield Beach, Fla.), ISBN0-89573-177-0).

One type of antirust additive is a polar compound that wets the metal surface preferentially, protecting it with a film of oil. Another type of antirust additive absorbs water by incorporating it in a water-in-oil emulsion so that only the oil touches the metal surface. Yet another type of antirust additive chemically adheres to the metal to produce a non-reactive surface. Examples of suitable additives include zinc dithiophosphates, metal phenolates, basic metal sulfonates, fatty acids and amines. Such additives may be used in an amount of about 0.01 to 5% by mass, preferably about 0.01 to 1.5% by mass.

Friction Modifiers:

A friction modifier is any material or materials that can alter the coefficient of friction of any lubricant or fluid containing such material(s). Friction modifiers, also known as friction reducers, or lubricity agents or oiliness agents, and other such agents that change the coefficient of friction of lubricant base oils, formulated lubricant compositions, or functional fluids, may be effectively used in combination with the base oils or lubricant compositions of the present invention if desired. Friction modifiers that lower the coefficient of friction are particularly advantageous in combination with the base oils and lube compositions of this invention. Friction modifiers may include metal-containing compounds or materials as well as ashless compounds or materials, or mixtures thereof. Metal-containing friction modifiers may include metal salts or metal-ligand complexes where the metals may include alkali, alkaline earth, or transition group metals. Such metal-containing friction modifiers may also have low-ash characteristics. Transition metals may include Mo, Sb, Sn, Fe, Cu, Zn, and others. Ligands may include hydrocarbyl derivative of alcohols, polyols, glycerols, partial ester glycerols, thiols, carboxylates, carbamates, thiocarbamates, dithiocarbamates, phosphates, thiophosphates, dithiophosphates, amides, imides, amines, thiazoles, thiadiazoles, dithiazoles, diazoles, triazoles, and other polar molecular functional groups containing effective amounts of O, N, S, or P, individually or in combination. In particular, Mo-containing compounds can be particularly effective such as for example Mo-dithiocarbamates (Mo(DTC)), Mo-dithiophosphates (Mo(DTP)), Mo-amines (Mo (Am)), Mo-alcoholates, Mo-alcohol-amides, etc.

Ashless friction modifiers may also include lubricant materials that contain effective amounts of polar groups, for example hydroxyl-containing hydrocarbyl base oils, glycerides, partial glycerides, glyceride derivatives, and the like. Polar groups in friction modifiers may include hyrdocarbyl hydrocarbyl groups containing effective amounts of O, N, S, or P, individually or in combination. Other friction modifiers that may be particularly effective include, for example, salts (both ash-containing and ashless derivatives) of fatty acids, fatty alcohols, fatty amides, fatty esters, hydroxyl-containing carboxylates, and comparable synthetic long-chain hydrocarbyl acids, alcohols, amides, esters, hydroxy carboxylates, and the like. In some instances fatty organic acids, fatty amines, and sulfurized fatty acids may be used as suitable friction modifiers.

Useful concentrations of friction modifiers may range from about 0.01% by mass to 15% by mass, often with a preferred range of about 0.1% by mass to 5% by mass. Concentrations of molybdenum containing materials are often described in terms of Mo metal concentration. Advantageous concentrations of Mo may range from about 10 ppm to 3000 ppm or more, and often with a preferred range of about 20 to 2000 ppm, and in some instances a more preferred range of about 30 to 1000 ppm. Friction modifiers of all types may be used alone or in mixtures with the materials of this invention. Often mixtures of two or more friction modifiers, or mixtures of friction modifiers(s) with alternate surface active material(s), are also desirable.

Additives of Grease Composition:

The composition of the invention may be prepared as a grease composition. In the subject embodiment, in order to ensure a practical performance in the case of adapting to a grease application, a thickener or the like may be properly added within the range where the object of the invention is not impaired, as the need arises. One embodiment of the grease composition is a composition containing the compound represented by formula (Z) described above in an amount of from about 50 to 90% by mass and a thickener in an amount of from 10 to 50% by mass. Additives which can be added during the preparation of a grease composition are hereunder described.

As the thickener which can be added, all of thickeners such as soap based thickeners, for example, a metal soap, a composite metal soap, etc.; non-soap based thickeners such as Bentone, silica gel, urea based thickeners (urea compounds, urea/urethane compounds, urethane compounds, etc.); and the like can be used. Of these, soap based thickeners and urea based thickeners are preferably used because they are less likely to damage resin-made members.

Examples of the soap based thickener include a sodium soap, a calcium soap, an aluminum soap, a lithium soap, etc. Of these, a lithium soap is preferable in view of excellent waterproof properties and thermal stability. Examples of the lithium soap include lithium stearate, lithium 12-hydroxystearate, etc.

Moreover, examples of the urea based thickener include urea compounds, urea/urethane compounds, urethane compounds, mixtures of these compounds, etc.

Examples of the urea compound, urea/urethane compound and urethane compound include diurea compounds, triurea compounds, tetraurea compounds, polyurea compounds (excluding diurea compounds, triurea compounds and tetraurea compounds), urea/urethane compounds, diurethane compounds, mixtures of these compounds, etc. Preferably, diurea compounds, urea/urethane compounds, diurethane compounds and mixtures of these compounds are exemplified.

Examples of the solid lubricant include polytetrafluoroethylene, boron nitride, fullerene, graphite, fluorinated graphite, melamine cyanurate, molybdenum disulfide, Mo-dithiocarbamate, antimony sulfide, borates of an alkali (alkaline earth) metal, etc.

Examples of the wax include various waxes including natural waxes and mineral oil based or synthetic waxes. Specific examples thereof include a montan wax, a carnauba wax, an amide compound of a higher fatty acid, a paraffin wax, a microcrystalline wax, a polyethylene wax, a polyolefin wax, an ester wax, etc.

Besides, benzotriazole, benzimidazole, thiadiazole and the like are known as the metal deactivator, and these can be used.

A viscosity improver can be added to the foregoing grease composition. Examples of the viscosity improver include polymethacrylate, polyisobutylene, polystyrene, etc. Poly(meth)acrylate is also known to have an effect of preventing an abnormal sound at a low temperature in a cold district.

In general, a rotary bearing portion of a food-making machine adopts a prelubricated rolling bearing or the like. However, since there may be a possibility that such a mineral oil based grease composition is scattered and brought into contact with foods during the operation of the machine, it may not be said that such is suitable in view of the food hygiene. Moreover, there is a concern that the grease is polluted by bacteria, so that it may be likely considered that there is a possibility that the foods are adversely affected. As a grease composition capable of solving such a problem, there are known a grease composition containing antibacterial zeolite as an antibacterial agent and so forth. Moreover, a natural antibacterial agent is preferable in view of safety. Specifically, chitosans, catechins, Moso bamboo, mustard, an essential oil of wasabi and the like are representative. Besides, antibacterial substances such as colloidal pectin abundant in apple, grape and citrus fruits; polylysin which is a straight-chain polymer of L-lysine as an essential amino acid; protamine which is a basic protein contained in matured testis of salmon, trout, herring and the like; extracts of seed and fruit of *Psoralea corylifolia*; spices obtained by dried leaves of Lamiaceae such as rosemary, sage, thyme and so forth; extracts of *Coix lacryma-jobi* obtained by using a hydrophobic organic solvent; extracts of root and stem of *Cirsium brevicaule*; propolis obtained from honeycomb; and the like can be used.

Of these, catechins which are largely effective against various types of food poisoning are suitable. Above all, epigallocatechin, epicatechin, epicatechin gallate, epigallocatechin gallate, catechin and so forth, which are a water-soluble component contained in tea leaves, are preferable. In general, since such catechins are soluble in water, they are preferably used upon being added with a small amount of a surfactant. However, in the case of a grease composition, there is no need of further adding a surfactant because the thickener also plays a role as the surfactant.

Moreover, the grease composition is also highly adaptable to a rubber to be disposed in the vicinity of a sliding portion. Though such a rubber is not particularly limited, specific examples thereof include a nitrile rubber, a chloroprene rubber, a fluorinated rubber, an ethylene/propylene rubber, an acrylic rubber and composites of these materials.

Static electricity generated in rolling bearings is known to adversely affect, by a radiated noise thereof, a copied image produced by a copying machine, such as distortion, etc., and the copresence of a conductive material is effective for its suppression. The conductive material is added in an amount of from 2 to 10% by mass of the total amount of the grease. Of the conductive materials, carbon black and graphite are suitable, and the both can be used independently or in admixture. In the case of using them as a mixture, the total content is regulated to the foregoing addition amount. Moreover, each of carbon black and graphite is preferably one having an average particle size of from 10 to 300 nm.

Moreover, the conductive material is also known to be effective as an anti-separation agent as described in the section relevant to the extreme pressure agent. As described in JP-A-2002-195277, this conductive material has an effect of suppressing whitening and separation to be caused by a hydrogen ion.

There are also known techniques of adding a hollow filler or a silica particle for the purpose of improving heat-insulating properties of the grease, or conversely, techniques of adding a powder of metal such as copper, etc. for the purpose of promoting heat conduction and heat radiation properties.

As the grease with improved flame retardancy, there are known those obtained by adding a powder of an oxide, a carbonate or the like of an alkali metal or alkaline earth metal to a lithium soap grease, those obtained by adding calcium carbonate and a platinum compound to a silicone grease, and those obtained by allowing a grease to contain a water-absorptive polymer and water.

4. Properties of Composition of the Invention:

4-1. Viscosity:

A viscosity at 40 degrees Celsius of the composition of the invention is preferably equal to or less than 1000 mPa·s, more preferably equal to or less than 500 mPa·s, or even more preferably not equal to or less than 200 mPa·s. The smaller the viscosity, the more preferable the composition is because it contributes to low fuel consumption. However, since the viscosity of the composition of the invention largely varies with a viscosity of the base oil to be used, a structure and an addition amount of the compound of the invention and coexistent additives, and an adequate viscosity is required depending upon the use environment, the viscosity of the composition of the invention must be made in conformity therewith. However, since the invention is not required to suppress the lowering in viscosity of a base oil at a high temperature to be caused due to a viscosity index improver in the current technologies, it is free from the occurrence of an increase in viscosity at a low temperature to be caused due to the addition of a viscosity index improver. Thus, it is also one of characteristic features that the effect of the low-viscosity base oil contributes directly to the fuel consumption.

4-2. Elementary Formulation:

As for the composition of the invention, it is preferable that the constituent elements are composed of only carbon, hydrogen, oxygen and nitrogen; and it is more preferable that the constituent elements are composed of only carbon, hydrogen and oxygen. Moreover, as for the oil to be used for the oily medium, there are various materials composed of only carbon, hydrogen and oxygen. By combining them, a composition in which the constituent elements are composed of only carbon, hydrogen, oxygen and nitrogen can be prepared. In general, the current lubricating oils contain phosphorus, sulfur and a heavy metal. In a lubricating oil to be used for a 2-stroke engine of combusting the lubricating oil together with a fuel, though it does not contain phosphorus and a heavy metal while taking into consideration the environmental load, it contains sulfur in an amount of about a half of a lubricating oil to be used for a 4-stroke engine. That is, in the current lubricating technologies, though it may be conjectured that the formation of a boundary lubricating film made of sulfur is essential at a minimum. In view of the fact that a sulfur element is contained, a load to a catalyst for exhaust gas cleaning is very large. In this catalyst for exhaust gas cleaning, though platinum and nickel are used, a poisoning action of phosphorus or sulfur is a serious problem. From this point of issue, a merit to be brought due to the fact that elements constituting a composition of the lubricating oil are composed of only carbon, hydrogen, oxygen and nitrogen is very large. In addition, the fact that the composition is composed of only carbon, hydrogen and oxygen is optimal for lubricating oils of industrial machines, in particular food manufacturing-related devices. According to the current technology, an elementary composition taking into consideration the environment while scarifying the coefficient of friction is adopted. This is also a very preferable technology for a lubricating oil for cutting or working a metal requiring a large amount of water for cooling. In many cases, the lubricating oil inevitably floats or vaporizes in the air as a mist, and a treatment waste fluid is discharged into the natural system. Therefore, in order to make both the lubricating properties and the environmental protection compatible with each other, it is very preferable to substitute the current lubricating oils with the composition of the invention which is constituted of only carbon, hydrogen and oxygen.

5. Applications of Composition of the Invention:

The composition of the invention is useful as a lubricating oil. For example, the composition of the invention is fed between the two sliding surfaces and can be used for reducing the friction. The composition of the invention is able to form a film on the sliding surface. As for the material quality of the sliding surface, specific examples of steel include carbon steels for machine structural use; alloy steels for machine structural use such as a nickel-chromium steel material, a nickel-chromium-molybdenum steel material, a chromium steel material, a chromium-molybdenum steel material, an aluminum-chromium-molybdenum steel material, etc.; stainless steel, and maraging steel.

Various metals other than steel, or inorganic or organic materials other than metals are widely used.

Examples of the inorganic or organic materials other than metals include various plastics, ceramics, carbon, etc. and mixtures of these materials, etc. More specific examples of the metal materials other than steel include cast iron, a copper/copper-lead/aluminum alloy, castings of these materials and white metal.

Examples of the organic material include all of general plastics, engineering plastics, such as high-density polyethylenes (HDPE), polyamides, polyacetals (POM), polycarbonates, polyethylene terephthalates, polybutylene terephthalates, polybutylene naphthalates, polyphenylene ethers, poly phenylene Sulfides (PPS), fluorine resins. Tetrafluoroethylene resins (PFPE), polyarylates, polyamide imides (PAI), polyether imides, polypyromellitimides, polyether ether ketones (PEEK), polysulfones, polyethersulfones, polyimides (PI), polystyrenes, polyethylenes, polypropylenes, phenol resins, AS resins, ABS resins, AES resins, AAS resins, ACS resins, MBS resins, polyvinyl chloride resins, epoxy resins, diallyl phthalate resins, polyester resins, methacryl resins, and ABS/polycarbonate alloy.

Such a resin forms a molding or a resin layer as various components or members, and this grease composition is applied in a portion where it comes into contact with other resin or metal. Specifically, the grease composition is effectively applied to, for example, a sliding portion, a bearing and a resin gear part of automotive electrical equipment represented by an electric power steering, a door mirror and so forth; a resin gear part for audio instruments such as a radio cassette recorder, VTR, a CD player and so forth; a resin gear unit for office automation equipment such as a printer represented by a laser printer, a copying machine, a facsimile and so forth; and a contact portion between a resin material for forming a sliding part of every automotive actuator and an air cylinder interior, with other resin material or a metal material.

Examples of the inorganic material include ceramics such as silicon carbide, silicon nitride, alumina, zirconia, titanium carbide (TiC), zirconium carbide (ZrC), titanium nitride (TiN), etc.; and carbon materials. Moreover, examples of a mixture of these materials include organic-inorganic composite materials in which a plastic is composited with fibers of glass, carbon, aramid, etc., cermet which is a composite material of a ceramic and a metal and so forth.

In the case where a part is composed of a material other than steel, at least a part of the surface of a steel material is covered by a film composed of a metal material other than steel or an organic or inorganic material other than metal materials. Examples of the covering film include magnetic material thin films such as a thin film made of diamond-like carbon and organic or inorganic porous films.

Moreover, the configuration may be achieved in such a manner that a porous sintered layer is formed on at least one of the foregoing two surfaces, and the porous layer is impregnated with the composition of the invention, thereby allowing the lubricant composition to be properly fed onto the sliding surface at the time of sliding. The foregoing porous film may be composed of any material selected among metal materials, organic materials and inorganic materials. Specific examples thereof include sintered metals; porous ceramics formed by allowing fine particles of calcium zirconate. ($CaZrO_3$) and magnesia (MgO) to strongly bond to each other; porous glasses obtained by allowing silica and a borate based component to thermally cause phase separation; sintered porous moldings of an ultra-high-molecular weight polyethylene powder; fluorocarbon resin based porous films made of polytetrafluoroethylene, etc.; polysulfone based porous films to be used for a microfilter, etc.; porous films formed by previously allowing a poor solvent of a molding and a monomer for forming the molding to cause phase separation at the time of polymerization; and so forth.

Examples of the metal or metal oxide sintered layer include porous layers formed by sintering a copper based, iron based or $TiO_2$ based powder. The copper based sintered layer can be formed by placing a mixture of a copper powder (for example, 88% by mass), tin (for example, 10% by mass) and graphite (for example, 2% by mass) on a cast iron substrate, compress molding the resultant under 250 MPa and sintering the molding in a reductive gas stream at a high temperature, for example, about 770 degrees Celsius for about one hour. Moreover, the iron based sintered layer can be formed by placing a mixture of an iron powder having a copper powder (for example, 3% by mass) and chemical carbon (0.6% by mass) added thereto on a cast iron substrate, compress molding the resultant under 250 MPa and sintering the molding in a reductive gas stream at a high temperature, for example, about 770 degrees Celsius for about one hour. Moreover, the $TiO_2$ sintered layer is formed by placing a mixture of $Ti(OC_8H_{17}\text{-n})$ (for example, 33% by mass), a fine powder of $TiO_2$ (for example, 57% by mass) and PEO (molecular weight MW=3,000) on a cast iron substrate and sintering the resultant under heating at 560 degrees Celsius for 3 hours while irradiating UV rays.

In this connection, the material to be covered by such a porous layer is not specifically limited, and it may be any of the foregoing ceramics, resins and organic-inorganic composite materials or, as a matter of course, may be steel.

The coating film made of the foregoing magnetic material thin film such as a diamond-like carbon thin film, etc. can be formed by a surface treatment. Details of the surface treatment are described in *Tribology Handbook*, 1st edition (2001), Series B, Chapter 3, "Surface Treatment", pages 544 to 574, edited by Japanese Society of Tribologists, all contents of which are adoptable to manufacturing of the mechanical elements of the invention. In general, the surface treatment is achieved for the purpose of improving tribological characteristics through surface modification, wherein the operation of mechanical elements often requires not only low friction and wear resistance but various material characteristics such as low noise, corrosion resistance, chemical stability, heat resistance, dimensional stability, low out-gas, biocompatibility, antibacterial performance and so forth, depending on demands of the operational environment. In consequence, in the invention, the surface treatment is not limited to those aimed at improving the tribological characteristics. Examples of the surface treatment include:

1) formation of a film of aluminum, copper, silver, gold, chromium, molybdenum, tantalum or alloys thereof; a ceramic film of titanium nitride, chromium nitride, titanium carbide, chromium carbide, etc.; and an oxide film of aluminum oxide, silicon dioxide, molybdenum silicide, tantalum oxide, barium titanate, etc., by a physical vapor deposition method by vacuum vapor evaporation, ion plating, sputtering or ion implantation;

2) formation of a film of every metal; a carbide film of WC, TiC, $B_4C$; a nitride film of TiN, $Si_3N_4$, etc.; a boride film of $TiB_2$, $W_2B_3$, etc.; an oxide film of $Al_2O_3$, $ZrO_2$, etc.; an amorphous carbon film containing CrW or a Ti metal; a fluorine-containing carbon film; or a plasma-polymerized polymer, by a chemical vapor deposition method by heat, plasma, light, etc.;

3) a method of imparting characteristics such as wear resistance, anti-seize properties and so forth to a surface layer portion, by a diffusive covering method (chemical reaction process) such as carburization, nitriding, sulfurizing and boronization treatments and so forth; and 4) formation of a film of a metal, a composite metal, etc., by a plating method such as electro-plating, electroless plating and so forth.

The composition of the invention can be utilized for various applications. For example, the composition of the invention is used for fuels for combustion engine, engine oils for internal combustion engine, cutting oils, engine oils for vehicles including automobiles, etc., gear oils, hydraulic oils for automobiles, lubricating oils for marine vessel and aircraft, machine oils, turbine oils, bearing oils, hydraulic oils, oils for compressor and vacuum pump, freezer oils, lubricating oils for cooling apparatuses such as air conditioners or refrigerators having a reciprocating or rotary sealing type compressor, automotive air conditioners dehumidifiers, freezers, refrigerated warehouses, vending machines, showcases, chemical plants, etc, and so forth.

Moreover, the composition of the invention is also useful as a chlorine based compound-free lubricating oil for metal working during working of hot rolling or cutting a metal material, for example, steel materials, Al alloys, etc.; as a metal working oil or plastic working oil such as a cold rolling oil, a cutting oil, a grinding oil, a drawing oil, a press working oil, etc. of aluminum, in particular, as an inhibitor of wear, breakage or surface roughening at the time of high-speed and high-load working; and as a metal working oil composition which can be applied to low-speed and heavy cutting such as brooch working or gun drill working.

Moreover, the composition of the invention can be utilized for various lubricating oils for grease, lubricants for magnetic recording medium, lubricants for micromachine, lubricants for artificial bone and so forth. Moreover, since the elementary composition of the composition can be made of a carbohydrate, by using, as a lubricating oil, a composition containing a cooking oil as a base oil and containing a sorbitan fatty acid ester containing polyoxyethylene ether which is widely used as an emulsifier, a dispersant or a solubilizing agent for cake mixtures, salad dressings, shortening oils, chocolates, etc., a high-performance lubricating oil which is utterly harmless to man can be used for lubrication of members of manufacturing equipment of food-manufacturing line or medical equipment.

Moreover, by emulsifying and dispersing the composition of the invention in a water system or dispersing it in a polar solvent or a resin medium, it can be used as a cutting oil or a rolling oil.

Moreover, the composition of the invention can be utilized as a mold release agent for various applications. For example, the composition of the invention can be used as a mold release agent for polycarbonate resins, flame-retardant polycarbonate resins, crystalline polyester resins which are a main component for image forming toners to be used for electrophotographic apparatus or electrostatic recording, apparatus, various thermoplastic resin compositions for molding, semi-conductor sealing epoxy resin compositions and so forth. One embodiment of the mold release agent is an embodiment containing the complex alcohol ester composition in an amount of from 0.01 to 10% by mass (preferably from 0.1 to 5% by mass).

Moreover, by previously kneading the composition of the invention into textile goods such as clothing, etc. or coating it, it can also be used as an antifouling agent for promoting release of a stain deposited on the textile goods, thereby preventing the stain of the fiber goods.

EXAMPLES

The invention is described more concretely with reference to the following Examples. In the following Examples, the material used, its amount and ratio, the details of the treatment and the treatment process may be suitably modified or changed not overstepping the sprit and the scope of the invention. Accordingly, the invention should not be limitatively interpreted by the Examples mentioned below.

1. Test Example 1

Production of Complex Alcohol Ester Composition and Evaluation of Lubricity (Friction Coefficient) of the Composition Production Examples of the complex alcohol ester composition of the invention are shown below. The physical properties of the composition were measured as mentioned below.

(1) Composition Distribution:

According to gel permeation chromatography (GPC, Tosoh's trade name, HLC-8020/4 columns, Tosoh's trade names, TSKguard column Super HZ-H, TSKgel Super HZM-H, TSKgel Super HZ4000, TSKgel Super HZ2000), a tetrahydrofuran (THF) solvent was used, and GPC charts were obtained. The calibration curve was formed from the standard sample of polystyrene, and if desired, the equivalent molecular weight of the sample (number-average molecular weight=Mn, weight-average molecular weight=Mw) was obtained.

(2) Molecular Structure:

Using a superconductive nuclear magnetic resonance absorption apparatus (NMR, Bruker's trade name, AVANCE 400), $^1$H-NMR or $^{13}$C-NMR was determined in heavy chloroform, and the NMR chart was obtained.

(3) Friction Coefficient:

Using an oscillation-type frictional wear tester (Optimol Instruments Prueftechnik GmbH's trade name, SRV 4), a sample was applied between a columnar upper test piece (made of SUJ-2, φ15×22 mm) and a disc-like lower test piece (made of SUJ-2, φ24×7 mm). At an amplitude of 1.5 mm and a frequency of 50 Hz, the load, the temperature and the time were varied from 50 N, 25 degrees Celsius, 1 hour to 50 N, 60 degrees Celsius, 1 hour to 50 N, 80 degrees Celsius, 1 hour, and the friction coefficient μ in 1 hour under each load and at each temperature was determined. The friction coefficient μ under 50 N and at 60 degrees Celsius, and under 50 N and at 80 degrees Celsius was expressed as μ50N60 degrees Celsius and μ5080 degrees Celsius, respectively. The following value was computed.

Δμ1=μ5080 degrees Celsius−μ(50N60 degrees Celsius)

Solid samples were not tested.

(4) Viscosity:

5 mL of a sample was put into a tube, and set at a liquid temperature of 40 degrees Celsius in a dry block bath (As One's trade name, EB-303). The oscillator of an oscillation-type viscometer (CBC's trade name, VISCOMETER VM-10A-M) was immersed in the sample, and after 3 minutes, the viscosity of the sample was measured. Solid samples were not tested.

1-1 Example 1

66.4 g of triethylene glycol monoethyl ether (by Tokyo Chemical), 37.3 g of succinic anhydride (by Wako Pure Chemicals) and 10 mL of toluene (7% by mass of the starting mixture) were fed into a reactor equipped with a Dean Stark dehydrating unit. This was heated at a liquid temperature of 120 degrees Celsius and stirred for 4 hours. 12.6 g of pentaerythritol (by Wako Pure Chemicals, purity 95%) was added thereto, and stirred at a liquid temperature of from 170 to 190 degrees Celsius for 12 hours. During this, toluene was refluxed and 6.4 ml of water was thereby removed. The reaction system was made under reduced pressure and the volatile was removed. The liquid temperature was made room temperature, and the system was filtered. 98.6 g of a colorless transparent oil was obtained.

The GPC chart of the product is shown in FIG. 1.

The areal ratio of the light component having a low molecular weight (the retention time thereof was after 15 minutes) and containing a sharp peak of diester (the retention time thereof was 15.26 minutes) was determined. The viscosity and the friction coefficient of the oily product were measured as above. The results are shown in Table 1.

Figure 2:
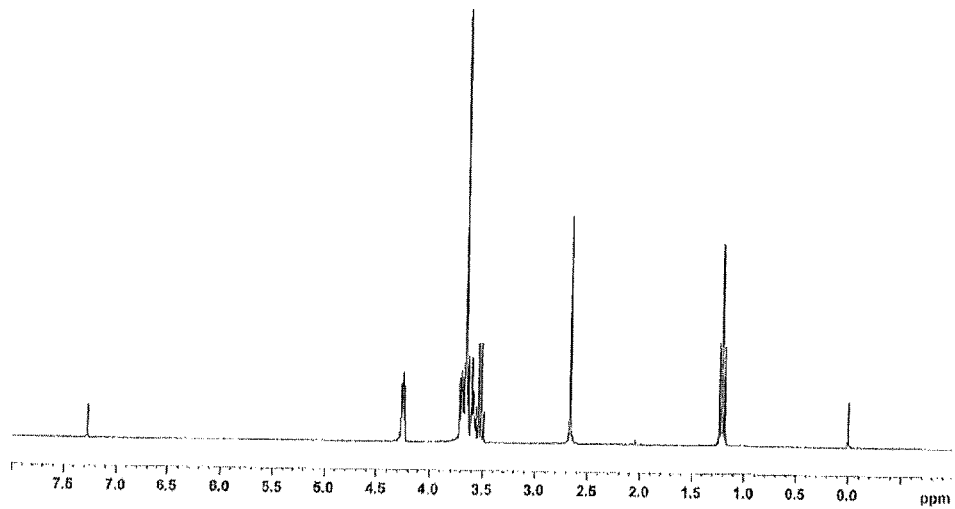
FIG. 2 This is a $^1$H-NMR chart of the compound of the formula 1 in Example 1.

The above diester is bis-{2-[2-(2-ethoxy-ethoxy)-ethoxy] ethyl}succinate (the following formula 1). For confirmation, the diester was synthesized with reference to the Compound 5 described in Journal of Organic Chemistry, 2003, Vol. 68, p. 8149. The $^1$H-NMR chart of the obtained compound is shown in FIG. 2. In GPC, the retention time of the compound corresponded to the retention time in FIG. 1.

Formula 1:

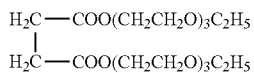

1-2 Example 2

66.7 g of triethylene glycol monoethyl ether (by Tokyo Chemical), 44.0 g of succinic acid (by Wako Pure Chemicals), 12.6 g of pentaerythritol (by Wako Pure Chemicals, purity 95%) and 15 mL of toluene (11% by mass of the starting mixture) were fed into a reactor equipped with a Dean Stark dehydrating unit. This was stirred at a liquid temperature of from 135 to 190 degrees Celsius for 13 hours. During this, toluene was refluxed and 13.0 ml of water was thereby removed. The reaction system was made under reduced pressure and the volatile was removed. The liquid temperature was made room temperature, and the system was filtered. 95.2 g of a colorless transparent oil was obtained.

Figure 3:
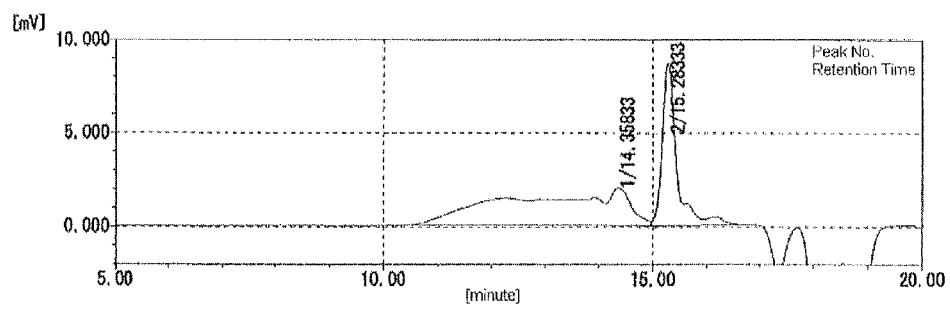
FIG. 3 This is a GPC chart of the product in Example 2.

The GPC chart of the product is shown in FIG. 3. The ratio of the light component was obtained from the GPC chart. The viscosity and the friction coefficient of the oily product were measured as above. The results are shown in Table 1.

1-3 Example 3

84.0 g of triethylene glycol monoethyl ether (by Tokyo Chemical), 44.0 g of succinic acid (by Wako Pure Chemicals), 12.6 g of pentaerythritol (by Wako Pure Chemicals, purity 95%) and 10 mL of toluene (6% by mass of the starting mixture) were fed into a reactor equipped with a Dean Stark dehydrating unit. This was stirred at a liquid temperature of from 155 to 185 degrees Celsius for 7 hours. During this, toluene was refluxed and 13.2 ml of water was thereby removed. The reaction system was made under reduced pressure and the volatile was removed. The resulting residue was filtered. 95.3 g of a colorless transparent oil was obtained.

Figure 4:
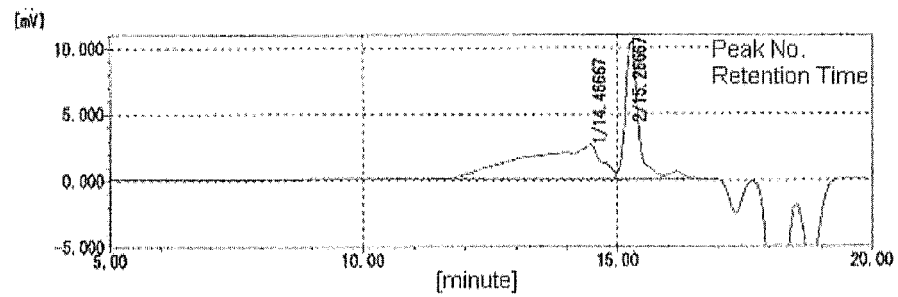
FIG. 4 This is a GPC chart of the product in Example 3.

The GPC chart of the product is shown in FIG. 4. The ratio of the light component was obtained from the GPC chart. The viscosity and the friction coefficient of the oily product were measured as above. The results are shown in Table 1.

Figure 5:
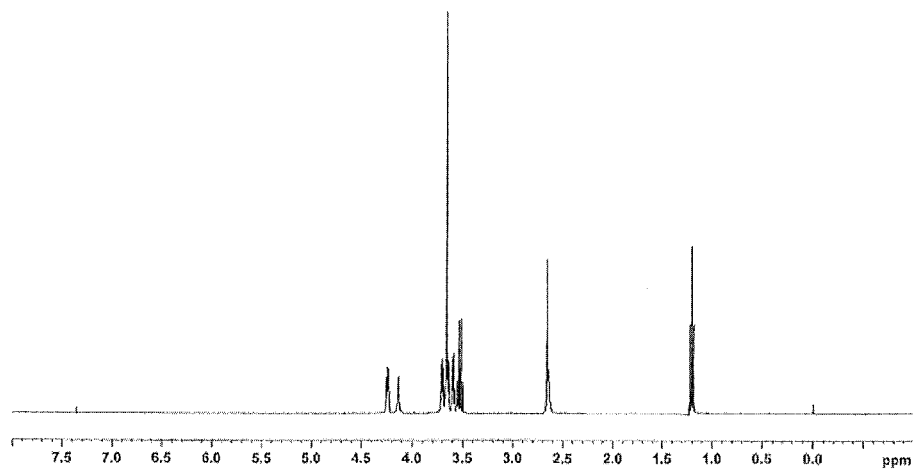
FIG. 5 This is a $^1$H-NMR chart of the product in Example 3.
Figure 6:
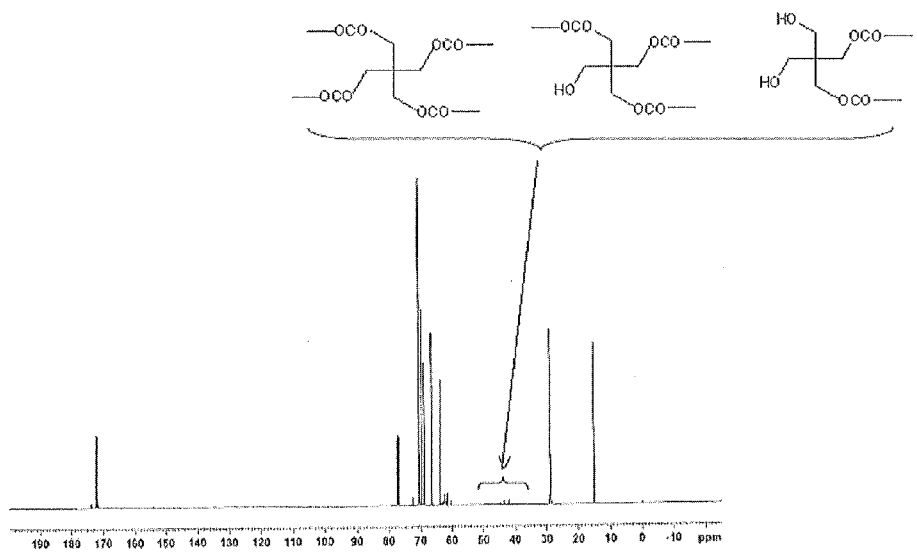
FIG. 6 This is a $^{13}$C-NMR chart of the product in Example 3.

The $^1$H-NMR chart of the product is shown in FIG. 5; and the $^{13}$C-NMR chart thereof is in FIG. 6. In the $^{13}$C-NMR chart, three peaks are seen at around 40 ppm, and these are for the tetra-esterified quaternary carbon, the tri-esterified quaternary carbon and the di-esterified quaternary carbon of $CH_2Os$ bonding to the quaternary carbon derived from pentaerythritol. The integrated areal ratio of these was 39.4/47.9/12.7. The computation based on this confirmed that 3.27 OHs (4×0.394+3×0.479+2×0.127=3.27) of four OHs of pentaerythritol were esterified. From this, the OH residual ratio of pentaerythritol is (4−3.27)/4×100=18%. The samples obtained in Examples using pentaerythritol and in Comparative Examples were analyzed in the same manner for $^{13}$C-NMR, from which the OH residual ratio was obtained. The results are shown in Table 1.

1-4 Example 4

151.9 g of triethylene glycol monoethyl ether (by Tokyo Chemical), 82.2 g of succinic acid (by Wako Pure Chemicals), 19.0 g of pentaerythritol (by Wako Pure Chemicals, purity 95%) and 20 mL of toluene (7% by mass of the starting mixture) were fed into a reactor equipped with a Dean Stark dehydrating unit. This was stirred at a liquid temperature of from 130 to 180 degrees Celsius for 15 hours. During this, toluene was refluxed and 24.0 ml of water was thereby removed. The reaction system was made under reduced pressure and the volatile was removed. The resulting residue was filtered. 207.8 g of a colorless transparent oil was obtained.

The GPC chart of the product is shown in FIG. 7. The ratio of the light component was obtained from the GPC chart. The viscosity and the friction coefficient of the oily product were measured as above. The results are shown in Table 1.

1-5 Example 5

85.4 g of triethylene glycol monoethyl ether (by Tokyo Chemical), 54.5 g of adipic acid (by Wako Pure Chemicals), 12.6 g of pentaerythritol (by Wako Pure Chemicals, purity 95%) and 20 mL of toluene (11% by mass of the starting mixture) were fed into a reactor equipped with a Dean Stark dehydrating unit. This was stirred at a liquid temperature of from 130 to 160 degrees Celsius for 10 hours. During this, toluene was refluxed and 11.5 ml of water was thereby removed. The reaction system was made under reduced pressure and the volatile was removed. The resulting residue was filtered. 120.1 g of a colorless transparent oil was obtained.

The GPC chart of the product is shown in FIG. 8. The ratio of the light component was obtained from the GPC chart. The viscosity and the friction coefficient of the oily product were measured as above. The results are shown in Table 1.

1-6 Example 6

97.9 g of triethylene glycol monobutyl ether (by Tokyo Chemical), 44.0 g of succinic acid (by Wako Pure Chemicals), 12.6 g of pentaerythritol (by Wako Pure Chemicals, purity 95%) and 15 mL of toluene (8% by mass of the starting mixture) were fed into a reactor equipped with a Dean Stark dehydrating unit. This was stirred at a liquid temperature of from 140 to 160 degrees Celsius for 7 hours. During this, toluene was refluxed and 12.0 ml of water was thereby removed. The reaction system was made under reduced pressure and the volatile was removed. The resulting residue was filtered. 120.2 g of a colorless transparent oil was obtained.

The GPC chart of the product is shown in FIG. 9. The ratio of the light component was obtained from the GPC chart. The viscosity and the friction coefficient of the oily product were measured as above. The results are shown in Table 1.

1-7 Example 7

127.4 g of diethylene glycol monoethyl ether (by Tokyo Chemical), 88.0 g of succinic acid (by Wako Pure Chemicals), 25.3 g of pentaerythritol (by Wako Pure Chemicals, purity 95%) and 20 mL of toluene (7% by mass of the starting mixture) were fed into a reactor equipped with a Dean Stark dehydrating unit. This was stirred at a liquid temperature of from 130 to 180 degrees Celsius for 9 hours. During this, toluene was refluxed and 13.0 ml of water was thereby removed. The reaction system was made under reduced pressure and the volatile was removed. The resulting residue was filtered. 133.4 g of a colorless transparent oil was obtained.

Figure 10:
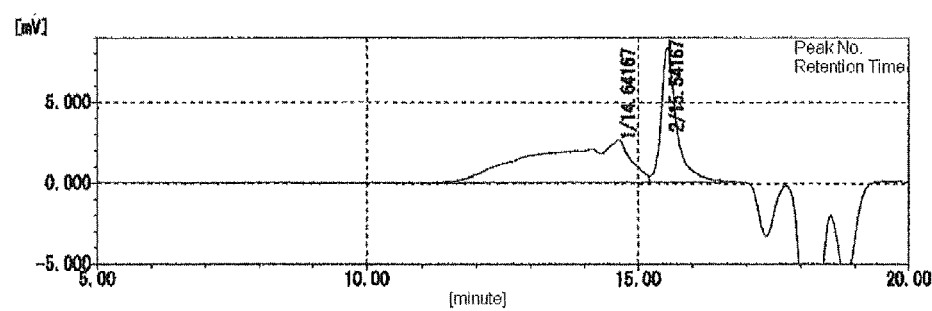
FIG. 10 This is a GPC chart of the product in Example 7.

The GPC chart of the product is shown in FIG. 10. The ratio of the light component was obtained from the GPC chart. The viscosity and the friction coefficient of the oily product were measured as above. The results are shown in Table 1.

1-8 Example 8

78.0 g of triethylene glycol monomethyl ether (by Tokyo Chemical), 44.0 g of succinic acid (by Wako Pure Chemicals), 12.7 g of pentaerythritol (by Wako Pure Chemicals, purity 95%) and 15 mL of toluene (10% by mass of the starting mixture) were fed into a reactor equipped with a Dean Stark dehydrating unit. This was stirred at a liquid temperature of from 140 to 150 degrees Celsius for 8 hours. During this, toluene was refluxed and 12.6 ml of water was thereby removed. The reaction system was made under reduced pressure and the volatile was removed. The resulting residue was filtered. 84.1 g of a colorless transparent oil was obtained.

Figure 11:
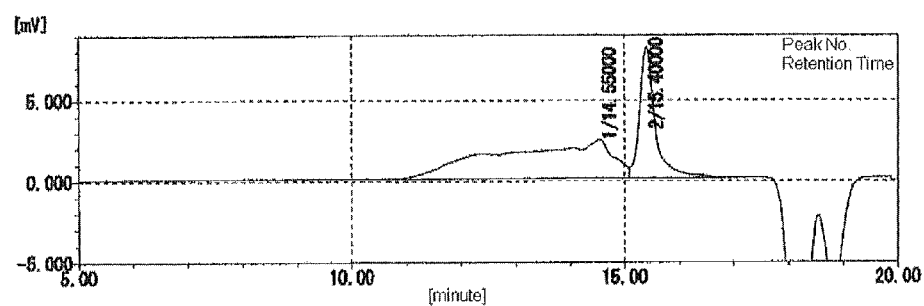
FIG. 11 This is a GPC chart of the product in Example 8.

The GPC chart of the product is shown in FIG. 11. The ratio of the light component was obtained from the GPC chart. The viscosity and the friction coefficient of the oily product were measured as above. The results are shown in Table 1.

1-9 Example 9

66.3 g of triethylene glycol monoethyl ether (by Tokyo Chemical), 33.0 g of succinic acid (by Wako Pure Chemicals), 12.5 g of trimethylolpropane (by Wako Pure Chemicals) and 15 mL of toluene (12% by mass of the starting mixture) were fed into a reactor equipped with a Dean Stark dehydrating unit. This was stirred at a liquid temperature of from 130 to 160 degrees Celsius for 6 hours. During this, toluene was refluxed and 9.5 ml of water was thereby removed. The reaction system was made under reduced pressure and the volatile was removed. The resulting residue was filtered. 77.4 g of a colorless transparent oil was obtained.

Figure 12:
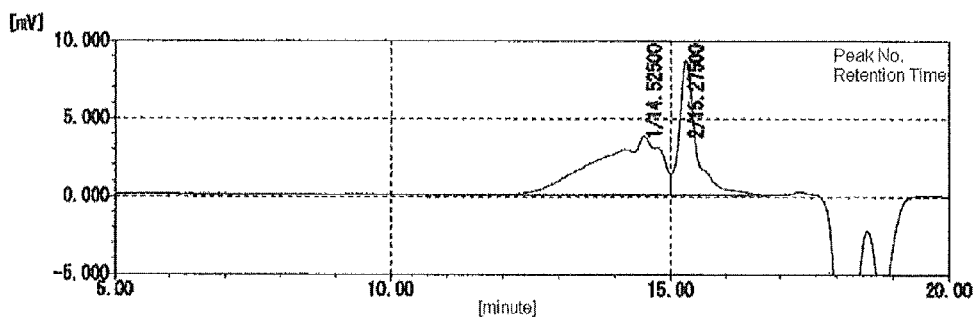
FIG. 12 This is a GPC chart of the product in Example 9.

The GPC chart of the product is shown in FIG. 12. The ratio of the light component was obtained from the GPC chart. The viscosity and the friction coefficient of the oily product were measured as above. The results are shown in Table 1.

In the $^{13}$C-NMR chart of the product, three peaks are seen at around 40 ppm. These are for the tri-esterified quaternary carbon, the di-esterified quaternary carbon and the mono-esterified quaternary carbon of $CH_2Os$ bonding to the quaternary carbon derived from trimethylolpropane. The integrated areal ratio of these was 64.3/33.3/2.4. The computation based on this confirmed that 2.61 OHs (3×0.643+2×0.333+1×0.024=2.61) of four OHs of trimethylolpropane were esterified. From this, the OH residual ratio of trimethylolpropane is (4−3.27)/4×100=13%. The samples obtained in Examples using trimethylolpropane and in Comparative Examples were analyzed in the same manner for $^{13}$C-NMR, from which the OH residual ratio was obtained. The results are shown in Table 1.

1-10 Example 10

66.5 g of triethylene glycol monoethyl ether (by Tokyo Chemical), 40.8 g of adipic acid (by Wako Pure Chemicals), 12.5 g of trimethylolpropane (by Wako Pure Chemicals), and 15 mL of toluene (11% by mass of the starting mixture) were fed into a reactor equipped with a Dean Stark dehydrating unit. This was stirred at a liquid temperature of from 130 to 160 degrees Celsius for 6 hours. During this, toluene was refluxed and 9.5 ml of water was thereby removed. The reaction system was made under reduced pressure and the volatile was removed. The resulting residue was filtered. 93.2 g of a colorless transparent oil was obtained.

Figure 13:
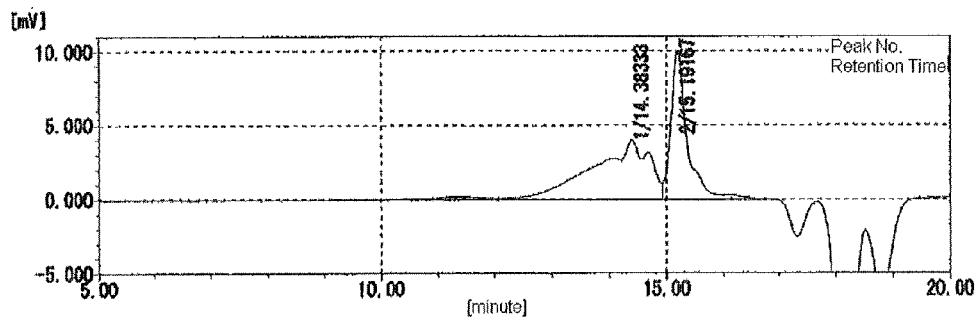
FIG. 13 This is a GPC chart of the product in Example 10.

The GPC chart of the product is shown in FIG. 13. The ratio of the light component was obtained from the GPC chart. The viscosity and the friction coefficient of the oily product were measured as above. The results are shown in Table 1.

1-11 Example 11

88.5 g of triethylene glycol monoethyl ether (by Tokyo Chemical), 44.0 g of succinic acid (by Wako Pure Chemicals), 11.5 g of glycerin (by Wako Pure Chemicals), and 10 mL of toluene (6% by mass of the starting mixture) were fed into a reactor equipped with a Dean Stark dehydrating unit. This was stirred at a liquid temperature of from 140 to 165 degrees Celsius for 8 hours. During this, toluene was refluxed and 12.4 ml of water was thereby removed. The reaction system was made under reduced pressure and the volatile was removed. The resulting residue was filtered. 114.9 g of a colorless transparent oil was obtained.

Figure 14:
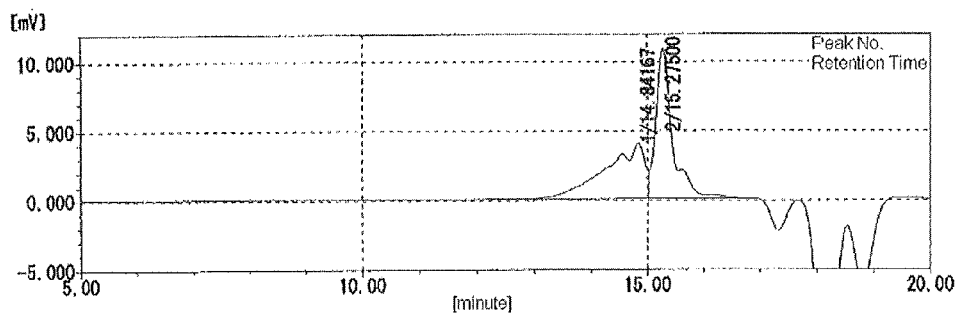
FIG. 14 This is a GPC chart of the product in Example 11.

The GPC chart of the product is shown in FIG. 14. The ratio of the light component was obtained from the GPC chart. The viscosity and the friction coefficient of the oily product were measured as above. The results are shown in Table 1.

1-12 Example 12

83.2 g of triethylene glycol monoethyl ether (by Tokyo Chemical), 44.0 g of succinic acid (by Wako Pure Chemicals), 15.8 g of dipentaerythritol (by Wako Pure Chemicals), and 10 mL of toluene (6% by mass of the starting mixture) were fed into a reactor equipped with a Dean Stark dehydrating unit. This was stirred at a liquid temperature of from 140 to 165 degrees Celsius for 10 hours. During this, toluene was refluxed and 12.0 ml of water was thereby removed. The reaction system was made under reduced pressure and the volatile was removed. The resulting residue was filtered. 105.2 g of a colorless transparent oil was obtained.

Figure 15:
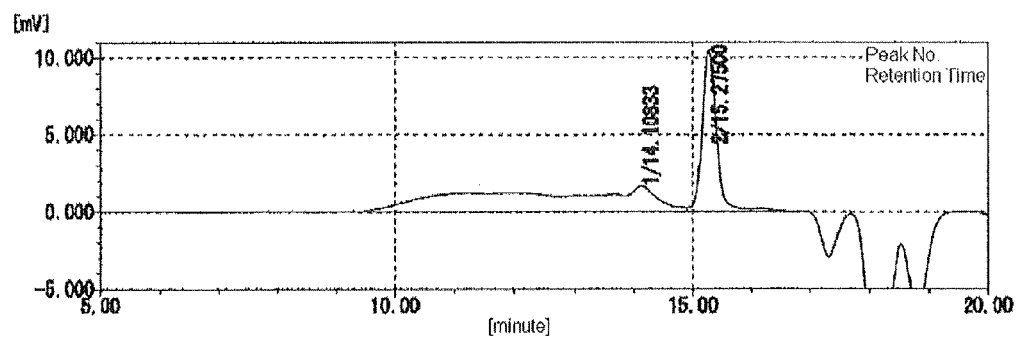
FIG. 15 This is a GPC chart of the product in Example 12.

The GPC chart of the product is shown in FIG. 15. The ratio of the light component was obtained from the GPC chart. The viscosity and the friction coefficient of the oily product were measured as above. The results are shown in Table 1.

1-13 Example 13

84.1 g of triethylene glycol monoethyl ether (by Tokyo Chemical), 75.4 g of sebacic acid (by Wako Pure Chemicals), 15.8 g of pentaerythritol (by Wako Pure Chemicals), and 10 mL of toluene (5% by mass of the starting mixture) were fed into a reactor equipped with a Dean Stark dehydrating unit. This was stirred at a liquid temperature of from 140 to 175 degrees Celsius for 10 hours. During this, toluene was refluxed and 13.0 ml of water was thereby removed. The reaction system was made under reduced pressure and the volatile was removed. The resulting residue was filtered. 140.1 g of a colorless transparent oil was obtained.

Figure 16:
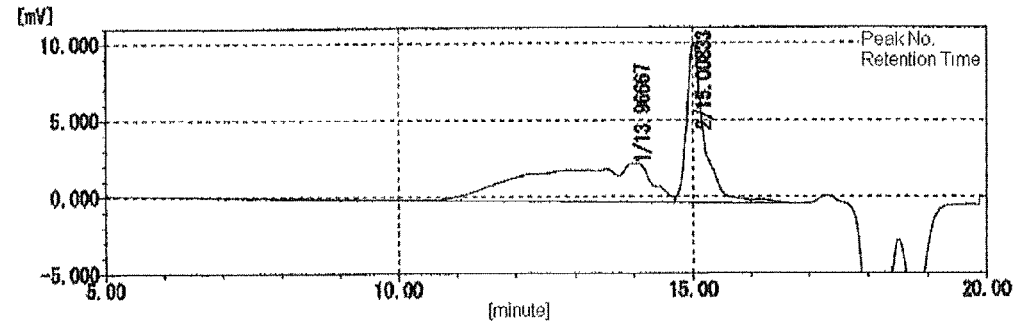
FIG. 16 This is a GPC chart of the product in Example 13.

The GPC chart of the product is shown in FIG. 16. The ratio of the light component was obtained from the GPC chart. The viscosity and the friction coefficient of the oily product were measured as above. The results are shown in Table 1.

1-14 Example 14

Figure 17:
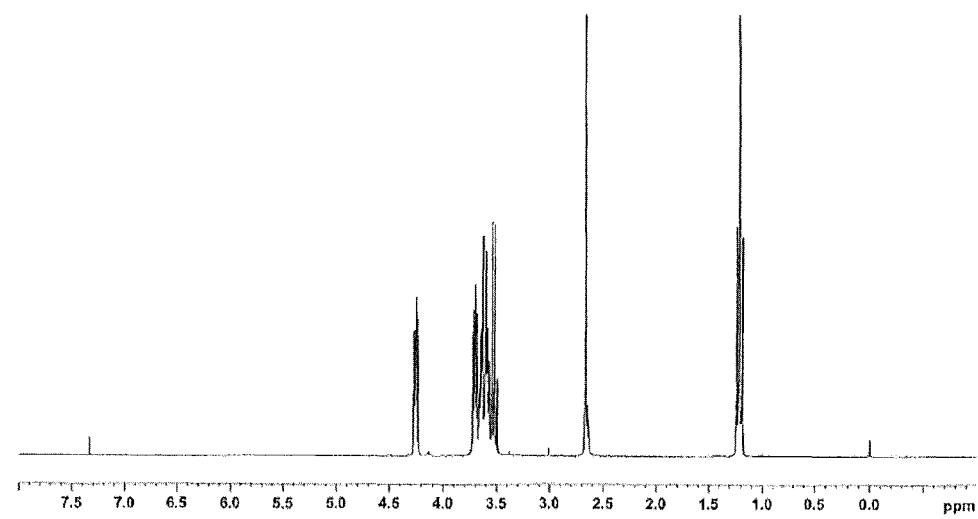
FIG. 17 This is a $^1$H-NMR chart of the light component obtained in Example 14.

The oily product obtained in Production Example 7 was further processed for reduced-pressure distillation (by heating up to 240 degrees Celsius under 5 mmHg) to give a light fraction mainly comprising bis-[2-[(2-ethoxy-ethoxy)]-ethyl] succinate (of the following formula 2). The $^1$H-NMR chart of the light fraction is shown in FIG. 17.

Formula 2:

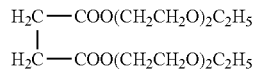

The high-viscosity oil remaining in the flask was filtered to give a colorless transparent oil.

Figure 18:
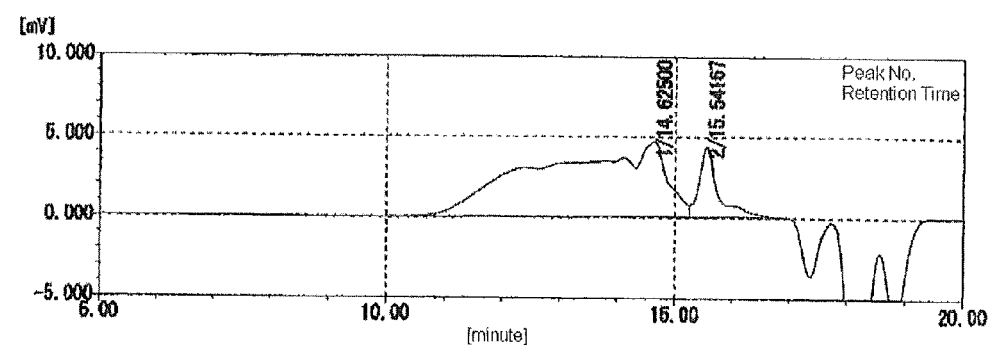
FIG. 18 This is a GPC chart of the high-viscosity oil obtained in Example 14.

The GPC chart of the high-viscosity oil is shown in FIG. 18. The ratio of the light component was obtained from the GPC chart. The viscosity and the friction coefficient of the oily product were measured as above. The results are shown in Table 1.

1-15 Example 15

The high-viscosity oil and the light fraction obtained in Production Example 14 were mixed in a ratio by mass of 50/50 to give a colorless transparent oil.

Figure 19:
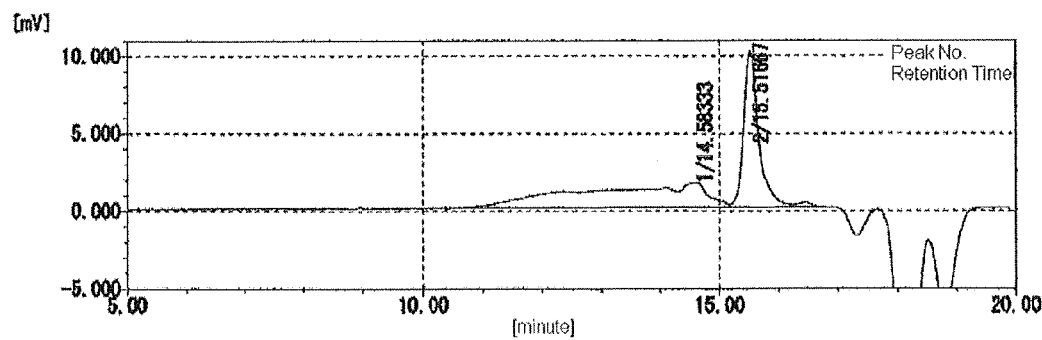
FIG. 19 This is a GPC chart of the product in Example 15.

The GPC chart of the colorless transparent oil is shown in FIG. 19. The ratio of the light component was obtained from the GPC chart. The viscosity and the friction coefficient of the oily product were measured as above. The results are shown in Table 1.

1-16 Example 16

The high-viscosity oil and the light fraction obtained in Production Example 14 were mixed in a ratio by mass of 25/75 to give a colorless transparent oil.

Figure 20:
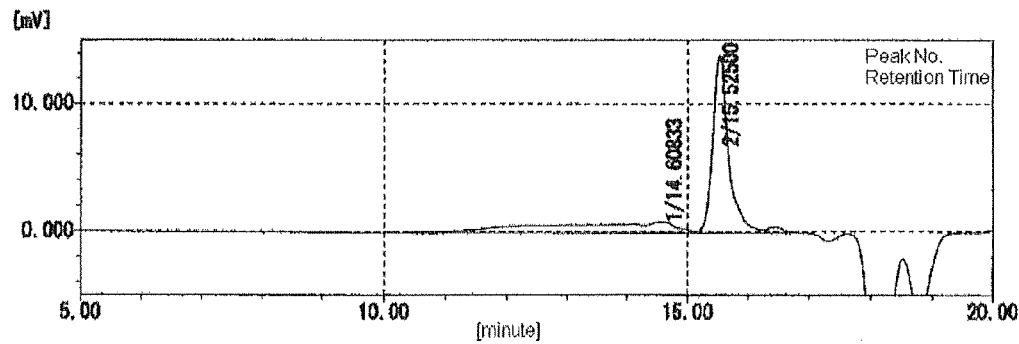
FIG. 20 This is a GPC chart of the product in Example 16.

The GPC chart of the colorless transparent oil is shown in FIG. 20. The ratio of the light component was obtained from the GPC chart. The viscosity and the friction coefficient of the oily product were measured as above. The results are shown in Table 1.

1-17 Example 17

5 mL of acetic anhydride (by Wako Pure Chemicals) was added to 20 g of the oil obtained in Production Example 3, and stirred at 150 degrees Celsius for 2 hours. This was processed through evaporation to remove the remaining acetic acid and acetic anhydride.

The obtained product was analyzed through GPC, and there was found no difference between the GPC chart of the product and that of the oil obtained in Example 3. The ratio of the light component was obtained from the GPC chart. The viscosity and the friction coefficient of the oily product were measured as above. The results are shown in Table 1.

Figure 21:
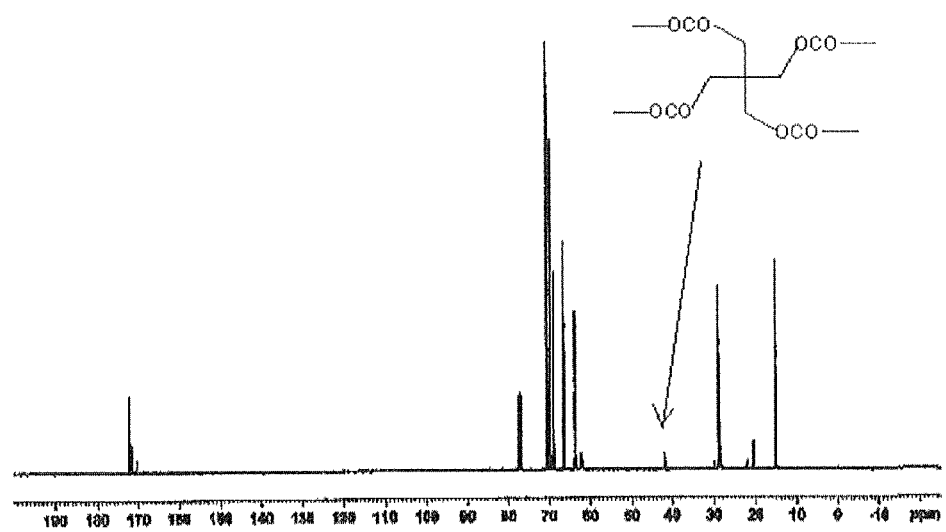
FIG. 21 This is a $^{13}$C-NMR chart of the product in Example 17.

The $^{13}$C-NMR chart of the product is shown in FIG. 21. One peak appeared at around 40 ppm in the chart, which confirms that all $CH_2Os$ bonding to the quaternary carbon derived from pentaerythritol were esterified.

1-18 Example 18

Figure 27:
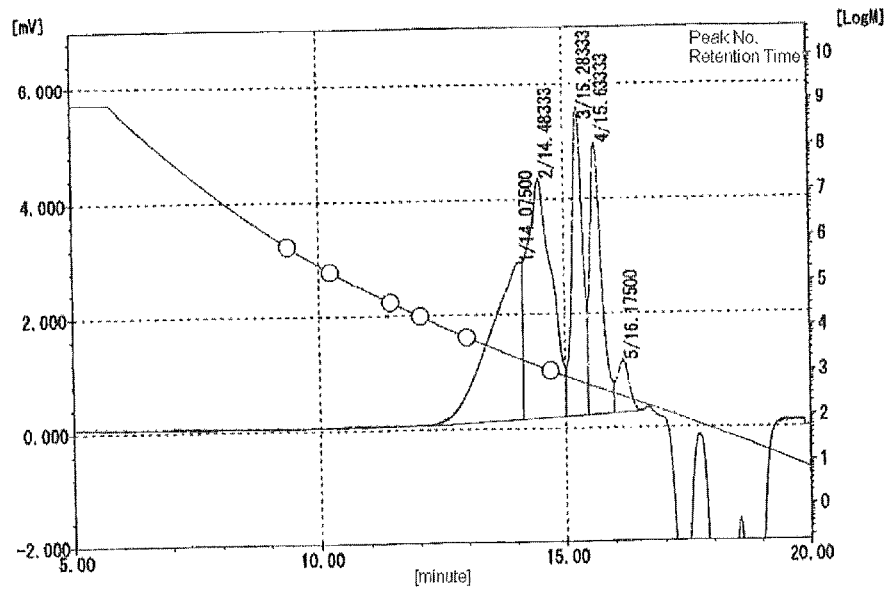
FIG. 27 This is a GPC chart of the product in Example 18.

30.1 g of triethylene glycol monoethyl ether (by Tokyo Chemical) and 16.9 g of succinic anhydride (by Wako Pure Chemicals) were fed into a reactor equipped with a Dean Stark dehydrating unit, and reacted at a liquid temperature of 120 degrees Celsius for 6 hours therein. 5.75 g of pentaerythritol (by Wako Pure chemicals, purity 95%) was added thereto, and stirred at a liquid temperature of 140 to 170 degrees Celsius for 10 hours. During this, toluene was refluxed and 5.9 ml of water was thereby removed. The reaction system was made under reduced pressure and the volatile was removed. The liquid temperature was made room temperature, and the system was filtered. 40.3 g of a colorless transparent oil was obtained. The GPC chart of the product is shown in FIG. 27. The light component of this oil comprises, along with the above-mentioned diester, bis-{2-[2-(2-ethoxy-ethoxy)-ethoxy]-ethyl}succinate, and a monoester, mono-{2-[2-(2-ethoxy-ethoxy)-ethoxy]-ethyl}succinate, and the starting compound, triethylene glycol monoethyl ether. It is considered that the presence of the monoester in the component would be because the amount of the alcohol added was small.

Figure 28:
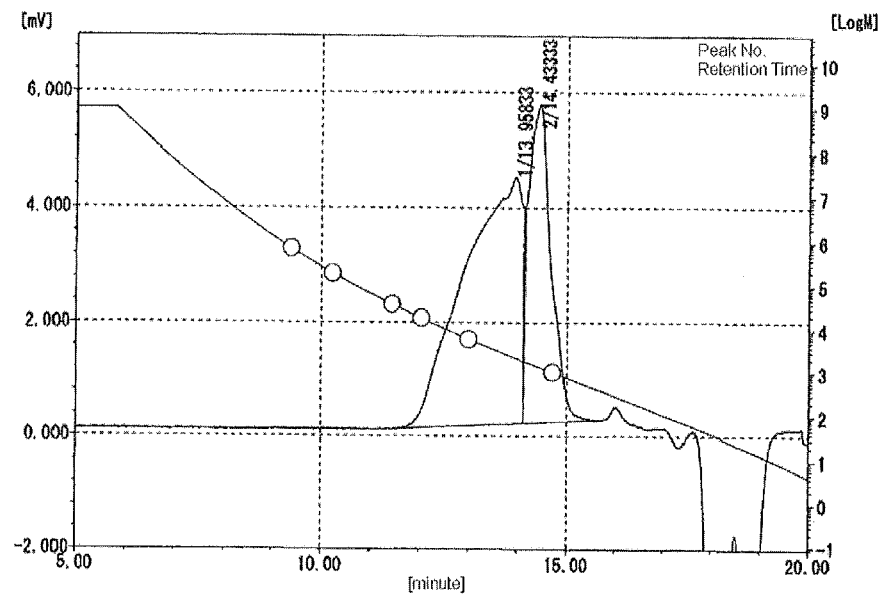
FIG. 28 This is a GPC chart of the polyester partitioned from the product in Example 18.
Figure 29:
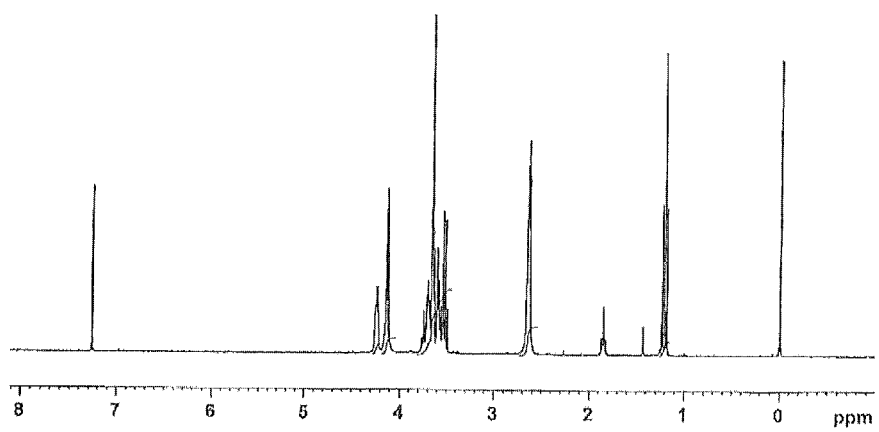
FIG. 29 This is a $^1$H-NMR chart of the polyester partitioned from the product in Example 18.

The oil was processed through partitioning GPC (GPC, Japan Analytical Industry's trade name, LC-908-C60/two columns, Japan Analytical Industry's trade names, JAIGEL-2.5H and JAIGEL-3H; developing solvent, tetrahydrofuran) to partition the polyester component. The GPC chart of the component is shown in FIG. 28, and the $^1$H-NMR chart thereof is in FIG. 29. The GPC chart confirms the isolation of the polyester component. The attribution analysis of the $^1$H-NMR chart is as follows, not contradictory to the partial structure of the polyester. Accordingly, the presence of the 2-[2-(2-ethoxy-ethoxy)-ethoxy]-ethyl group in the polyester was confirmed.

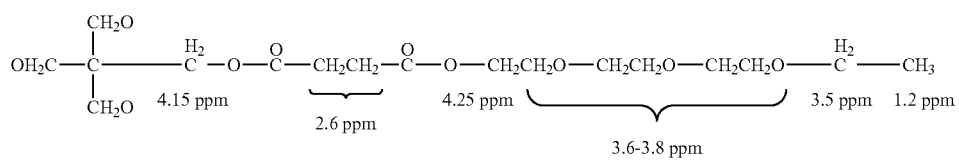

From the above, it is obvious that the 2-[2-(2-ethoxy-ethoxy)-ethoxy]-ethyl group exists in the polyester component.

1-19 Example 19

2.6 g of $C(CH_2OCOCH_2CH_2COOH)_4$ that had been prepared by reacting one mol of pentaerythritol (by Wako Pure Chemicals) and 4 mols of succinic anhydride (by Wako Pure Chemicals), 24.1 g of polyethylene glycol monodococyl ether (prepared by reacting 1 mol of Takemoto Oil & Fat's behenyl alcohol $C_{22}H_{45}OH$ and about 20 mols of ethylene oxide; this was confirmed to have a composition of $C_{22}H_{45}(OCH_2CH_2)_{20}OH$ from the integral ratio of the methyl group and the oxyethylene group in $^1$HNMR analysis thereof, and accordingly, the theoretical molecular weight of the compound was 1210; and in GPC analysis, the polystyrene-equivalent Mw thereof was 1920 and Mn thereof was 1800), 135 mg of paratoluenesulfonic acid (by Wako Pure Chemicals) and 20 mL of mesitylene were fed into a reactor equipped with a Dean Stark dehydrating unit. This was stirred at a liquid temperature of from 155 to 160 degrees Celsius for 9 hours. During this, mesitylene was gently refluxed and water was thereby removed. The reaction product was reprecipitated in hexane to give a white yellow solid.

Figure 30:
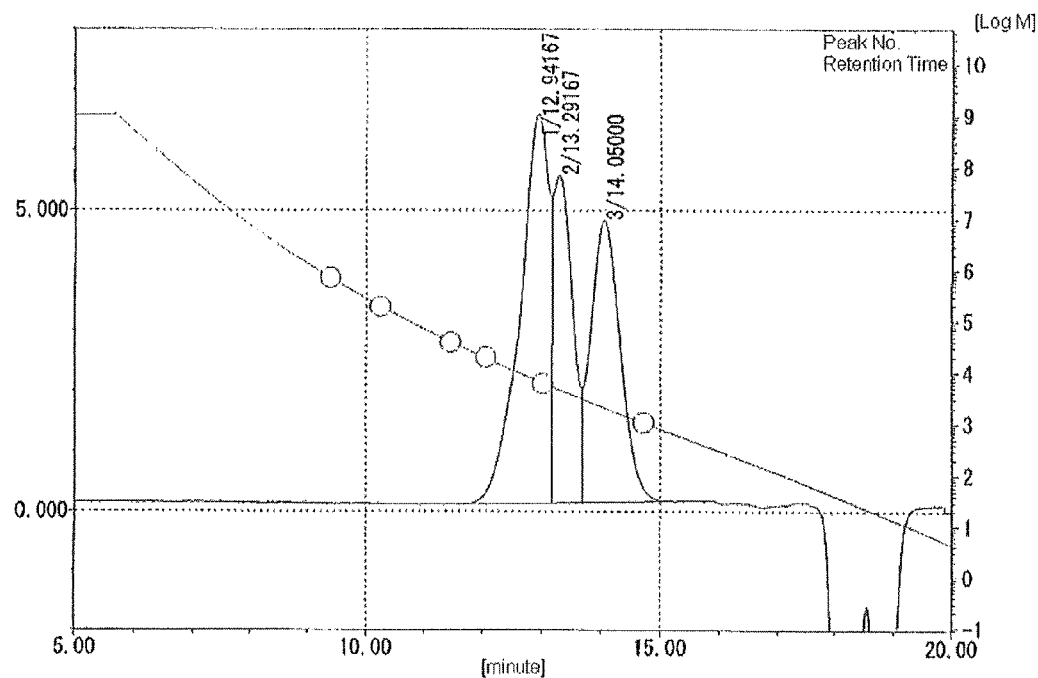
FIG. 30 This is a GPC chart of the product in Example 18.

The GPC chart of the product is shown in FIG. 30. From this, the proportion of the light component was 57%.

1-20 Example 20

6.3 g of pentaerythritol (by Wako Pure Chemicals), 22.0 g of succinic acid (by Wako Pure Chemicals), 285.8 g of polyethylene glycol monodococyl ether (prepared by reacting 1 mol of Takemoto Oil & Fat's behenyl alcohol $C_{22}H_{45}OH$ and about 20 mols of ethylene oxide; this was confirmed to have a composition of $C_{22}H_{45}(OCH_2CH_2)_{20}OH$ from the integral ratio of the methyl group and the oxyethylene group in $^1$HNMR analysis thereof, and accordingly, the theoretical molecular weight of the compound was 1210; and in GPC analysis, the polystyrene-equivalent Mw thereof was 1920 and Mn thereof was 1800) and 10 mL of toluene were fed into a reactor equipped with a Dean Stark dehydrating unit. This was stirred at a liquid temperature of from 155 to 160 degrees Celsius for 9 hours. During this, toluene was refluxed and water was thereby removed. The reaction product was reprecipitated in hexane to give a white yellow solid. Through GPC thereof, the proportion of the light component in the product was 42%.

1-21 Example 21

6.3 g of pentaerythritol (by Wako Pure Chemicals), 22.0 g of succinic acid (by Wako Pure Chemicals), 177.5 g of polyethylene glycol monooctadecyl ether (prepared by reacting 1 mol of Takemoto Oil & Fat's octadecanol $C_{18}H_{37}OH$ and about 10 mols of ethylene oxide; this was confirmed to have a composition of $C_{18}H_{37}(OCH_2CH_2)_{11}OH$ from the integral ratio of the methyl group and the oxyethylene group in $^1HNMR$ analysis thereof, and accordingly, the theoretical molecular weight of the compound was 750; and in GPC analysis, the polystyrene-equivalent Mw thereof was 1320 and Mn thereof was 1120) and 10 mL of toluene were fed into a reactor equipped with a Dean Stark dehydrating unit. This was stirred at a liquid temperature of from 140 to 170 degrees Celsius for 9 hours. During this, toluene was refluxed and water was thereby removed. The reaction product was reprecipitated in hexane to give a white yellow solid. Through GPC thereof, the proportion of the light component in the product was 41%.

1-22 Comparative Example 1

56.2 g of 1-decanol (by Wako Pure Chemicals), 35.1 g of succinic anhydride (by Wako Pure Chemicals) and 10 mL of toluene were fed into a reactor equipped with a Dean Stark dehydrating unit. This was stirred at a liquid temperature of 110 degrees Celsius for 4 hours. 11.9 g of pentaerythritol (by Wako Pure Chemicals, purity 95%) was added thereto, and stirred at a liquid temperature of from 150 to 160 degrees Celsius for 8 hours. During this, toluene was refluxed and 5.4 ml of water was thereby removed. The reaction system was made under reduced pressure and the volatile was removed. The liquid temperature was made room temperature, and the system was filtered. 86.2 g of a white emulsion was obtained.

Figure 22:
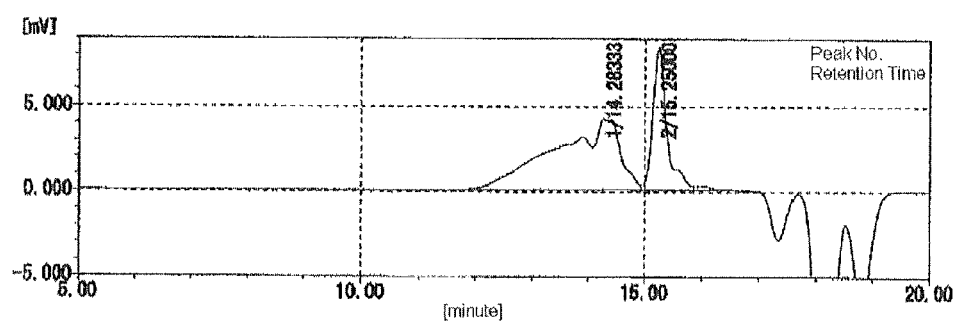
FIG. 22 This is a GPC chart of the product in Comparative Example 1.

The GPC chart of the product is shown in FIG. 22. The ratio of the light component was obtained from the GPC chart. The viscosity and the friction coefficient of the oily product were measured as above. The results are shown in Table 1.

1-23 Comparative Example 2

56.3 g of 1-decanol (by Wako Pure Chemicals), 35.1 g of succinic anhydride (by Wako Pure Chemicals) and 10 mL of toluene were fed into a reactor equipped with a Dean Stark dehydrating unit. This was stirred at a liquid temperature of 110 degrees Celsius for 4 hours. 12.0 g of pentaerythritol (by Wako Pure Chemicals, purity 95%) was added thereto, and stirred at a liquid temperature of from 140 to 160 degrees Celsius for 8 hours. During this, toluene was refluxed and 5.2 ml of water was thereby removed. The reaction system was made under reduced pressure and the volatile was removed. The liquid temperature was made room temperature, and 92.0 g of a white solid was obtained.

Figure 23:
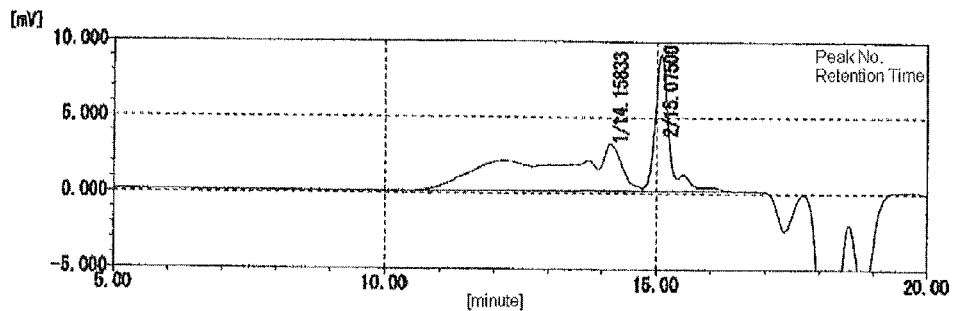
FIG. 23 This is a GPC chart of the product in Comparative Example 2.

The GPC chart of the product is shown in FIG. 23. The ratio of the light component was obtained from the GPC chart. Since the product was solid, the viscosity and the friction coefficient thereof could not be measured.

1-24 Comparative Example 3

42.9 g of 3,3,5-trimethyl-1-hexanol (by Wako Pure Chemicals), 35.1 g of succinic anhydride (by Wako Pure Chemicals) and 10 mL of toluene were fed into a reactor equipped with a Dean Stark dehydrating unit. This was stirred at a liquid temperature of 110 degrees Celsius for 4 hours. 12.0 g of pentaerythritol (by Wako Pure Chemicals, purity 95%) was added thereto, and stirred at a liquid temperature of from 145 to 160 degrees Celsius for 8 hours. During this, toluene was refluxed and 5.2 ml of water was thereby removed. The reaction system was made under reduced pressure and the volatile was removed. The liquid temperature was made room temperature, and the system was filtered. 80.1 g of a colorless transparent oil was obtained.

Figure 24:
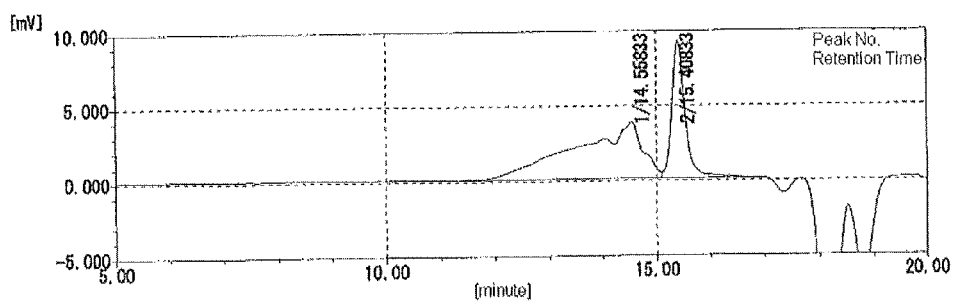
FIG. 24 This is a GPC chart of the product in Comparative Example 3.

The GPC chart of the product is shown in FIG. 24. The ratio of the light component was obtained from the GPC chart. The viscosity and the friction coefficient of the oily product were measured as above. The results are shown in Table 1.

1-25 Comparative Example 4

68.0 g of 3,3,5-trimethyl-1-hexanol (by Wako Pure Chemicals), 44.0 g of succinic acid (by Wako Pure Chemicals), 12.7 g of pentaerythritol (by Wako Pure Chemicals, purity 95%) and 10 mL of toluene were fed into a reactor equipped with a Dean Stark dehydrating unit. This was stirred at a liquid temperature of from 150 to 160 degrees Celsius for 9 hours. Accordingly, 11.6 mL of water was generated. As it was, the reaction system was made under reduced pressure and the volatile was removed. The liquid temperature was made room temperature, and the system was filtered. 69.1 g of a colorless transparent oil was obtained.

Figure 25:
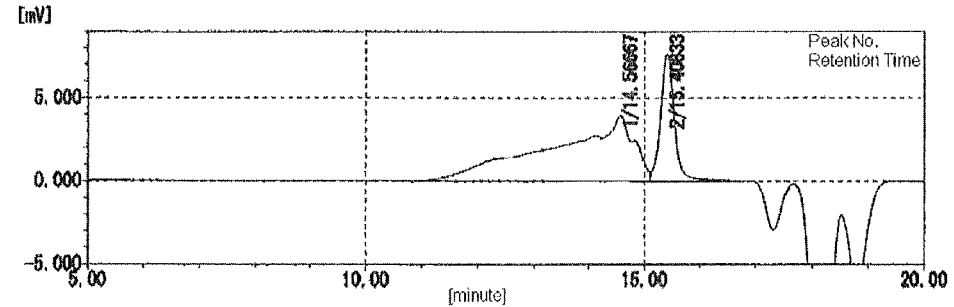
FIG. 25 This is a GPC chart of the product in Comparative Example 4.

The GPC chart of the product is shown in FIG. 25. The ratio of the light component was obtained from the GPC chart. The viscosity and the friction coefficient of the oily product were measured as above. The results are shown in Table 1.

1-26 Comparative Example 5

13.4 g of 3,3,5-trimethyl-1-hexanol (by Wako Pure Chemicals), 40.2 g of succinic acid (by Wako Pure Chemicals), 43.6 g of trimethylolpropane (by Wako Pure Chemicals) and 10 mL of toluene were fed into a reactor equipped with a Dean Stark dehydrating unit. This was stirred at a liquid temperature of from 140 to 165 degrees Celsius for 7 hours. Further, 0.6 g of titanium tetraisopropoxide (by Wako Pure Chemicals) was added thereto, and kept stirred for 5 hours. Accordingly, 9.5 mL of water was generated. Toluene was removed, 4 mL of water was added, and stirred at 90 degrees Celsius for 4 hours. Subsequently, 10 mL of toluene was added to the system, and water was removed at a liquid temperature of 130 degrees Celsius. The reaction system was made under reduced pressure and the volatile was removed. The system was filtered at a liquid temperature of 100 degrees Celsius or more. 60.2 g of an oil was obtained.

Figure 26:
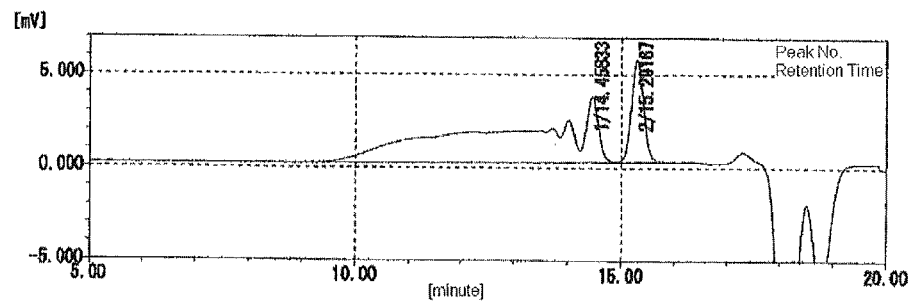
FIG. 26 This is a GPC chart of the product in Comparative Example 5.

The GPC chart of the product is shown in FIG. 26. The ratio of the light component was obtained from the GPC chart. The viscosity and the friction coefficient of the oily product were measured as above. The results are shown in Table 1.

1-27 Comparative Example 6

The viscosity and the friction coefficient of bis-{2-[2-(2-ethoxy-ethoxy)-ethoxy]-ethyl}succinate (formula 1) obtained in Production Example 1 were measured as above. The results are shown in Table 1.

1-28 Comparative Example 7

The viscosity and the friction coefficient of the light fraction mainly comprising bis-[2-(2-ethoxy-ethoxy)]-ethyl succinate (formula 2) obtained in Production Example 14 were measured as above. The results are shown in Table 1.

TABLE 1

| | Polyol | Dibasic Acid or Dibasic Acid Anhydride | Alcohol | Charging Equivalent Ratio | Proportion of Light Component | Polyol OH Residual Ratio | 40° C. Viscosity [mPas] | μ 50N 60° C. | μ 50N 80° C. | Δμ |
|---|---|---|---|---|---|---|---|---|---|---|
| Example 1 | PE | succinic anhydride | triethylene glycol monoethyl ether | 200/2/1 | 32% | 7% | 272 | 0.064 | 0.05 | −0.014 |
| Example 2 | PE | succinic acid | triethylene glycol monoethyl ether | 200/2/1 | 36% | 5% | 559 | 0.063 | 0.065 | 0.002 |
| Example 3 | PE | succinic acid | triethylene glycol monoethyl ether | 1/2/1.3 | 31% | 18% | 128 | 0.049 | 0.051 | 0.002 |
| Example 4 | PE | succinic acid | triethylene glycol monoethyl ether | 1/2/1.5 | 46% | 11% | 86 | 0.069 | 0.068 | −0.002 |
| Example 5 | PE | adipic acid | triethylene glycol monoethyl ether | 1/2/1.3 | 41% | 19% | 120 | 0.056 | 0.049 | −0.008 |
| Example 6 | PE | succinic acid | triethylene glycol monobutyl ether | 1/2/1.3 | 42% | 19% | 110 | 0.07 | 0.069 | −0.001 |
| Example 7 | PE | succinic acid | diethylene glycol monoethyl ether | 1/2/1.3 | 35% | 15% | 140 | 0.058 | 0.049 | −0.009 |
| Example 8 | PE | succinic acid | triethylene glycol monoethyl ether | 1/2/1.3 | 32% | 16% | 382 | 0.066 | 0.053 | −0.013 |
| Example 9 | TMP | succinic acid | triethylene glycol monoethyl ether | 1/2/1.3 | 39% | 13% | 110 | 0.053 | 0.058 | 0.006 |
| Example 10 | TMP | adipic acid | triethylene glycol monoethyl ether | 1/2/1.3 | 42% | 18% | 57 | 0.051 | 0.045 | −0.006 |
| Example 11 | Gly | succinic acid | triethylene glycol monoethyl ether | 1/2/1.3 | 54% | — | 52 | 0.068 | 0.069 | 0.001 |
| Example 12 | DPE | succinic acid | triethylene glycol monoethyl ether | 1/2/1.3 | 37% | — | 660 | 0.047 | 0.043 | −0.004 |
| Example 13 | PE | sebacic acid | triethylene glycol monoethyl ether | 1/2/1.3 | 38% | 15% | 177 | 0.058 | 0.062 | 0.004 |
| Example 14 | PE | succinic acid | diethylene glycol monoethyl ether | — | 12% | 15% | 1297 | 0.06 | 0.063 | 0.003 |
| Example 15 | PE | succinic acid | diethylene glycol monoethyl ether | — | 44% | 15% | 99 | 0.038 | 0.028 | −0.009 |
| Example 16 | PE | succinic acid | diethylene glycol monoethyl ether | — | 68% | 15% | 32 | 0.047 | 0.053 | 0.006 |
| Example 17 | PE | succinic acid | triethylene glycol monoethyl ether | 1/2/1.3 | 31% | 18% | 120 | 0.073 | 0.051 | −0.023 |
| Comparative Example 1 | PE | succinic anhydride | 1-decyl alcohol | 200/2/1 | 31% | 6% | 102 | 0.075 | 0.097 | 0.022 |
| Comparative Example 2 | PE | succinic anhydride | 1-dodecyl alcohol | 200/2/1 | 32% | 5% | Not tested because of solid. | | | |
| Comparative Example 3 | PE | succinic anhydride | 3,3,5-trimethyl hexanol | 200/2/1 | 33% | 7% | 142 | 0.098 | 0.113 | 0.016 |
| Comparative Example 4 | PE | succinic acid | 3,3,5-trimethyl hexanol | 1/2/1.3 | 25% | 16% | 558 | 0.092 | 0.099 | 0.007 |
| Comparative Example 5 | TMP | succinic acid | 3,3,5-trimethyl hexanol | 1/1.4/0.8 | 18% | 10% | 1215 | 0.075 | 0.085 | 0.01 |
| Comparative Example 6 | — | — | — | — | 100% | — | 18 | 0.109 | 0.133 | 0.024 |
| Comparative Example 7 | — | — | — | — | 100% | — | 11 | 0.113 | 0.141 | 0.028 |

In Table 1, PE means pentaerythritol, TMP means trimethylolpropane, Gly means glycerin and DPE means dipentaerythritol.

As in the above, the complex alcohol ester compositions of the invention have a low friction coefficient, and the friction coefficient fluctuation thereof is small or lowers with temperature elevation.

On the other hand, the complex alcohol ester compositions of Comparative Examples 1 to 5 falling outside the scope of the invention have a high friction coefficient and the friction coefficient fluctuation thereof is high with temperature elevation.

The light component alone mainly comprising a dibasic acid diester as in Comparative Examples 6 and 7 has a high friction coefficient and the friction coefficient fluctuation thereof increases with temperature elevation.

2. Test Example 2

Performance Evaluation of Grease Composition 2-1 Example 22

The oil obtained in Example 1 and a thickener, lithium stearate were mixed in a ratio by mass of 73/27 to prepare a grease sample G1.

2-2 Example 23

The oil obtained in Example 1 and an urea (prepared by reacting 1 equivalent of diphenylmethane 4,4'-diisocyanate and 2 equivalents of octadecylamine) were mixed in a ratio by mass of 83/17 to prepare a grease sample G2.

2-3 Comparative Example 8

The oil obtained in Comparative Example 3 and a thickener, lithium stearate were mixed in a ratio by mass of 73/27 to prepare a grease sample G3.

2-4 Evaluation

The friction coefficient of the above G1 to G3 was measured. Using the above-mentioned oscillation-type frictional wear tester (Optimol Instruments Prueftechnik GmbH's trade name, SRV 4), the sample was tested on a ball-on-plate under the condition mentioned below. Test piece (friction material), SUJ-2; plate, $\phi 24 \times 6.9$ mm; ball, $\phi 10$ mm; temperature, 70 degrees Celsius; load, 100 N; amplitude, 1.0 mm; frequency, 50 Hz; test time, 30 minutes after the start of the test.

The results are shown in Table 2 below.

TABLE 2

| | Grease | Oil | Thickener | Blend Ratio | Friction Coefficient |
|---|---|---|---|---|---|
| Example 22 | G1 | oil obtained in Example 1 | lithium stearate | 73:27 | 0.047 |
| Example 23 | G2 | oil obtained in Example 1 | urea | 83:17 | 0.055 |
| Comparative Example 8 | G3 | oil obtained in Comparative Example 3 | lithium stearate | 73:27 | 0.070 |

From the results in Table 2 above, it is understood that the grease composition samples of Examples of the invention noticeably express the friction-reducing effect and the friction-controlling effect thereof.

3. Test Example 3

Performance Evaluation as Mold Release

3-1 Example 24

100 parts by mass of a polycarbonate resin (by Sumitomo Dow, having a molecular weight of 20500) and 0.4 parts by mass of the oil obtained in Example 1 were mixed with a tumbler, and using a double-screw extruder, this was pelletized at a melt temperature of 280 degrees Celsius.

Using an injection-molding machine, the pellets were molded into a box-shaped article having a size of width 200×length 250×depth 400 mm and a thickness of 2.5 mm (draft, 2°), whereupon the load given to the injector in releasing the article from the mold was recorded as voltage, and the computed power value was converted into a force (kgf) to determine the mold release resistance. The result is shown in Table 3 below.

3-2 Comparative Example 9

This is the same as Example 24 except that the oil obtained in Comparative Example 3 was used in place of the oil obtained in Example 1. The result is shown in Table 3 below.

TABLE 3

| | Oil | Release Resistance [Kgf] |
|---|---|---|
| Example 24 | Oil in Example 1 | 390 |
| Comparative Example 9 | Oil in Comparative Example 3 | 460 |

From the results in Table 3 above, it is understood that the composition of Example of the invention is excellent in mold releasability.

4. Test Example 4

Evaluation as Lubricant Oil for Internal Combustion Engines

4-1 Examples 25 to 27

The oil obtained in Example 1 and a mineral oil (100 neutral oil, having a viscosity at 100 degrees Celsius of 4.4 mm/s$^2$) were mixed in a ratio by mass of 35/65 and 15/85, thereby preparing lubricant oil compositions L1 and L2 each containing 2.0% by mass of calcium sulfonate serving as a metal cleaning agent, and the friction coefficient thereof was measured. The solid obtained in Example 20 and a mineral oil (100 neutral oil, having a viscosity at 100 degrees Celsius of 4.4 mm/s$^2$) were mixed in a ratio by mass of 3/97, thereby preparing a lubricant oil composition L3, and the friction coefficient thereof was measured. The results are shown in the following Table.

The friction coefficient was measured using the above-mentioned oscillation-type frictional wear tester (Optimol Instruments Prueftechnik GmbH's trade name, SRV 4) under the condition of frequency 50 Hz, amplitude 1.5 mm, load 50 N, temperature 65 degrees Celsius and test time 30 minutes.

4-2 Comparative Examples 10 to 12

Lubricant oil compositions L4 and L5 were prepared in the same manner as in Examples 25 and 26, except that the oil obtained in Comparative Example 3 was used in place of the oil obtained in Example 1, and the friction coefficient thereof was measured similarly.

A Lubricant oil composition L6 was prepared in the same manner as in Example 27, except that the solid obtained in Comparative Example 2 was used in place of the solid obtained in Example 20, and the friction coefficient thereof was measured similarly. The results are shown in the following Table.

TABLE 4

| | Lubricant Oil Composition | Additive | Amount Added | Friction Coefficient |
|---|---|---|---|---|
| Example 25 | L1 | oil obtained in Example 1 | 35% | 0.071 |
| Example 26 | L2 | oil obtained in Example 1 | 15% | 0.056 |
| Example 27 | L3 | solid obtained in Example 20 | 3% | 0.047 |
| Comparative Example 10 | L4 | oil obtained in Comparative Example 3 | 35% | 0.102 |
| Comparative Example 11 | L5 | oil obtained in Comparative Example 3 | 15% | 0.098 |
| Comparative Example 12 | L6 | solid obtained in Comparative Example 2 | 3% | 0.072 |

It is understood that the friction coefficient of the samples of Examples 25 to 27 is lower than that of the samples of Comparative Examples 10 to 12. Accordingly, the composition of the invention can be favorably used as lubricant oil for automobiles, for example, for oil for internal combustion engines such as automobile engines, gear oil, automatic transmission fluid, shock absorber oil, etc.

5. Test Example 5

Performance Evaluation as Metal Working Lubricant Oil 5-1 Examples 28 and 29

The oil obtained in Example 1, a mineral oil with 3.2 mm$^2$/s (40 degrees Celsius), an oily agent (lauryl alcohol and myristyl alcohol, 6/4) and water were mixed in the ratio shown in the following Table, thereby preparing metal working lubricant oil compositions L7 and L8.

5-2 Comparative Examples 13 and 14

Metal working lubricant oil compositions L9 and L10 were prepared in the same manner as in Examples 28 and 29 except that the oil obtained in Comparative Example 3 was used in place of the oil obtained in Example 1.

These compositions were variously tested according to the methods mentioned below. As the rolling material, used was JIS A-1050 H18 (0.8 mm in thickness).
(i) Rolling Aptitude Test:
The compositions were tested in a rolling test under the condition mentioned below, in which the rolling reduction, {(initial thickness of the material−remaining thickness of the rolled material)/initial thickness of the material}×100%, was gradually increased, and the rolling reduction before seizure or herringbone generation failure (critical upset ratio) was determined.
Rolling Reduction: from 40% (increased at regular time intervals).
Rolling Speed: 50 m/min.
(ii) Test for Measurement of Roll Coating Amount:
Under the condition mentioned below, three coils each having a length of 300 m/coil were continuously rolled, and thereafter the roll coating formed on the surface of the roll was dissolved in an aqueous sodium hydroxide solution, and aluminium in the solution was quantified through atomic absorptiometry. From the value, the roll coating amount was determined.
Rolling Reduction: 50%.
Rolling Speed: 300 m/min.
(iii) Test for Measurement of Abrasion Powder Amount:
Under the condition mentioned below, three coils each having a length of 300 m/coil were continuously rolled. After the test, the amount of aluminium in the oil was measured through atomic absorptiometry, and the aluminium concentration in the oil was thereby determined. The abrasion powder adhering to the aluminium surface after to rolling was wiped with absorbent cotton, then the thus-wiped abrasion powder was determined through atomic absorptiometry, and the amount of the abrasion powder adhering to the plate surface after the rolling was thereby determined. Both the aluminium amount in the oil and the abrasion powder amount adhering to the plate surface were converted into a unit value in rolling 1 m$^2$ of the rolling material, and the total of the two are taken as the abrasion powder amount.
Rolling Reduction: 50%.
Rolling Speed: 300 m/min.
The above test results are shown in the following Table.

TABLE 5

|  | Lubricant Oil Composition | Oil | Amount of Oil Added [% by mass] | Amount of Mineral Oil Added [% by mass] | Amount of Water Added [% by mass] | Amount of Oily Agent Added [% by mass] | Critical Upset Ratio [%] | Coating Amount [mg] | Abrasion Powder Generation [ppm] |
|---|---|---|---|---|---|---|---|---|---|
| Example 28 | L7 | oil obtained in Example 1 | 7 | 90 | 0 | 3 | 81 | 1.1 | 67 |
| Example 29 | L8 | oil obtained in Example 1 | 15 | 45 | 40 | 0 | 78 | 0.5 | 79 |
| Comparative Example 13 | L9 | oil obtained in Comparative Example 3 | 7 | 90 | 0 | 3 | 65 | 1.7 | 102 |
| Comparative Example 14 | L10 | oil obtained in Comparative Example 3 | 15 | 45 | 40 | 0 | 72 | 0.8 | 92 |

From the results shown in the above Table, it is understood that the metal working lubricant oil compositions samples L7 and L8 of Examples of the invention are resistant to aluminium working at high speed and at high rolling reduction, and can improve the working environment and noticeably reduce the metal soap formation or abrasion powder generation. These are better than L9 and L10.

6. Test Example 6

Friction Performance Evaluation on Sintered Bearing 6-1 Examples 30 and 31

Antioxidants AO-1 (octadecyl-3-(3,5-di-t-butyl-4-hydroxyphenol) and AO-2 (zinc diamyldithiocarbamate) were added to the oil obtained in Example 1, in an amount of 0.5% by mass each, thereby preparing compositions L11 and L12.

6-2 Comparative Examples 15 and 16

Antioxidants AO-1 (octadecyl-3-(3,5-di-t-butyl-4-hydroxyphenol) and AO-2 (zinc diamyldithiocarbamate) were added to the oil obtained in Comparative Example 3, in an amount of 0.5% by mass each, thereby preparing compositions L13 and L14.

Two sintered bearings to be tested were put in a glass chamber, immersed in each lubricant oil composition (4 mL) therein, and heated in a thermostat at 150 degrees Celsius for 300 hours. As the sintered bearings, herein used were sintered bearings having a size of inner diameter 3 mm×outer diameter 6 mm×height 2.5 mm (Hitachi Powdered Metals' EAK-3). The constituent metal composition of the bearing was Cu, from 50 to 55% by mass; Sn, from 1 to 3% by mass; P, from 0.1 to 0.5% by mass; C, at most 1.0% by mass; others, at most 0.5% by mass; and balance Fe. After the bearings were immersed and heated in each lubricant oil sample, the friction coefficient of the bearing was measured. The results are shown in the following Table.

The test condition was as follows: Bearing, SUS420J2; load, 30 kgf; rotation number, 2000 rpm; clearance, 15 μm; ambient temperature, 25 degrees Celsius.

TABLE 6

| Lubricant Oil Composition | Oil | Antioxidant | Friction Coefficient |
|---|---|---|---|
| Example 30 | L11 | oil obtained in Example 1 | AO-1 | 0.23 |
| Example 31 | L12 | oil obtained in Example 1 | AO-2 | 0.28 |
| Comparative Example 15 | L13 | oil obtained in Comparative Example 3 | AO-1 | 0.45 |
| Comparative Example 16 | L14 | oil obtained in Comparative Example 3 | AO-2 | 0.48 |

From the results shown in the above Table, it is understood that, when the lubricant oil compositions L11 and L12 of the invention are used, then the friction coefficient of the bearing greatly lower, and in addition, when an antioxidant is used in the compositions, the friction coefficient lowering effect is augmented. Reduction in the friction coefficient of bearings contributes toward energy saving performance and life prolongation of memory devices, home electrical appliances using the bearings. The effect of these compositions is better than that of L13 and L14 of Comparative Examples.

7. Test Example 7

Evaluation as Internal Combustion Engine Lubricant Oil by Synthesis and Minor Addition 7-1 Example 32

6.3 g of pentaerythritol (by Wako Pure Chemicals), 22.0 g of succinic acid (by Wako Pure Chemicals), 212.7 g of polyethylene glycol monododecyl ether (prepared by reacting 1 mol of Takemoto Oil & Fat's lauryl alcohol $C_{12}H_{25}OH$ and about 10 mols of ethylene oxide; this was confirmed to have a composition of $C_{12}H_{25}(OCH_2CH_2)_{11}OH$ from the integral ratio of the methyl group and the oxyethylene group in $^1$HNMR analysis thereof, and accordingly, the theoretical molecular weight of the compound was 626; and in GPC analysis, the polystyrene-equivalent Mw thereof was 1140 and Mn thereof was 1040) and 10 mL of toluene were fed into a reactor equipped with a Dean Stark dehydrating unit. This was stirred at a liquid temperature of from 140 to 190 degrees Celsius for 9 hours. During this, toluene was refluxed and water was thereby removed. Toluene was evaporated away to give a yellow liquid. GPC of the product confirmed that the proportion of the light component was 38%.

7-2 Example 33

6.3 g of pentaerythritol (by Wako Pure Chemicals), 22.0 g of succinic acid (by Wako Pure Chemicals), 98.9 g of polyethylene glycol monododecyl ether (prepared by reacting 1 mol of Takemoto Oil & Fat's lauryl alcohol $C_{12}H_{25}OH$ and about 4 mols of ethylene oxide; this was confirmed to have a composition of $C_{12}H_{25}(OCH_2CH_2)_{3.7}OH$ from the integral ratio of the methyl group and the oxyethylene group in $^1$HNMR analysis thereof, and accordingly, the theoretical molecular weight of the compound was 349; and in GPC analysis, the polystyrene-equivalent Mw thereof was 650 and Mn thereof was 560) and 10 mL of toluene were fed into a reactor equipped with a Dean Stark dehydrating unit. This was stirred at a liquid temperature of from 140 to 190 degrees Celsius for 9 hours. During this, toluene was refluxed and water was thereby removed. Toluene was evaporated away to give a yellow liquid. GPC of the product confirmed that the proportion of the light component was 36%.

7-3 Examples 34 to 38

The solid or oil obtained in Examples 19 to 21, 32 and 33 was mixed with Nippon Oil Corporation's Super Oil N32 in a ratio by mass of 1/99 to prepare lubricant oil compositions L15 to L19, and their friction coefficient was measured. The results are shown in the following Table.

The friction coefficient was measured using the above-mentioned oscillation-type frictional wear tester (Optimol Instruments Prueftechnik GmbH's trade name, SRV @4) under the condition of frequency 50 Hz, amplitude 1.5 mm, load 50 N, temperature 65 degrees Celsius and test time 30 minutes.

7-4 Comparative Examples 17 to 18

The solid or oil obtained in Comparative Examples 2 and 3 was mixed with Nippon Oil Corporation's Super Oil N32 in a ratio by mass of 1/99 to prepare lubricant oil compositions L20 to L21, and their friction coefficient was measured in the same manner as above. The results are shown in the following Table.

7-5 Comparative Example 19

The friction coefficient of Nippon Oil Corporation's Super Oil N32 alone was measured. The result is shown in the following Table.

TABLE 7

| | Lubricant Oil Composition | Additive | Amount Added | Friction Coefficient |
|---|---|---|---|---|
| Example 34 | L15 | solid obtained in Example 19 | 1% | 0.090 |
| Example 35 | L16 | solid obtained in Example 20 | 1% | 0.083 |
| Example 36 | L17 | solid obtained in Example 21 | 1% | 0.079 |
| Example 37 | L18 | liquid obtained in Example 32 | 1% | 0.068 |
| Example 38 | L19 | liquid obtained in Example 33 | 1% | 0.078 |
| Comparative Example 17 | L20 | solid obtained in Comparative Example 2 | 1% | 0.115 |
| Comparative Example 18 | L21 | oil obtained in Comparative Example 3 | 1% | 0.110 |
| Comparative Example 19 | — | none | — | 0.124 |

It is understood that the friction coefficient of the samples of Examples 34 to 38 is lower than that of the samples of Comparative Examples 17 and 18 and also than that of the sample of Comparative Example 19 with no additive. Accordingly, the composition of the invention can be favorably used as lubricant oil for automobiles, for example, for oil for internal combustion engines such as automobile engines, gear oil, automatic transmission fluid, shock absorber oil, etc.

8. Test Example 8

Evaluation as Internal Combustion Engine Lubricant Oil by Synthesis and Minor Addition 8-1 Example 39

82.3 g of trimethylolpropane (by Wako Pure Chemicals), 272.1 g of adipic acid (by Wako Pure Chemicals), 432.6 g of 2-(2-ethylhexyloxy)ethanol (by Wako Pure Chemicals) and 25 mL of toluene were fed into a reactor equipped with a Dean Stark dehydrating unit. This was stirred at a liquid temperature of from 140 to 210 degrees Celsius for 8 hours. During this, toluene was refluxed and water was thereby removed. Toluene was evaporated away to give a yellow liquid.

Figure 31:
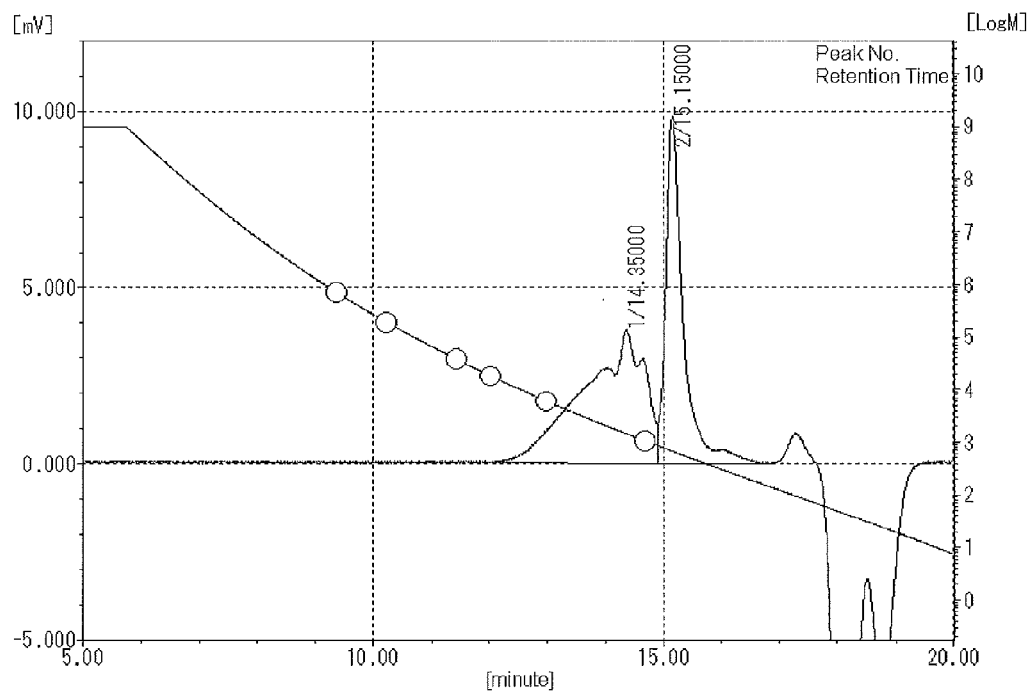
FIG. 31 This is a GPC chart of the product in Example 39.

The GPC chart of the product is shown in FIG. 31. From this, the proportion of the light component was 46%.

8-2 Example 40

16.5 g of trimethylolpropane (by Wako Pure Chemicals), 210.4 g of dimer acid hydrogenate (by Aldrich), 85.8 g of 2-(2-ethylhexyloxy)ethanol (by Wako Pure Chemicals) and 15 mL of toluene were fed into a reactor equipped with a Dean Stark dehydrating unit. This was stirred at a liquid temperature of from 140 to 210 degrees Celsius for 8 hours. During this, toluene was refluxed and water was thereby removed. Toluene was evaporated away to give a yellow liquid.

Figure 32:
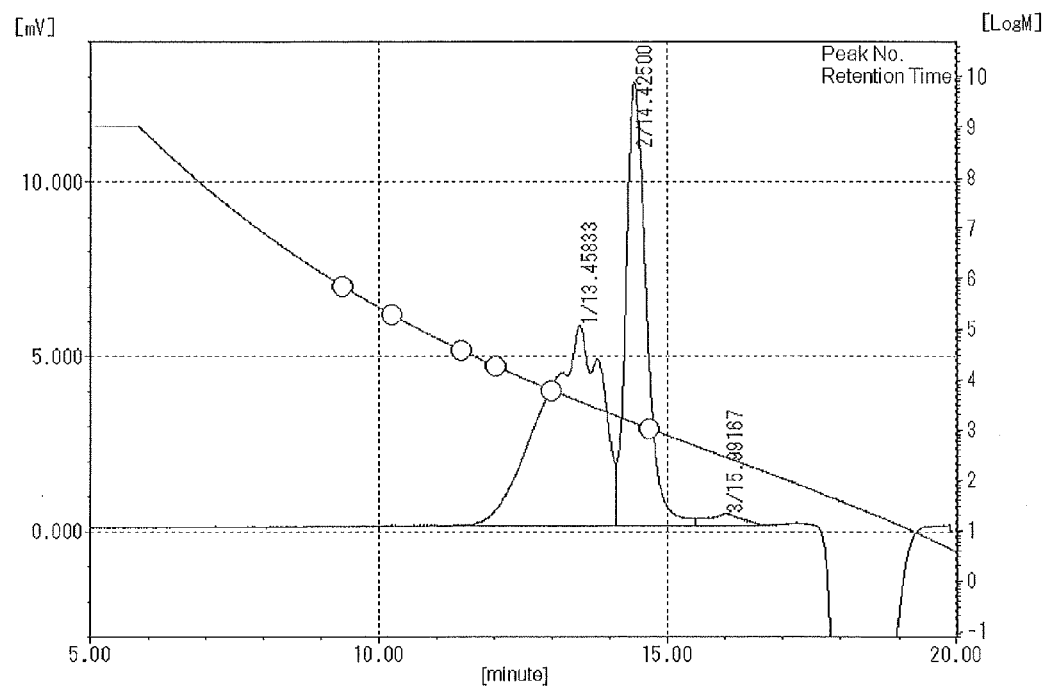
FIG. 32 This is a GPC chart of the product in Example 40.

The GPC chart of the product is shown in FIG. 32. From this, the proportion of the light component was 47%.

8-3 Example 41

16.5 g of trimethylolpropane (by Wako Pure Chemicals), 210.4 g of dimer acid (Tsuno Food Industrial's Tsunodime 395), 85.8 g of 2-(2-ethylhexyloxy)ethanol (by Wako Pure Chemicals) and 15 mL of toluene were fed into a reactor equipped with a Dean Stark dehydrating unit. This was stirred at a liquid temperature of from 140 to 210 degrees Celsius for 8 hours. During this, toluene was refluxed and water was thereby removed. Toluene was evaporated away to give a yellow liquid.

Figure 33:
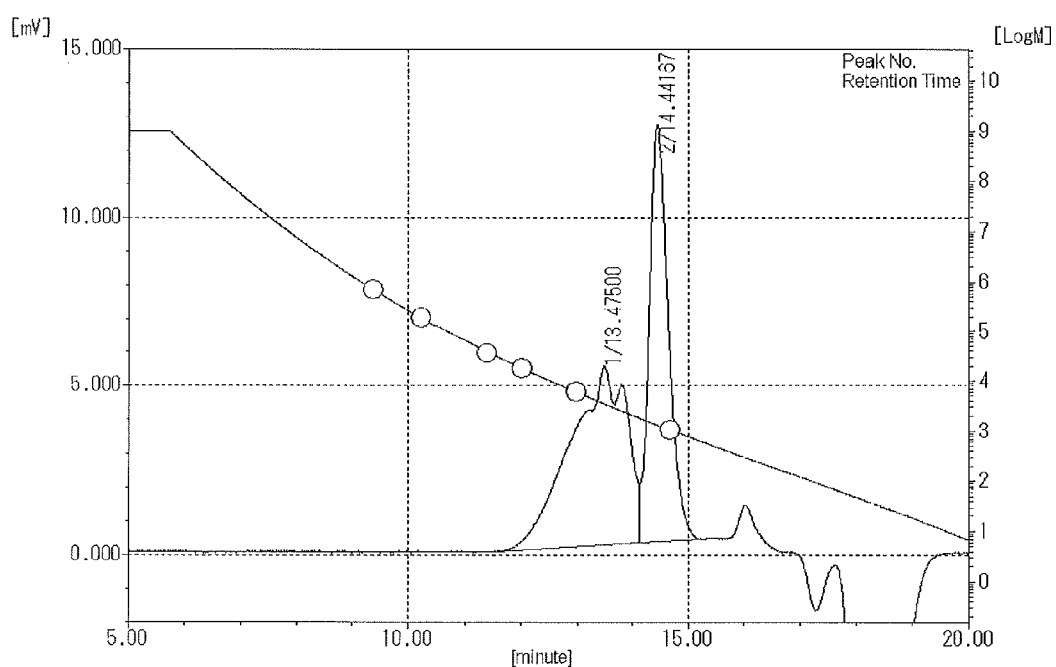
FIG. 33 This is a GPC chart of the product in Example 41.

The GPC chart of the product is shown in FIG. 33. From this, the proportion of the light component was 44%.

8-4 Examples 42 to 44

The oil obtained in Examples 39 to 41 was mixed with Nippon Oil Corporation's Super Oil N32 in a ratio by mass of 10/90 to prepare lubricant oil compositions L22 to L24, and their friction coefficient was measured. The results are shown in Table 8 below.

8-5 Comparative Examples 20 to 24

Yellow liquids of Comparative Examples 20 to 22 were prepared according to the same operation as in Examples 39 to 41 except that an equimolar amount of 2-ethylhexanol was used in place of the alcohol used in Examples 39 to 41. Yellow liquids of Comparative Examples 23 to 24 were prepared according to the same operation as in Examples 39 to 41 except that an equimolar amount of decanol was used in place of the alcohol used in Examples 39 to 41.

8-6 Comparative Examples 25 to 29

The oil obtained in Comparative Examples 20 to 24 was mixed with Nippon Oil Corporation's Super Oil N32 in a ratio by mass of 10/90 to prepare lubricant oil compositions L25 to L29, and their friction coefficient was measured. The results are shown in Table 8 below along with the result of Comparative Example 19 therein.

TABLE 8

| | Lubricant Oil Composition | Additive | Amount Added | Friction Coefficient |
|---|---|---|---|---|
| Example 42 | L22 | oil obtained in Example 39 | 10% | 0.080 |
| Example 43 | L23 | oil obtained in Example 40 | 10% | 0.076 |
| Example 44 | L24 | oil obtained in Example 41 | 10% | 0.074 |
| Comparative Example 25 | L25 | oil obtained in Comparative Example 20 | 10% | 0.115 |
| Comparative Example 26 | L26 | oil obtained in Comparative Example 21 | 10% | 0.110 |
| Comparative Example 27 | L27 | oil obtained in Comparative Example 22 | 10% | 0.110 |
| Comparative Example 28 | L28 | oil obtained in Comparative Example 23 | 10% | 0.118 |
| Comparative Example 29 | L29 | oil obtained in Comparative Example 24 | 10% | 0.109 |
| Comparative Example 19 | — | — | — | 0.124 |

It is understood that the friction coefficient of the samples of Examples 42 to 44 is lower than that of the samples of Comparative Examples 25 to 29, in which the alcohol used did not have an ethyleneoxy group adjacent to the hydroxyl group, and also than that of the sample of Comparative Example 19 with no additive. Accordingly, the composition of the invention can be favorably used as lubricant oil for automobiles, for example, for oil for internal combustion engines such as automobile engines, gear oil, automatic transmission fluid, shock absorber oil, etc.

The invention claimed is:
1. A complex alcohol ester composition comprising a polyester in which at least two molecules of a polyol represented by a formula I: $R(OH)_n$ (wherein R represents an n-valent aliphatic, alicyclic or aromatic group, one or more carbon atoms not adjacent to each other in R may be individually substituted with an oxygen atom, and n indicates an integer of 3 or more) are linked through at least two ester bonds via at least one molecule of a polybasic acid, and at least a part of the non-linked side chain ends of the polyol have a group represented by a formula II: $-O-(AO)_k R^2$ (wherein $R^2$ represents a hydrocarbon group, A represents a divalent linking group, and k indicates an integer of from 1 to 30) derived from a monoalcohol represented by a formula III: $HO(AO)_k R^2$ (wherein $R^2$ represents a hydrocarbon group, A represents a divalent linking group, and k indicates an integer of from 1 to 30) via a polybasic acid.
2. The complex alcohol ester composition according to claim 1, wherein at least one of said polyester has a structure represented by the following formula Y:

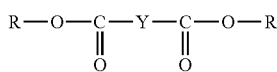 Formula Y wherein R represents a monovalent or more multivalent residue derived from R(OH)$_n$ in claim 1 by removing at least two OH groups, and Y represents a residue derived from the polybasic acid in claim 1 by removing two carboxyl groups.

3. The complex alcohol ester composition according to claim 1, wherein the polyester further comprises a polybasic acid ester-containing light component.

4. The complex alcohol ester composition according to claim 1, which comprises the light component in an amount of at most 90% by mass of the total mass of the composition.

5. The complex alcohol ester composition according to claim 1, wherein n in the formula I is 3 or 4.

6. The complex alcohol ester composition according to claim 1, wherein R in the formula I contains from 2 to 20 carbon atoms.

7. The complex alcohol ester composition according to claim 1, wherein the polyol is pentaerythritol, trimethylolpropane, glycerin or dipentaerythritol.

8. The complex alcohol ester composition according to claim 1, wherein the polybasic acid is a dibasic acid.

9. The complex alcohol ester composition according to claim 8, wherein the dibasic acid is succinic acid, adipic acid, sebacic acid, or an anhydride thereof.

10. The complex alcohol ester composition according to claim 8, wherein the dibasic acid is a dimer acid or a hydrogenate thereof.

11. The complex alcohol ester composition according to claim 3, wherein the polybasic acid ester-containing light component contains a compound represented by formula VIa:

Formula VIa:

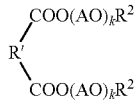

wherein R' represents a linear or cyclic, divalent saturated or unsaturated hydrocarbon group; and $R^2$, A and k have the same meanings as those in the formula II in claim 1.

12. The complex alcohol ester composition according to claim 3, wherein the polybasic acid ester-containing light component contains a compound represented by the formula VIb:

Formula VIb:

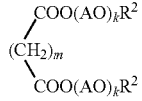

wherein m indicates an integer of from 1 to 10; and $R^2$, A and k have the same meanings as those in the formula II in claim 1.

13. The complex alcohol ester composition according to claim 1, wherein $R^2$ in the formula II has from 1 to 30 carbon atoms.

14. The complex alcohol ester composition according to claim 1, wherein A in the formula II is an alkylene group having from 1 to 6 carbon atoms, $R^2$ is an alkyl group having from 1 to 8 carbon atoms, and k is an integer of from 1 to 3.

15. The complex alcohol ester composition according to claim 1, wherein A in the formula II is an alkylene group having from 1 to 6 carbon atoms, $R^2$ is an alkyl group having from 16 to 22 carbon atoms, and k is an integer of from 10 to 20.

16. The complex alcohol ester composition according to claim 1, wherein the polyester has a group represented by the formula II and has OCOR$^1$ (wherein R$^1$ represents an alkyl group having from 1 to 10 carbon atoms, or an aryl group) in at least a part of the polyol side chain ends.

17. The complex alcohol ester composition according to claim 16, wherein R$^1$ is an alkyl group having from 1 to 4 carbon atoms.

18. The complex alcohol ester composition according to claim 1, of which the viscosity at 40 degrees Celsius is from 50 to 700 mPas.

19. A composition comprising a complex alcohol ester composition of claim 1, and one or more additives selected from a friction inhibitor, a viscosity index improver, an antioxidant, a cleaning agent, a dispersant, a flowing agent, a curing agent, a corrosion inhibitor, a sealability enhancer, a defoaming agent, a rust protector, a friction controlling agent, and a thickener.

20. A composition comprising a complex alcohol ester composition of claim 1, and one or more media selected from a mineral oil, an oil and fat compound, a polyolefin oil, a silicone oil, a perfluoropolyether oil, an aromatic ester oil and a polyol ester lubricant oil.

21. A lubricant comprising a complex alcohol ester composition of claim 1.

22. The lubricant according to claim 21, which is used as a lubricant oil for grease, a mold release agent, an oil for internal-combustion engines, oil for metal working (cutting), oil for bearings, a fuel for combustion engines, an engine oil for vehicles, a gear oil, an operating oil for automobiles, a lubricant oil for ships and aircraft, a machine oil, a turbine oil, an oil for bearings, a hydraulic operating oil, a compressor/vacuum pump oil, an oil for refrigerators, a metal working lubricant oil, a lubricant oil for magnetic recording media, a lubricant oil for micromachines, a lubricant oil for artificial bones, or a rolling oil.

23. A method for producing a complex alcohol ester, which comprises:
mixing
a polyol represented by a formula I: R(OH)$_n$ (wherein R represents an n-valent aliphatic, alicyclic or aromatic group, one or more carbon atoms not adjacent to each other in R may be individually substituted with an oxygen atom, and n indicates an integer of 3 or more), dimer acid or a hydrogenate thereof, and
a monoalcohol represented by a formula III: HO(AO)$_k$R$^2$ (wherein R$^2$ represents a hydrocarbon group, A represents a divalent linking group, and k indicates an integer of from 1 to 30),
and dehydrating and condensing the mixture.

24. A method for producing a complex alcohol ester, which comprises:
mixing
a polyol represented by a formula I: R(OH)$_n$ (wherein R represents an n-valent aliphatic, alicyclic or aromatic group, one or more carbon atoms not adjacent to each other in R may be individually substituted with an oxygen atom, and n indicates an integer of 3 or more), a polybasic acid or a polybasic acid anhydride, and
a monoalcohol represented by a formula Ill: $HO(AO)_kR^2$ (wherein $R^2$ represents a hydrocarbon group, A represents a divalent linking group, and k indicates an integer of from 1 to 30), and dehydrating and condensing the mixture, wherein the equivalent ratio in mixing the polyol, the polybasic acid or polybasic acid anhydride and the monoalcohol is from 1/(1.5 to 2.5)/(1.0 to 3.0).

25. The method according to claim 23, wherein a hydrocarbon solvent having a boiling point of from 110 to 160 degrees Celsius is added to the mixture in an amount of from 1 to 25% by mass of the mixture, and the condensation is carried out under azeotropic dehydration.

26. The method according to claim 23, which comprises a step of adding an acid anhydride after the dehydrating condensation to thereby acylate the remaining OH.

27. A complex alcohol ester composition comprising a dehydrating condensation reaction product of a mixture that contains:
- a polyol represented by a formula I: $R(OH)_n$ (wherein R represents an n-valent aliphatic, alicyclic or aromatic group, one or more carbon atoms not adjacent to each other in R may be individually substituted with an oxygen atom, and n indicates an integer of 3 or more),
- a dimer acid or a hydrogenate thereof, and
- a monoalcohol represented by a formula Ill: $HO(AO)_kR^2$ (wherein $R^2$ represents a hydrocarbon group, A represents a divalent linking group, and k indicates an integer of from 1 to 30).

28. The complex alcohol ester composition according to claim 27, wherein the ester is a polyester in which at least two molecules of a polyol represented by a formula I: $R(OH)_n$ (wherein R represents an n-valent aliphatic, alicyclic or aromatic group, one or more carbon atoms not adjacent to each other in R may be individually substituted with an oxygen atom, and n indicates an integer of 3 or more) are linked through at least two ester bonds via at least one molecule of a dimer acid and at least a part of the non-linked side chain ends of the polyol have a group represented by a formula II: —O-(AO)k$R^2$ (wherein $R^2$ represents a hydrocarbon group, A represents a divalent linking group, and k indicates an integer of from 1 to 30) derived from a monoalcohol represented by a formula Ill: $HO(AO)kR^2$ (wherein $R^2$ represents a hydrocarbon group, A represents a divalent linking group, and k indicates an integer of from 1 to 30) via dimer acid.

29. A method for producing a complex alcohol ester, which comprises:
mixing
- a polyol represented by a formula I: $R(OH)_n$ (wherein R represents an n-valent aliphatic, alicyclic or aromatic group, one or more carbon atoms not adjacent to each other in R may be individually substituted with an oxygen atom, and n indicates an integer of 3 or more),
- a polybasic acid or a polybasic acid anhydride, and
- a monoalcohol represented by a formula Ill: $HO(AO)_kR^2$ (wherein $R^2$ represents a hydrocarbon group, A represents a divalent linking group, and k indicates an integer of from 1 to 30), and dehydrating and condensing the mixture, wherein the complex alcohol ester comprises at least two molecules of the polyol represented by the formula I are linked through at least two ester bonds via at least one molecule of a polybasic acid, and at least a part of the non-linked side chain ends of the polyol have a group represented by a formula II: —O-(AO)$_k$$R^2$ (wherein $R^2$ represents a hydrocarbon group, A represents a divalent linking group, and k indicates an integer of from 1 to 30) derived from the monoalcohol represented by the formula III.

30. A complex alcohol ester composition comprising a dehydrating condensation reaction product of a mixture that contains:
- a polyol represented by a formula I: $R(OH)_n$ (wherein R represents an n-valent aliphatic, alicyclic or aromatic group, one or more carbon atoms not adjacent to each other in R may be individually substituted with an oxygen atom, and n indicates an integer of 3 or more),
- a polybasic acid or a polybasic acid anhydride, and
- a monoalcohol represented by a formula Ill: $HO(AO)_kR^2$ (wherein $R^2$ represents a hydrocarbon group, A represents a divalent linking group, and k indicates an integer of from 1 to 30), wherein the equivalent ratio in mixing the polyol, the polybasic acid or polybasic acid anhydride and the monoalcohol is from 1/(1.5 to 2.5)/(1.0 to 3.0).

* * * * *